US008920808B2

(12) United States Patent
Mannie

(10) Patent No.: US 8,920,808 B2
(45) Date of Patent: Dec. 30, 2014

(54) CYTOKINE-BASED FUSION PROTEINS FOR TREATMENT OF MULTIPLE SCLEROSIS

(75) Inventor: Mark D. Mannie, Greenville, NC (US)

(73) Assignee: East Carolina University, Greenville, NC (US)

( * ) Notice: Subject to any disclaimer, the term of this patent is extended or adjusted under 35 U.S.C. 154(b) by 88 days.

(21) Appl. No.: 12/447,389

(22) PCT Filed: Oct. 29, 2007

(86) PCT No.: PCT/US2007/022768
§ 371 (c)(1),
(2), (4) Date: Oct. 8, 2009

(87) PCT Pub. No.: WO2008/130382
PCT Pub. Date: Oct. 30, 2008

(65) Prior Publication Data
US 2010/0055070 A1    Mar. 4, 2010

Related U.S. Application Data

(60) Provisional application No. 60/863,692, filed on Oct. 31, 2006.

(51) Int. Cl.
| | | |
|---|---|---|
| *A61K 38/20* | (2006.01) | |
| *A61K 39/00* | (2006.01) | |
| *A61K 39/35* | (2006.01) | |
| *A61K 47/48* | (2006.01) | |
| *C07K 14/52* | (2006.01) | |
| *C12N 15/63* | (2006.01) | |
| *C12N 5/10* | (2006.01) | |
| *C12P 21/00* | (2006.01) | |
| *C07K 14/47* | (2006.01) | |
| *A61K 9/00* | (2006.01) | |

(52) U.S. Cl.
CPC ............. *A61K 39/35* (2013.01); *C07K 2319/74* (2013.01); *C07K 2319/40* (2013.01); *A61K 9/0019* (2013.01); *C07K 14/4713* (2013.01); *A61K 39/0008* (2013.01); *C07K 2319/33* (2013.01); *A61K 47/48269* (2013.01); *A61K 47/4833* (2013.01); *C07K 14/52* (2013.01)
USPC .................... 424/192.1; 435/69.1; 435/320.1; 435/325; 514/17.9; 530/351; 530/387.3; 536/23.4; 424/85.2

(58) Field of Classification Search
None
See application file for complete search history.

(56) References Cited

U.S. PATENT DOCUMENTS

| | | | | |
|---|---|---|---|---|
| 5,858,980 | A * | 1/1999 | Weiner et al. | 514/21.4 |
| 6,942,853 | B2 * | 9/2005 | Chernajovsky et al. | 424/85.1 |
| 2002/0038002 | A1 * | 3/2002 | Zaghouani | 530/388.22 |
| 2003/0017550 | A1 | 1/2003 | Pang | |
| 2005/0025744 | A1 * | 2/2005 | Lane | 424/85.6 |

FOREIGN PATENT DOCUMENTS

| | | |
|---|---|---|
| EP | 0326120 A2 | 8/1989 |
| WO | WO 91/01146 A | 2/1991 |
| WO | WO 91/01146 A1 | 2/1991 |
| WO | WO 99/32141 A1 | 7/1999 |
| WO | WO 01/68896 A | 9/2001 |
| WO | WO 03/024404 A | 3/2003 |
| WO | WO 2004/020405 A2 | 3/2004 |
| WO | WO 2004/028472 A2 | 4/2004 |
| WO | WO 2004/092210 A | 10/2004 |
| WO | WO 2006/000448 A2 | 1/2006 |
| WO | WO 2006/063800 A | 6/2006 |
| WO | WO 2006/063800 A1 | 6/2006 |

OTHER PUBLICATIONS

Kim, 1997, Arch. Pharm. Research, vol. 20, No. 5, pp. 396-403.*
Mannie, 2007, Journal of Immunology, vol. 178, pp. 2835-2843.*
Kuerten, 2006, Journal of Neuroimmunology, vol. 177, pp. 99-111.*
Calabresi, 1998, Neurology, vol. 51, pp. 289-292.*
Tuohy, 1989, The Journal of Immunology, vol. 142, issue 5, pp. 1523-1527.*
Yu, 1996, Journal of Experimental Medicine, vol. 183, pp. 1777-1788.*
Kim et al. "An ovalbumin-IL-12 fusion protein is more effective than ovalbumin plus free recombinant IL-12 in inducing a T helper cell type 1-dominated immune response and inhibiting antigen-specific IgE production", *J. of Immunology* 158(9):4137-4144 (1997).
Lim et al. "Potentiation of antigen-specific, Th1 immune responses by multiple DNA vaccination with an ovalbumin/interferon-gamma hybrid construct", *Immunology* 94(2):135-141 (1998).
Kim et al. "Efficient induction of antigen-specific T helper type 1-mediated immune responses by intramuscular injection with ovalbumin/interleukin-18 fusion DNA", *Vaccine, Butterworth Scientific* 19(30):4107-4114 (2001).
Maecker et al. "Vaccination with allergen-IL-18 fusion DNA protects against, and reverses established, airway hyperreactivity in a murine asthma model", *J. of Immunology* 166(2):959-965 (2001).
Martin et al. "Protective effect of the interleukin-1 receptor antagonist (IL-1ra) on experimental allergic encephalomyelitis in rats", *J. of Neuroimmunology*, 61(2):241-245 (1995).

(Continued)

*Primary Examiner* — Bridget E Bunner
*Assistant Examiner* — Fozia Hamud
(74) *Attorney, Agent, or Firm* — Myers Bigel Sibley & Sajovec, P.A.

(57) ABSTRACT

The present invention provides fusion proteins including an autoimmune antigen, an allergen antigen or an alloantigen, and an anti-inflammatory cytokine. Compositions and methods including the fusion proteins are also provided.

10 Claims, 21 Drawing Sheets

(56) References Cited

OTHER PUBLICATIONS

Wang et al. "Adenovirus expressing interleukin-1 receptor antagonist alleviates allergic airway inflammation in a murine model of asthma", *Gene Therapy* 13(19):1414-1421 (2006).

International Search Report corresponding to International Application No. PCT/US2007/022768 mailed Apr. 15, 2009.

Rafei et al. "A GMCSF and IL-15 Fusokine Leads to Paradoxical Immunosuppression in Vivo Via Asymmetrical JAK/STAT Signaling Through the IL-15 Receptor Complex" *Blood* 109(5):2234-2242 (2007).

Rafei et al. "A Granulocyte-Macrophage Colony-Stimulating Factor and Interleukin-15 Fusokine Induces a Regulatory B Cell Population With Immune Suppressive Properties" *Nature Medicine* Advanced Online Publication pp. 1-9 (2009).

Goodin "Treatment of Multiple Sclerosis with Human Beta Interferon", *The International MS Journal* 12:96-108 (2005).

Kieseier et al. "Interferon-β and neuroprotection in multiple sclerosis—Facts, hopes and phantasies", *Experimental Neurology* 203:1-4 (2007).

Mannie et al. "Cytokine-neuroantigen fusion proteins as a new class of tolerogenic, therapeutic vaccines for treatment of inflammatory demyelinating disease in rodent models of multiple sclerosis", *Frontiers in Immunology* 3(255):1-16 (2012).

Sung et al. "An IFN-β-Albumin Fusion Protein That Displays Improved Pharmacokinetic and Pharmacodynamic Properties in Nonhuman Primates", *Journal of Interferon & Cytokine Research* 23:25-36 (2003).

Xu et al. "Combined Nasal Administration of Encephalitogenic Myelin Basic Protein Peptide 68-86 and IL-10 Suppressed Incipient Experimental Allergic Encephalomyelitis in Lewis Rats", *Clinical Immunology* 96(3):205-211 (2000).

Xu et al. "Suppression of ongoing experimental allergic encephalomyelitis (EAE) in Lewis rats: synergistic effects of myelin basic protein (MBP) peptide 68-86 and IL-4", *Clin. Exp. Immunol.* 120:526-531 (2000).

Partial European Search Report corresponding to European Application No. 12182092.2 issued Jan. 30, 2013.

Kim et al. "An Ovalbumin-IL-12 Fusion Protein is More Effective than Ovalbumin Plus Free Recombinant IL-12 in Inducing a T Helper Cell Type 1-Dominated Immune Response and Inhibiting Antigen-Specific IgE Production[1]", *Journal of Immunology* 158:4137-4144 (1997).

Extended European Search Report corresponding to European Application No. 12182092.2 issued May 22, 2013.

* cited by examiner

FIG. 1A    PCR to generate C-terminal Ek/ GP72-88/ 6-his sequence

5A01 primer: gat gac gat gac aaa gga ccc cag aag tcg cag cgg tcc caa g

2F07 primer: tat ggt acc tta gtg gtg atg gtg atg gac gtt ttc atc ttg gga ccg ctg cga ct

```
5A01 primer
gat gac gat gac aaa gga ccc cag aag tcg cag cgg tcc caa g
                              agc gtc gcc agg gtt cta ctt ttg gga cat cag gta gtg gta gtg att cca tgg tat
                                                                                                                2F07 primer
 D   D   D   D   K   G   P   Q   K   S   Q   R   S   Q   D   E   N   P   V   V   H   H   H   H   H   H   *
   Enterokinase Site  /   Encephalitogenic 73-87 MBP peptide           /6-histidine tag   /  Stop/  Kpn I site
```

FIG. 1B    Overlap extension PCR to generate the rat IL2-EK-NAg-6his fusion construct

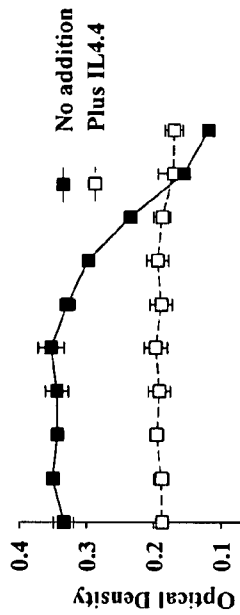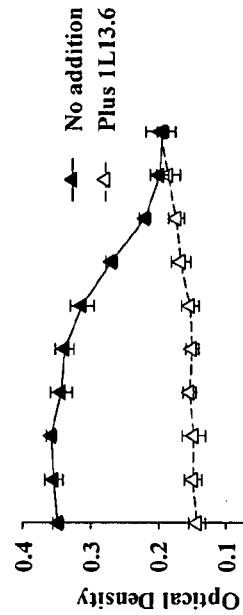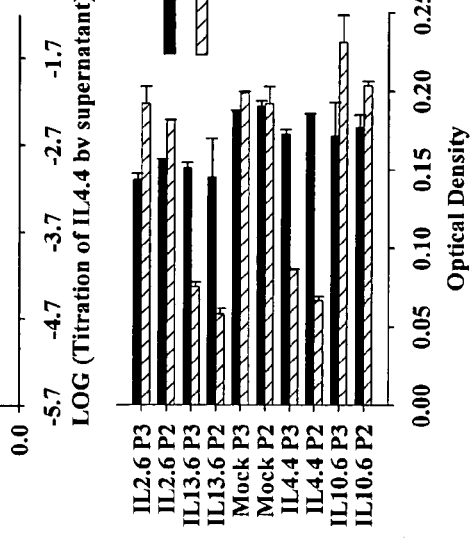
FIG. 5A
FIG. 5B
FIG. 5C

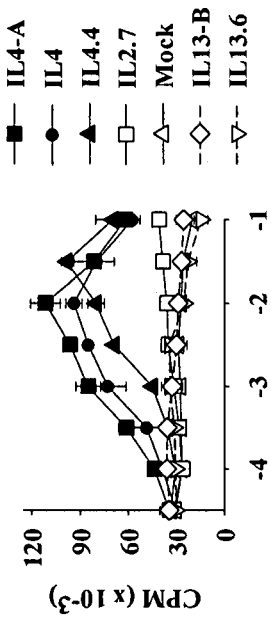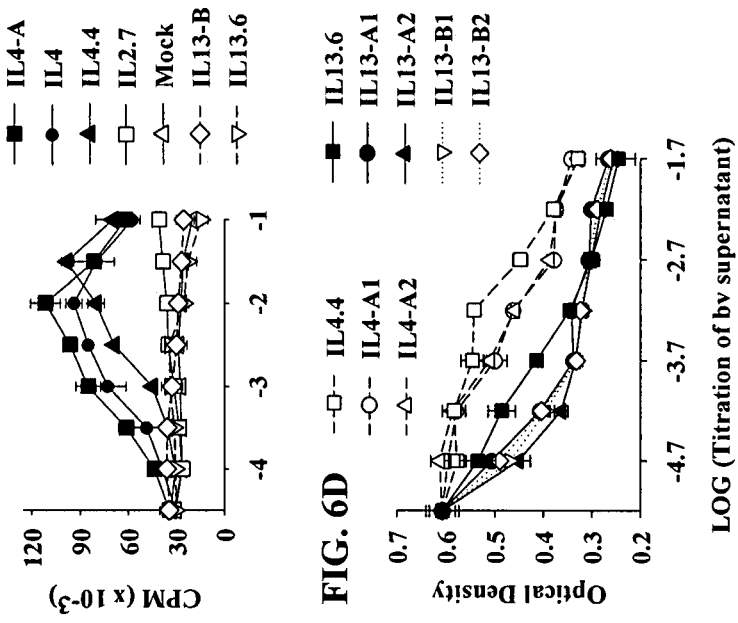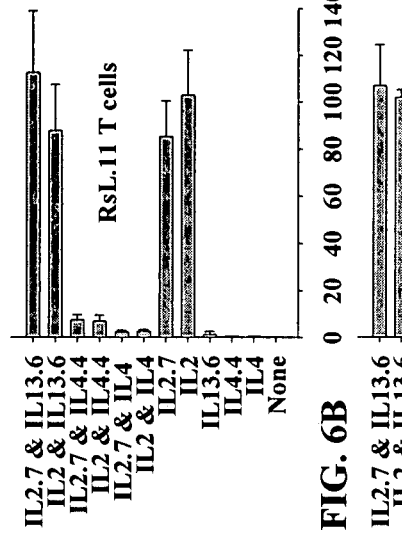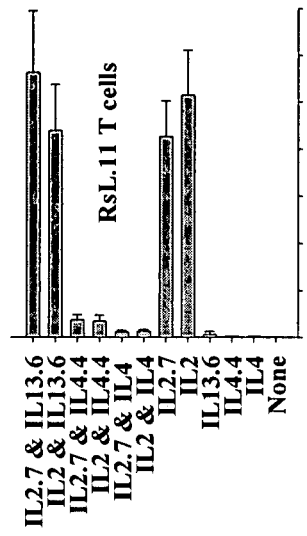

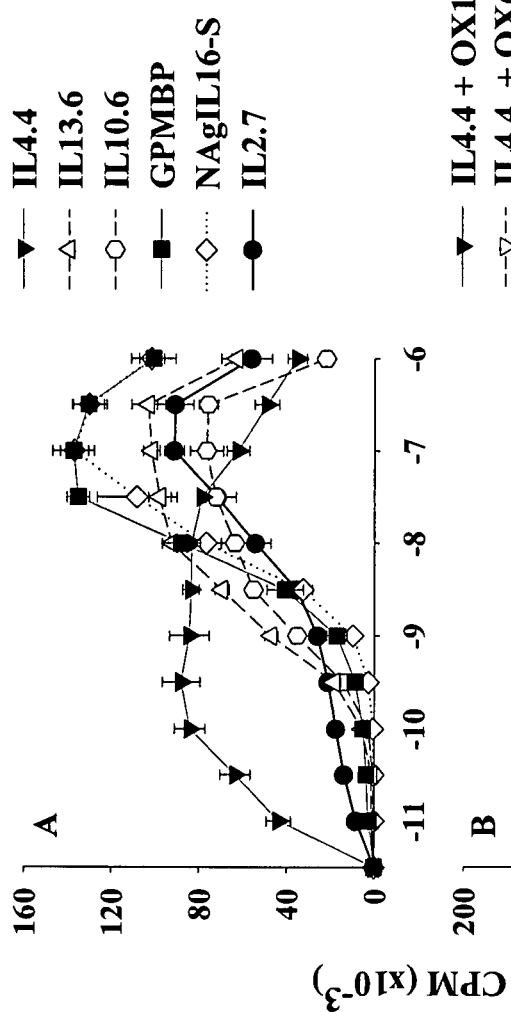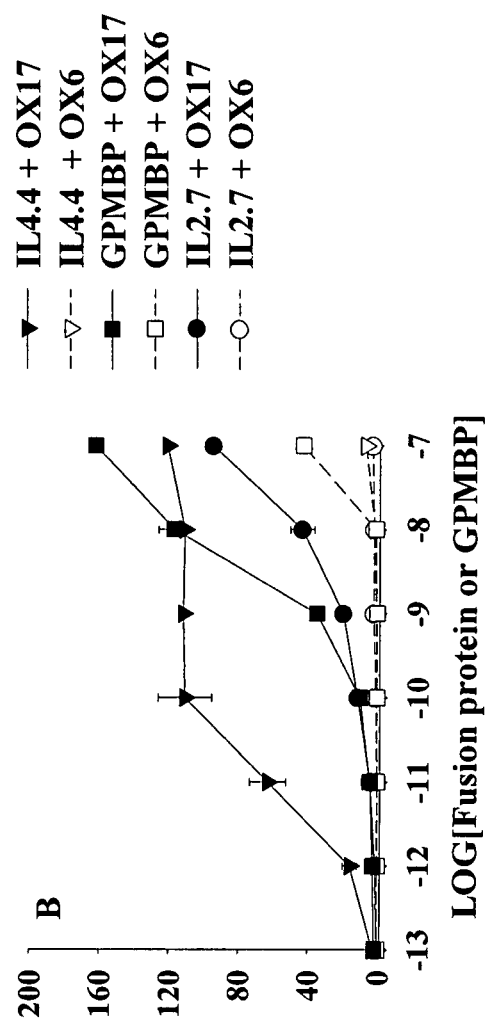
FIG. 12A
FIG. 12B

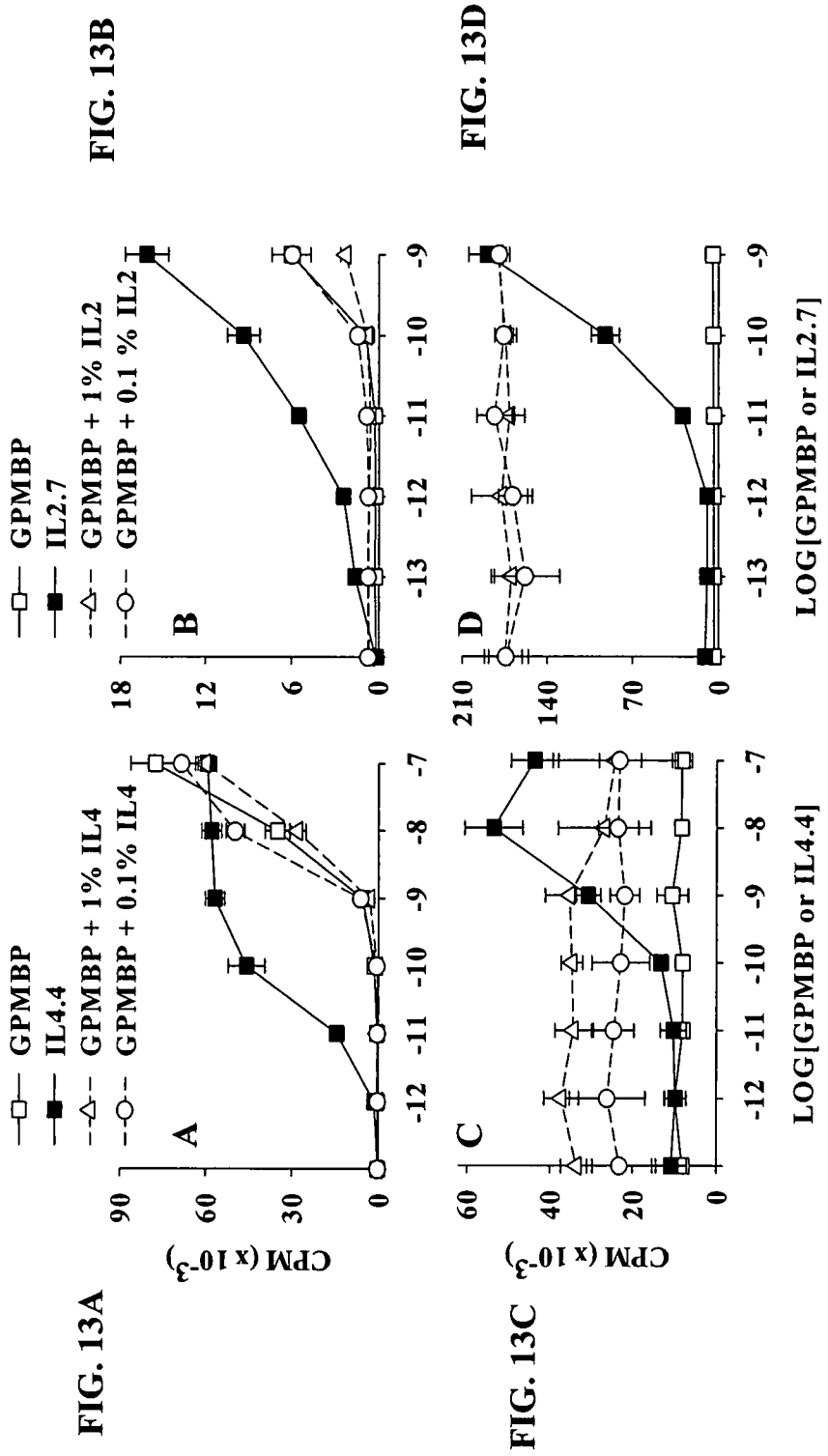

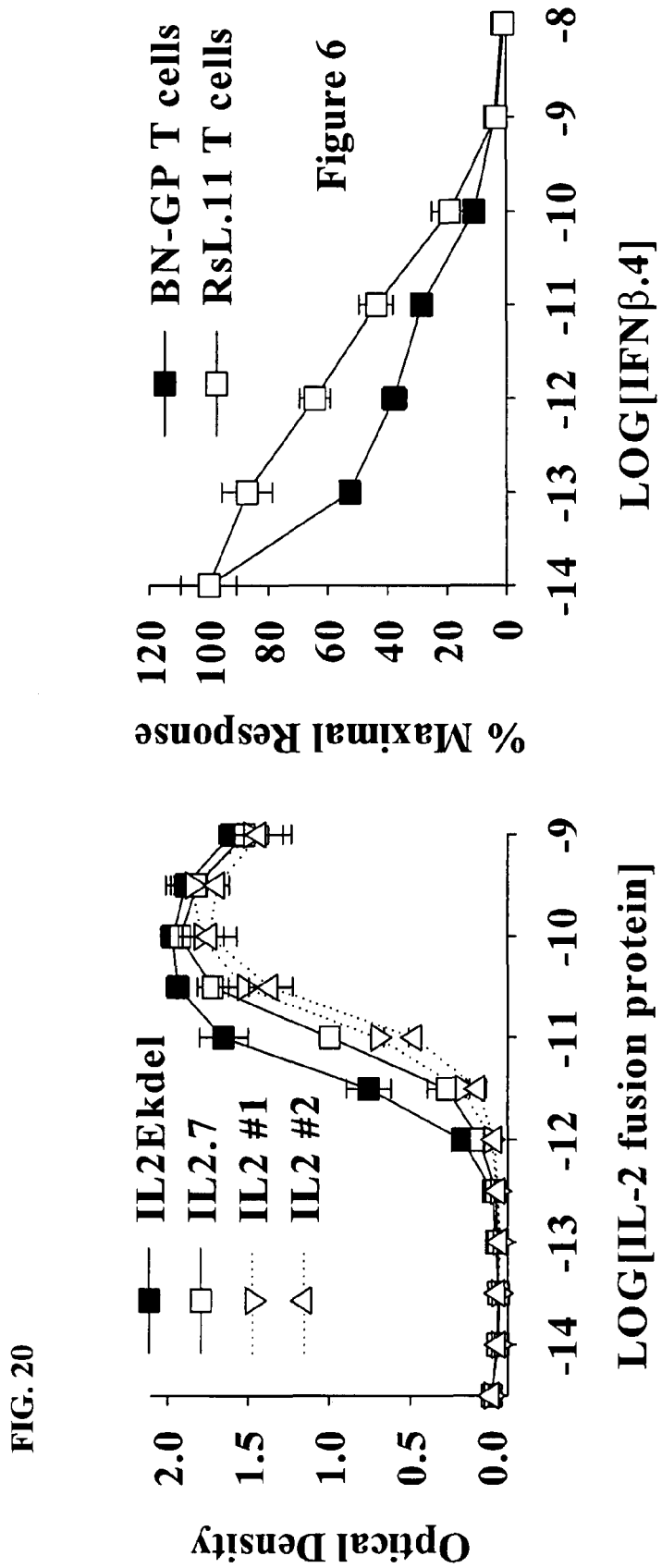

CYTOKINE-BASED FUSION PROTEINS FOR TREATMENT OF MULTIPLE SCLEROSIS

RELATED APPLICATION DATA

This application is a 37 U.S.C. §371 national phase application of International Application No. PCT/US2007/022768, filed Oct. 29, 2007, which claims the benefit of U.S. Provisional Patent Application Ser. No. 60/863,692, filed Oct. 31, 2006, the disclosures of each of which are incorporated herein by reference in their entireties.

STATEMENT REGARDING ELECTRONIC FILING OF A SEQUENCE LISTING

A Sequence Listing in ASCII text format, submitted under 37 C.F.R. §1.821, entitled 5218-156 FINAL_ST25.txt, 7,875 bytes in size, generated on Oct. 6, 2014 and filed via EFS-Web, is provided in lieu of a paper copy. This Sequence Listing is hereby incorporated by reference into the specification for its disclosures.

FIELD OF THE INVENTION

The present invention relates to compositions of matter and methods of using the same in regulating an immune response. The compositions of matter are useful in the treatment of immunological disorders, for example, in the prevention and/or treatment of autoimmune disease, allergic disease, and transplant rejection.

BACKGROUND OF THE INVENTION

Autoimmune diseases are generally believed to be caused by the failure of the immune system to discriminate between antigens of foreign invading organisms (non-self) and tissues native to the immune system's own body (self). When this failure to discriminate between self and non-self occurs, and the immune system reacts against self antigens, an autoimmune disorder may arise. Autoimmunity is a major cause of human disease. Accordingly, new strategies are desired to elicit antigen-specific immunological tolerance as a means for treatment of autoimmune disease (Fontoura et al. (2005) Int Rev Immunol 24, 415-446), and more generally, for the treatment of immunological disorders.

As opposed to generalized immunosuppression, antigen-specific regimens of tolerance induction can have improved efficacy because, at least in part, anti-inflammatory activity would be focused on the small percentage of relevant pathogenic T cells minimizing the need for global immune suppression. Antigen-specific regimens can require temporary rather than chronic administration, can be effective at lower doses and/or can require local rather than systemic application, and thus, may exhibit improved efficacy and cost-effectiveness with fewer adverse side effects. Thus, it is desirable to have improved therapeutic agents in the treatment of immunological disorders.

SUMMARY OF THE INVENTION

Fusion proteins as described herein incorporating anti-inflammatory cytokines and immunodominant self antigen as separate domains of a single protein may hold promise for development of antigen-specific tolerogenic vaccines. Proteins incorporating rat sequences of IL-1RA, IL-2, IL-4, IL-10 or IL-13 were expressed as fusion proteins containing the major encephalitogenic region of myelin basic protein (MBP). In some embodiments, these fusion proteins were expressed via baculovirus (bv) expression systems and were shown to have cytokine-dependent and antigen-specific biological activity. In the case of the IL-2 and IL-4 fusion proteins, covalent linkage of the cytokine in neuroantigen domains resulted in synergistic antigen presentation.

Fusion proteins as described herein may serve as antigen-specific tolerogens for treatment of autoimmune diseases. This novel concept for generation of tolerogenic vaccines was tested in some embodiments by constructing fusion proteins including a tolerogenic or biasing cytokine and the major encephalitogenic peptide of guinea pig myelin basic protein (GPMBP, i.e., neuroantigen or NAg). The cytokine domain was predicted to condition antigen presenting cells (APC) while simultaneously targeting the covalently linked encephalitogenic peptide to the MHCII antigen processing pathway of those conditioned APC. The rank order of tolerogenic activity in the Lewis rat model of autoimmune encephalomyelitis (EAE) was: NAgIL16>IL2NAg>IL1RA-NAg, IL13NAg≥IL10NAg, GPMBP, GP69-88, saline. NAgIL16 was also an effective inhibitor of EAE when administered after an encephalitogenic challenge during onset of clinical signs.

The antigen-targeting activity of fusion proteins described herein such as cytokine/NAg fusion proteins may be associated with mechanisms of tolerance induction. In some embodiments of the present invention, fusion proteins described herein were expressed including an N-terminal cytokine domain and a C-terminal neuroantigen (NAg) domain. In some embodiments, the cytokine domain included either rat IL-2 or IL-4, and the NAg domain included the dominant encephalitogenic determinant of guinea pig myelin basic protein (GPMBP). Subcutaneous administration of IL2NAg (IL2-neuroantigen) into Lewis rats either before or after an encephalitogenic challenge resulted in an attenuated course of EAE. In contrast, parallel treatment of rats with IL4NAg or NAg lacked tolerogenic activity. In the presence of IL-2R$^+$ MHCII$^+$ T cells, IL2NAg fusion proteins were at least 1,000 times more potent as an antigen than NAg alone. In particular embodiments, the tolerogenic activity of IL2NAg in vivo and the enhanced potency in vitro were both dependent upon covalent linkage of IL-2 and NAg. IL4NAg also exhibited enhanced antigenic potency. IL4NAg was approximately 100 fold more active than NAg alone in the presence of splenic APC. According to some embodiments, the enhanced potency of IL4NAg was related to the covalent linkage of cytokine and NAg and was blocked by soluble IL-4 or by a mAb specific for IL-4. The activities of IL2NAg revealed a potential relationship between NAg-targeting to activated T cells, T cell-mediated antigen presentation, and tolerance induction.

Accordingly, embodiments of the present invention provide compositions of matter for modulating an immune response and methods of modulating an immune response in a subject in need thereof.

Embodiments of the present invention further provide fusion proteins including an autoimmune antigen, an allergen antigen or an alloantigen or a portion thereof, and an anti-inflammatory cytokine or a portion thereof.

Embodiments of the present invention provide methods of making a fusion protein described herein.

Embodiments of the present invention provide an isolated nucleic acid encoding a fusion protein described herein as well as vectors including the isolated nucleic acids and hosts including the vectors.

Embodiments of the present invention provide compositions including at least one fusion protein including an autoimmune antigen, an allergen antigen or an alloantigen or a portion thereof, an anti-inflammatory cytokine or a portion thereof and a pharmaceutically acceptable carrier, excipient or diluent.

Embodiments of the present invention provide methods of regulating an immunological disorder including administering an effective amount of at least one fusion protein including an autoimmune antigen, an allergen antigen or an alloantigen or a portion thereof, and an anti-inflammatory cytokine or a portion thereof.

Embodiments of the present invention provide methods of modulating an immune response comprising administering at least one fusion protein in an amount sufficient to elicit a tolerogenic response, wherein the at least one fusion protein includes an autoimmune antigen, an allergen antigen or an alloantigen or a portion thereof, and an anti-inflammatory cytokine or a portion thereof.

Embodiments of the present invention provide methods of modulating antigen-presenting cell function including exposing an antigen-presenting cell to a fusion protein including an autoimmune antigen, an allergen antigen or an alloantigen or a portion thereof, and an anti-inflammatory cytokine or a portion thereof.

Embodiments of the present invention provide kits including one or more containers having pharmaceutical dosage units including an effective amount of a fusion protein or a portion thereof as described herein, wherein the container is packaged with optional instructions for the use thereof.

Embodiments of the present invention provide uses of the fusion proteins described herein for the preparation of a medicament for carrying out the utilities described herein.

Embodiments of the present invention further provide a novel approach for the induction of antigen-specific tolerance, for example, fusion proteins incorporating anti-inflammatory or tolerogenic cytokines and the dominant antigenic determinant of a self antigen (e.g. a neuroantigen (NAg) such as myelin basic protein (MBP)). The cytokine/NAg fusion proteins may target NAg to particular types of antigen-presenting cells (APC) by cytokine receptors present on the APC. The cytokine moiety of the fusion protein may modulate APC function to engender inhibitory or tolerogenic APC activities and also load the NAg into major histocompatibility complex (MHC) class II antigen processing pathways for presentation by the APC. NAg-specific T-helper cells that recognize NAg presented by the tolerogenic APC may be rendered nonresponsive or may differentiate into regulatory T cells. This approach may focus nonspecific inhibitory activities of particular cytokines onto rare NAg-specific T-helper cells that are responsible for CNS pathology.

The foregoing and other objects and aspects of the present invention are explained in greater detail in reference to the drawings and description set forth herein.

BRIEF DESCRIPTION OF THE DRAWINGS

FIG. 1. The generation of constructs encoding rat cytokine/enterokinase (EK)/GP73-87/6his fusion proteins. Panel (A): Overlapping primers 5A01 (SEQ ID NO:15) and 2F07 (SEQ ID NO:16) were extended to construct a DNA molecule encoding the C-terminal enterokinase (EK)/GP73-87/6his peptide (SEQ ID NO:3). Panel (B): This DNA molecule was fused by overlap extension PCR to the coding sequence for rat IL1-RA, IL-2, IL-4, IL-10, or IL-13. In each case, the cytokine gene encoded the N-terminal domain and the EK/GP/6his DNA encoded the C-terminal domain. The strategy to construct the coding sequence for the IL2NAg (IL2.7) fusion protein is shown in FIG. 1B. The PCR product encoding rat IL-2 and the extension product encoding the EK/GP73-87/6his tag were amplified in the presence of excess upstream (3B12) and downstream (2F07) primers to generate the intact fusion sequence.

FIGS. 2A and 2B. IL1RANAg fusion proteins inhibited IL-1 activity. Lewis rat thymocytes ($10^6$/well) were stimulated with 2.5 µg/ml Concanavalin A with or without 20 ng/ml of human IL-1β in the presence or absence of titrations (10%, 3.2%, 1%, or 0.3%; x-axis) of baculovirus supernatants containing the IL1RA/NAg4 fusion protein. Cells were pulsed with 1 µCi of [$^3$H]thymidine during the last 24 hrs of a 3 day culture. Mean cpm are shown in FIG. 2A, whereas the same data is portrayed as percent inhibition in FIG. 2B. Percent inhibition of IL-1 stimulated proliferation was defined as:

$$\left[1 - \frac{[[\text{mean cpm}(IL1) - \text{mean cpm(control)}]\text{with } IL1RA]}{[[\text{mean cpm}(IL1) - \text{mean cpm(control)}]\text{without } IL1RA]}\right] * 100\%.$$

Percent inhibition of Con A stimulated proliferation was defined as:

$$\left[1 - \frac{\text{mean cpm}(ConA \text{ with } IL1RA)}{\text{mean cpm}(ConA \text{ without } IL1RA)}\right] * 100\%.$$

Values for mean cpm were obtained from triplicate cultures. These data are representative of three separate experiments.

Figure 3:
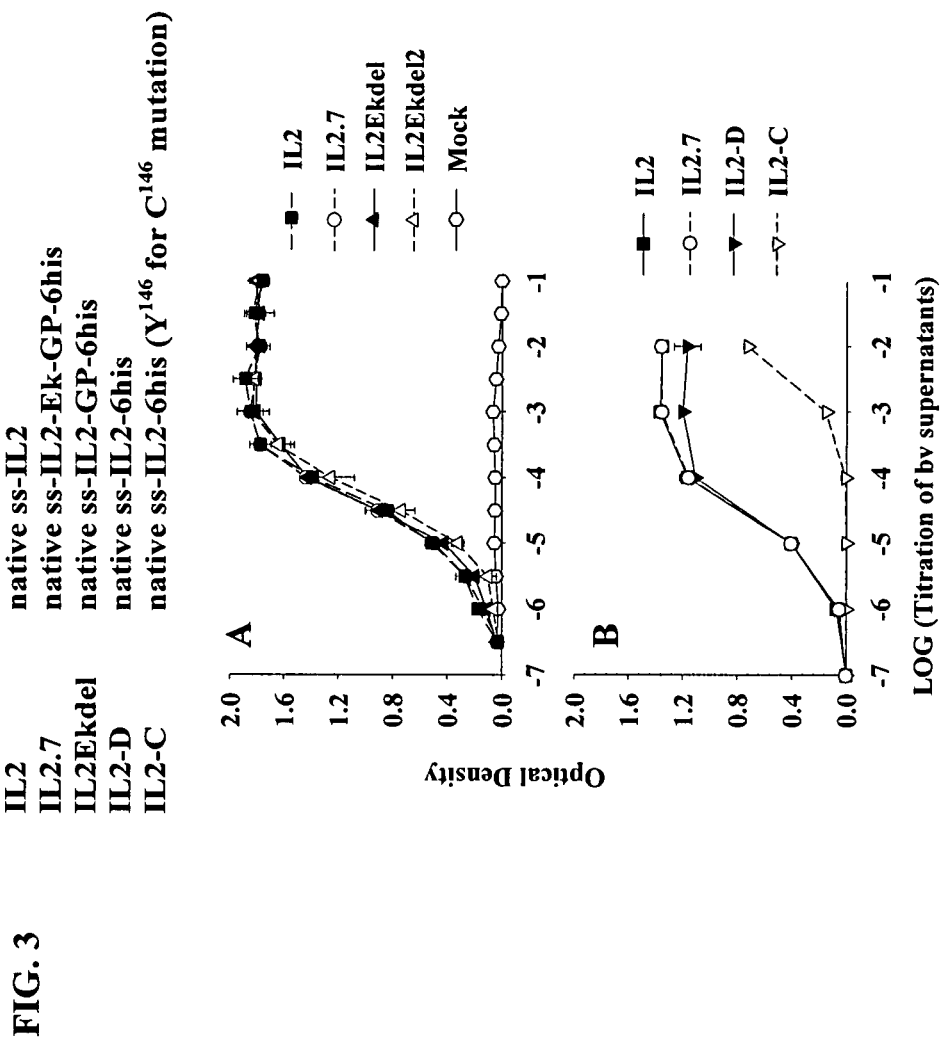

FIG. 3 (Panels A and B). The IL-2 fusion proteins presented IL-2 bioactivity: Five baculovirus systems were tested for expression of IL-2 bioactivity. Baculovirus supernatants containing the respective fusion proteins were titrated ($10^{-1}$ to $10^{-7}$; x-axis) and tested for IL-2 bioactivity in the presence of CTLL indicator cells ($10^4$/well). IL2Ekdel and IL2Ekdel2 represent sister baculovirus clones that express identical proteins. These data are representative of three separate experiments.

Figure 4:
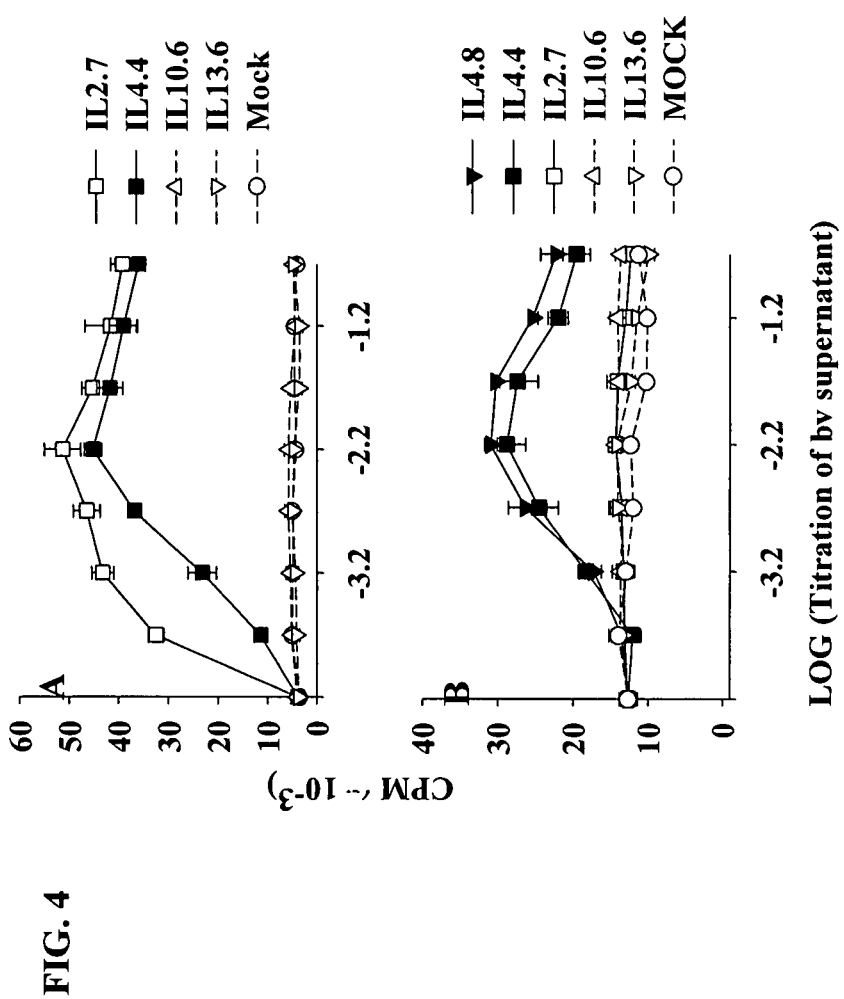

FIG. 4 (Panels A and B). The IL4.4 (IL4/EK/GP73-87/6his) fusion protein exhibited IL-4 bioactivity. Panel (A): Baculovirus expression systems IL2.7, IL4.4, IL10.6, and IL13.6 were tested for expression of mitogenic activity. Lewis rat thymocytes ($5 \times 10^5$/well) were cultured with 50 µg/ml PHA-P and 10 ng/ml IL-1β in the presence or absence of titrations (20% to 0.02%; i.e. $10^{-0.7}$ to $10^{-3.7}$; x-axis) of the respective baculovirus supernatant. (B) Designated baculovirus expression systems were tested for IL-4 mitogenic activity. Thymocytes ($10^6$/well) were cultured with 1 uM PMA and IL-2 (0.4% IL2 baculovirus supernatant) in the presence or absence of titrations ($10^{-0.7}$ to $10^{-3.7}$; x-axis) of the respective baculovirus supernatant. The IL2.7 baculovirus supernatant did not exhibit mitogenic activity in this assay because IL-2 was added in saturating concentrations to all wells. This bioassay was therefore specific for IL-4. These data are representative of three separate experiments.

FIGS. 5A, 5B and 5C. IL4 and IL13 fusion proteins inhibited γIFN-stimulated production of nitric oxide by macrophages. FIG. 5A: Rat NR8383 macrophages (Helmke et al. (1987) In Vitro Cell Dev Biol 23, 567-574; Patel et al. (1999) J Immunol 163, 5201-5210) ($5 \times 10^4$/well) were cultured with γIFN (100 U/ml), a fixed titration of the IL4.4 fusion protein (0.5% titration of baculovirus supernatant), and designated titrations of IL13.6 baculovirus supernatant (x-axis). FIG. 5B: Alternatively, γIFN-stimulated NR8383 macrophages were cultured with a fixed titration of the IL13.6 fusion protein (0.5% titration of baculovirus supernatant) and designated titrations of IL4.4 baculovirus supernatant (x-axis). FIG. 5C: NR8383 macrophages were cultured with γIFN (600 U/ml) and designated baculovirus supernatants (0.2% titration). These baculovirus supernatants were obtained from the $2^{nd}$ or $3^{rd}$ (P2 or P3) passage of the respective baculovirus in Sf9 insect cells. Nitric oxide production was measured by the accumulation of nitrite by use of the Griess reagent (Ding et al., 1988). These data are representative of three separate experiments.

FIGS. 6A, 6B, 6C and 6D. IL4 fusion proteins modulated T cell growth. The MBP-specific RsL.11 T cell clone ($10^5$/well, FIG. 6A) or the conalbumin-specific Conal.8D9 clone ($10^5$/well, FIG. 6B) were cultured with or without 1% titrations of designated baculovirus supernatants. Cells were pulsed with [$^3$H]thymidine during the last day of a 7-day culture. FIG. 6C: Thymocytes ($10^6$/well) were cultured with 1 uM PMA and IL-2 (0.4% IL2 baculovirus supernatant) in the presence or absence of titrations ($10^{-1}$ to $10^{-4}$; x-axis) of the respective baculovirus supernatant. Cells were pulsed with [$^3$H]thymidine during the last day of a 3-day culture. FIG. 6D: NR8383 macrophages were cultured with gamma-interferon (100 U/ml) in the presence or absence of designated baculovirus titrations. After 3 days of culture, supernatants were collected and assayed for evidence of nitric oxide production by the Griess reaction. These data are representative of three separate experiments.

Figures 7A, 7B:
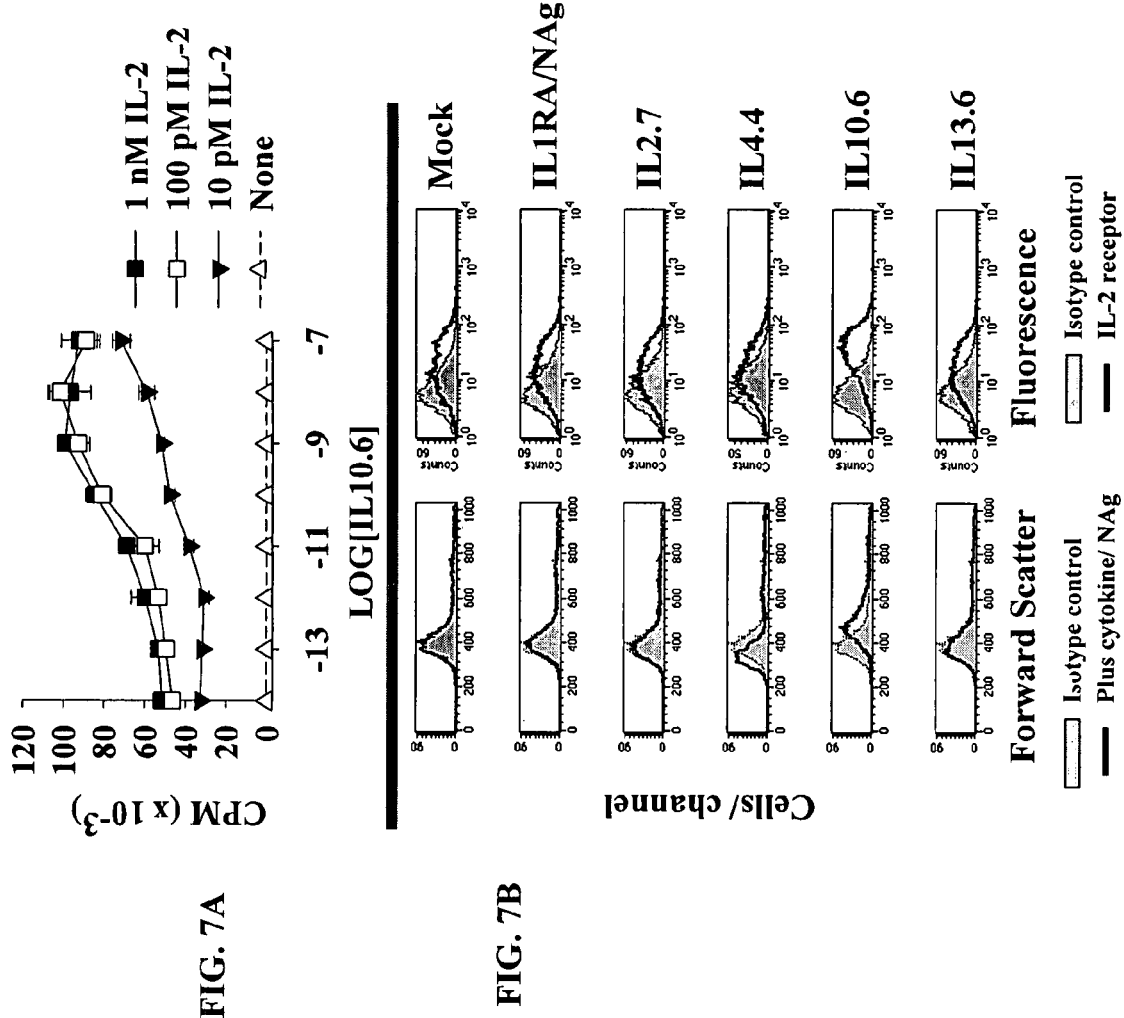

FIGS. 7A and 7B. The IL10.6 fusion protein enhanced IL-2R expression and IL-2 dependent T cell growth. FIG. 7A: MBP-specific RsL.11 T cells (25,000/well) were cultured with or without 10 pM, 100 pM, or 1 nM IL-2 and designated concentrations of purified IL10.6 (100 fM to 100 nM; x-axis). IL10.6 represents the IL10/Ek/NAg/6his fusion protein. Cells were pulsed with [$^3$H]thymidine during the last day of a 4-day culture. FIG. 7B: RsL.11 T cells ($5\times10^5$/well; 24-well plate) were cultured with IL-2 in the presence or absence of a 1% titration of designated baculovirus supernatants for 3 days. Cells were then analyzed by flow cytometry for cell size (left panels) or expression of the OX39 IL-2R (IL-2 receptor) marker (right panels). The OX6 IgG1 mAb exhibited staining equivalent to cells stained without primary Ab and was used as an isotype control. These data are representative of three separate experiments.

Figure 8:
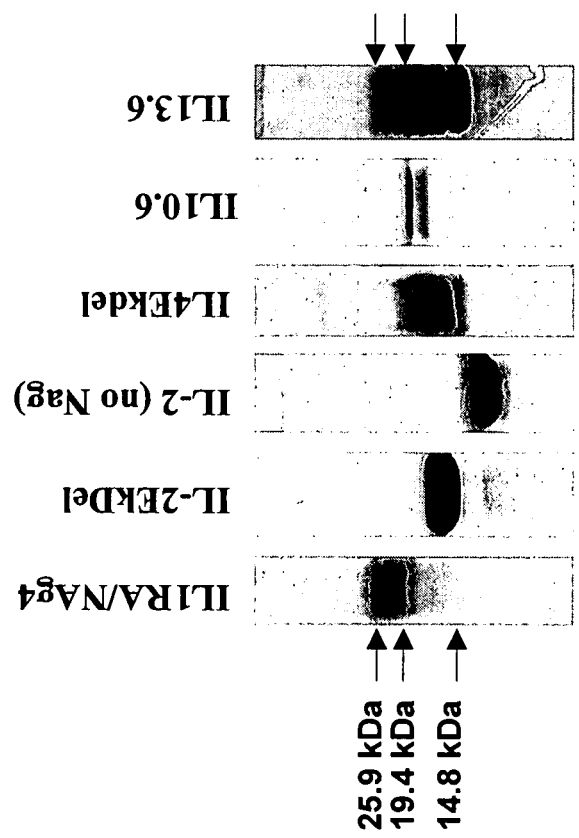

FIG. 8. SDS-PAGE analysis of purified cytokine/NAg fusion proteins. Proteins eluted from the Ni resin were analyzed on 12% SDS-PAGE gels. Lane 1, IL1RA/NAg with a predicted MW of 20,609 daltons and one potential N-linked site. Lane 2, IL2Ekdel with a predicted MW of 17,996 daltons and no potential N-linked sites. Lane 3, IL2-D with a predicted MW of 16,316 daltons and no potential N-linked sites. Lane 4, IL4Ekdel with a predicted MW of 16,654 daltons and four potential N-linked sites. Lane 5, IL10.6 with a predicted MW of 21,744 daltons and one potential N-linked site. Lane 6, IL13.6 with a predicted MW of 15,466 daltons and four potential N-linked sites. The image for each lane was obtained from independently performed SDS-PAGE analyses. These data are representative of three separate experiments.

Figure 9A:
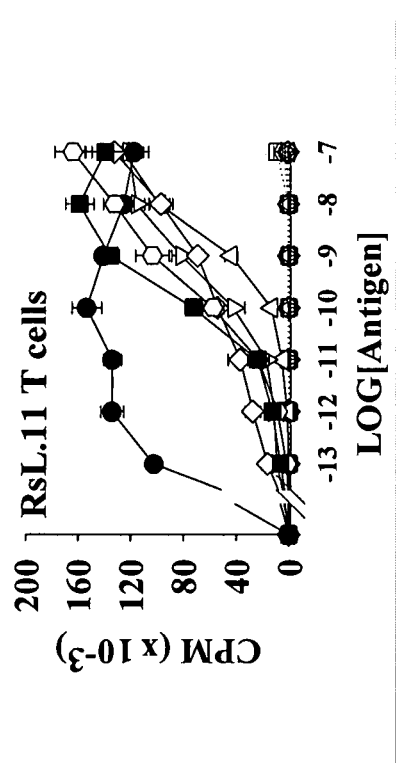
Figure 9B:
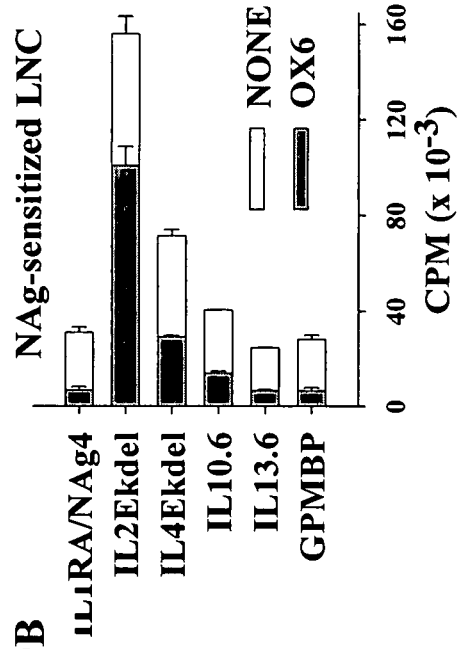

FIGS. 9A and 9B. Purified cytokine/NAg fusion proteins stimulated antigen-specific proliferation of MBP-specific T cells. FIG. 9A: RsL.11 T cells ($2.5\times10^4$/well) and irradiated splenocytes ($5\times10^5$/well) were cultured with designated concentrations of cytokine/NAg fusion protein or GPMBP in the presence or absence of a mAb (OX6) specific for rat MHC class II RT1B glycoproteins. In the presence of OX6, T cells cultured with 100 fM-10 nM cytokine/NAg exhibited <1,000 cpm, and T cells cultured with 100 nM cytokine/NAg exhibited <10,000 cpm of [$^3$H]thymidine incorporation. FIG. 9B: GPMBP-sensitized draining lymph node cells (LNC) were obtained 60 days after sensitization with DHFR/NAg in CFA. LNC ($5\times10^5$/well) were cultured with 100 nM cytokine/NAg or GPMBP in the presence or absence of OX6. Cells were pulsed with [$^3$H]thymidine during the last 24 hrs of a 3-day culture. These data are representative of three separate experiments.

Figures 10A, 10B:
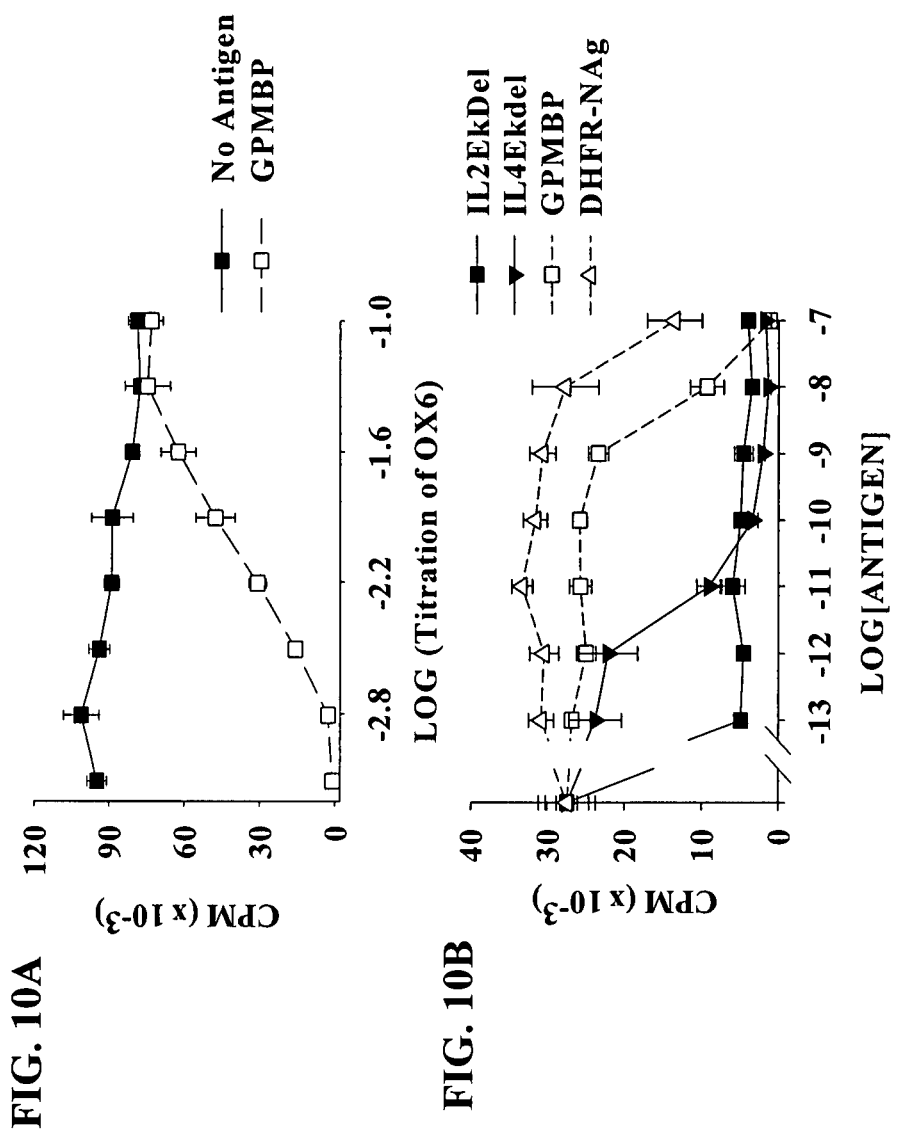

FIGS. 10A and 10B. Cytokine/NAg fusion proteins elicited antigen-specific killing during MHCII-dependent antigen presentation. FIG. 10A: MHCII$^+$ R1-trans T cells ($2.5\times10^4$/well) and irradiated RsL.11 T cells (1000 rads) were cultured with IL-2 (0.4% v/v IL2-D baculovirus supernatant) in the presence or absence of 1 uM GPMBP and designated titrations of OX6 (x-axis). FIG. 10B: MHCII$^+$ R1-trans T cells were starved of IL-2 for 24 hrs, were washed, and were cultured with designated concentrations of purified cytokine/NAg. After 24 hrs of culture, irradiated RsL.11 T cells ($2.5\times10^4$/well) and IL-2 were added to each well. Cultures were pulsed with [$^3$H]thymidine during the last 24 hrs of a 3-day culture. These data are representative of three separate experiments.

Figure 11:
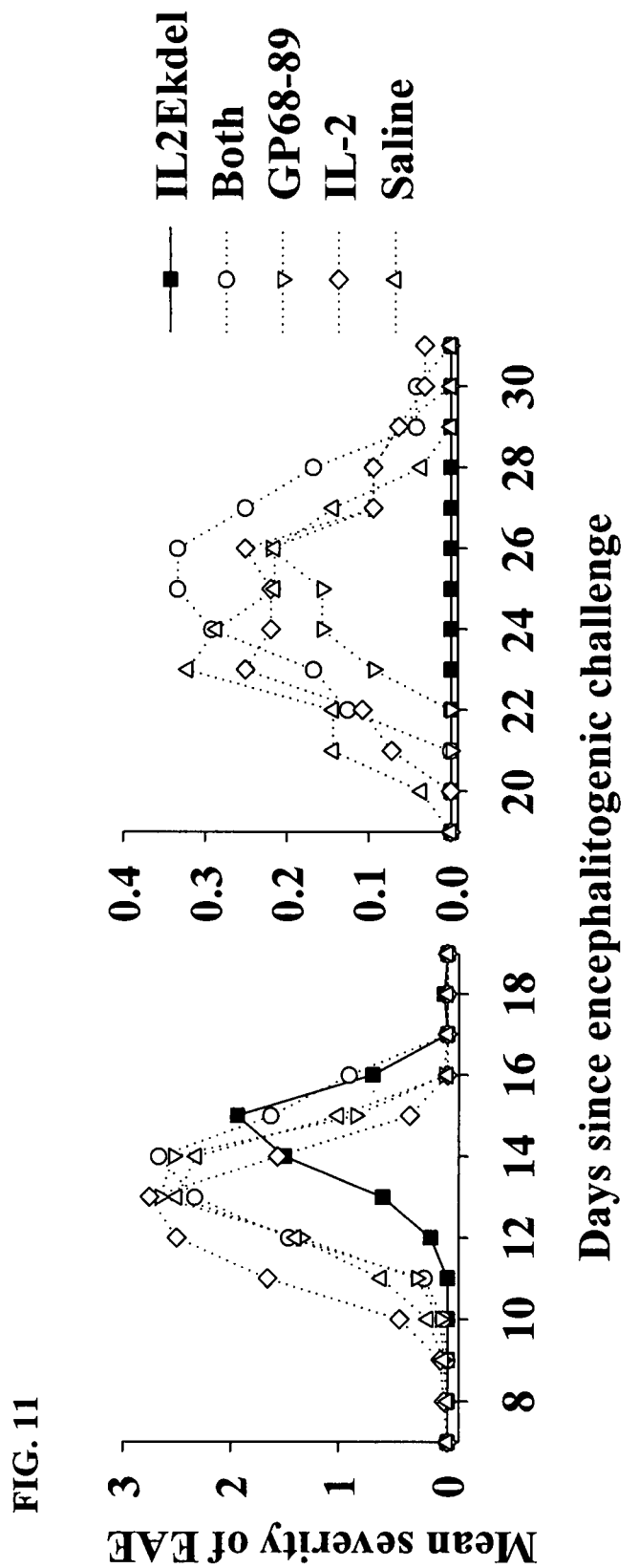

FIG. 11. Time course of EAE induction and relapse. FIG. 11 presents a graphical depiction of data shown in Experiment #2 of Table 6.

FIGS. 12A and 12B. Purified cytokine/NAg fusion proteins stimulated the antigenic proliferation of an MBP-specific T cell clone. FIG. 12A: RsL.11 T cells (25,000/well) and irradiated splenocytes (500,000/well) were cultured with designated concentrations of the respective fusion protein. FIG. 12B: RsL.11 T cells and irradiated splenic APC were cultured with designated concentrations of GPMBP, IL4.4, or IL2.7 in the presence or absence of the anti-rat I-A MHCII OX6 mAb or anti-rat I-E MHCII OX17 mAb. Cultures were pulsed with [$^3$H]thymidine during the last 24 hrs of a 72 hr culture. These data are representative of three experiments.

FIGS. 13A, 13B, 13C and 13D. Enhanced potency of IL4.4 and IL2.7 was dependent upon the covalent linkage of cytokine and NAg. FIGS. 13A and 13B: RsL.11 T cells (25,000/well) and irradiated splenocytes (500,000/well) were used to assay antigenic activity of the NAg. FIG. 13C: Thymocytes ($1\times10^6$/well) cultured with 1 uM PMA and rat IL-2 (0.4% baculovirus supernatant) were used to assay IL-4 activity. FIG. 13D: CTLL cells ($1\times10^4$/well) were used to assay IL-2 activity. (FIGS. 13A-D) These cells were cultured with or without designated concentrations of GPMBP, IL4.4, or IL2.7 in the presence or absence of IL-4 or IL-2 (1% or 0.1% baculovirus supernatants). Cultures were pulsed with [$^3$H]thymidine during the last 24 hrs of a 72 hr culture. These data are representative of three experiments.

Figure 14:
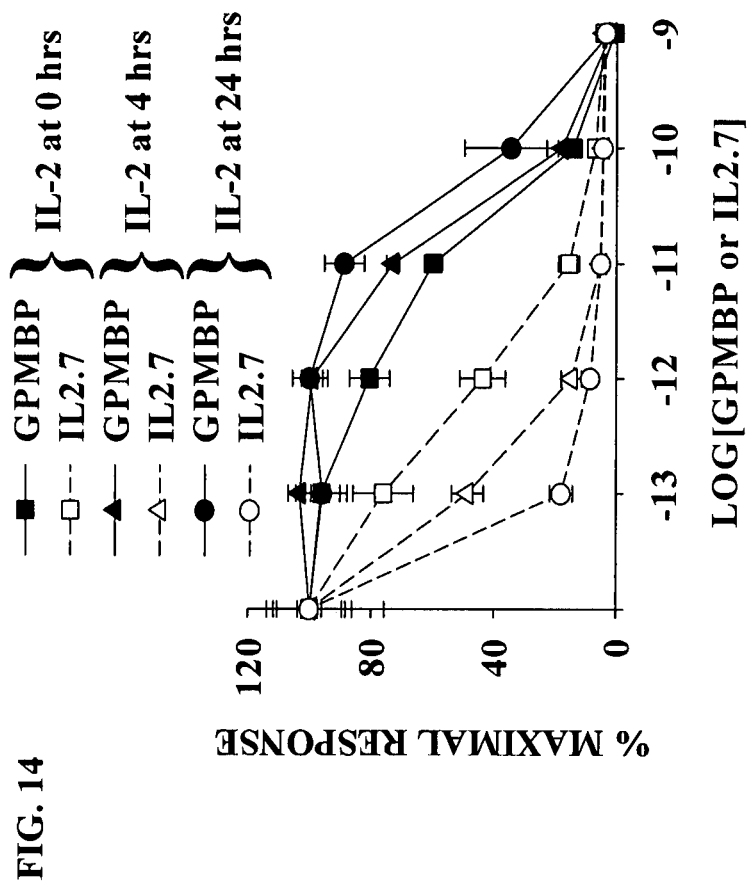

FIG. 14. T cell-mediated presentation of IL2.7 was inhibited by soluble IL-2. The MHCII$^+$ blastogenic R1-trans T cell clone was starved of IL-2 for 24 hours before the assay. At the initiation of the assay, R1-trans T cells were cultured with irradiated MBP-specific RsL.11 responders and designated concentrations of IL2.7 or GPMBP (x-axis). Rat IL-2 (0.4% of a baculovirus supernatant) was added at 0, 4, or 24 hours after initiation of culture. Cultures were pulsed with [$^3$H]thymidine during the last 24 hrs of culture of a 72 hr assay. These data are representative of three experiments.

Figure 15A:
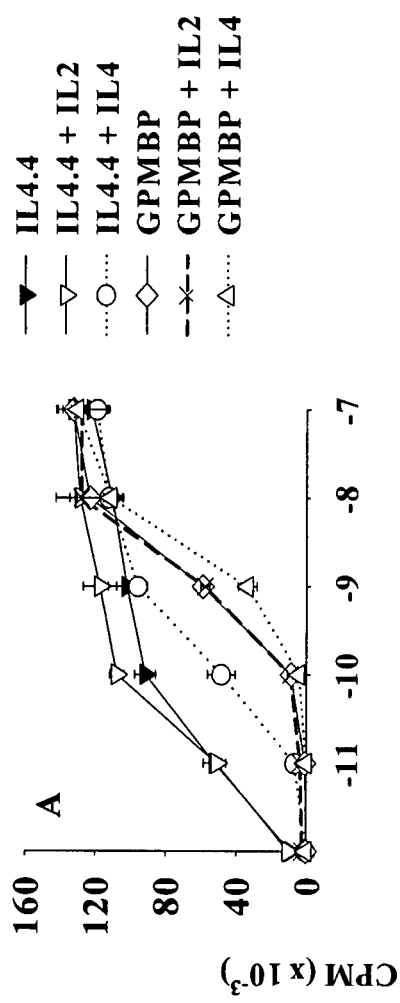
Figure 15B:
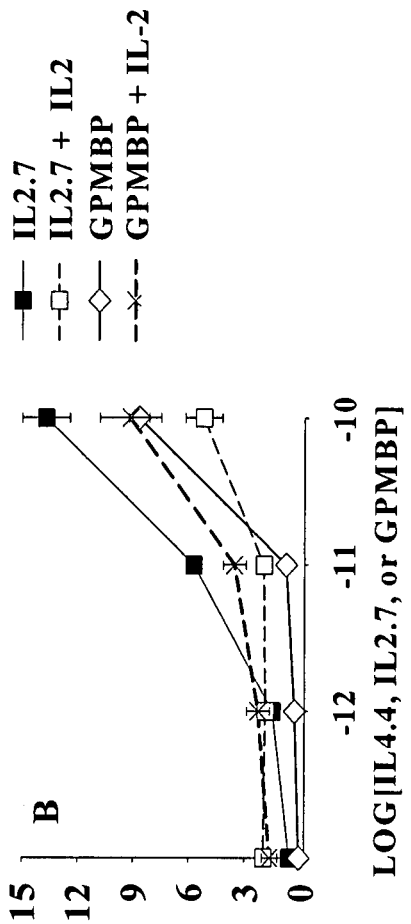

FIGS. 15A and 15B. In the presence of irradiated splenic APC, presentation of IL2.7 and IL4.4 were inhibited by IL-2 and IL-4, respectively. RsL.11 T cells and irradiated splenic APC were cultured for 3 days with designated concentrations of GPMBP, IL4.4, or IL2.7 in the presence or absence of 1% v/v baculovirus supernatant containing IL-2 or IL-4. IL-2 or IL-4 was added to culture 3 hr before antigen. Cultures were pulsed with [³H]thymidine during the last 24 hrs of a 72 hr culture. These data are representative of three experiments.

Figure 16:
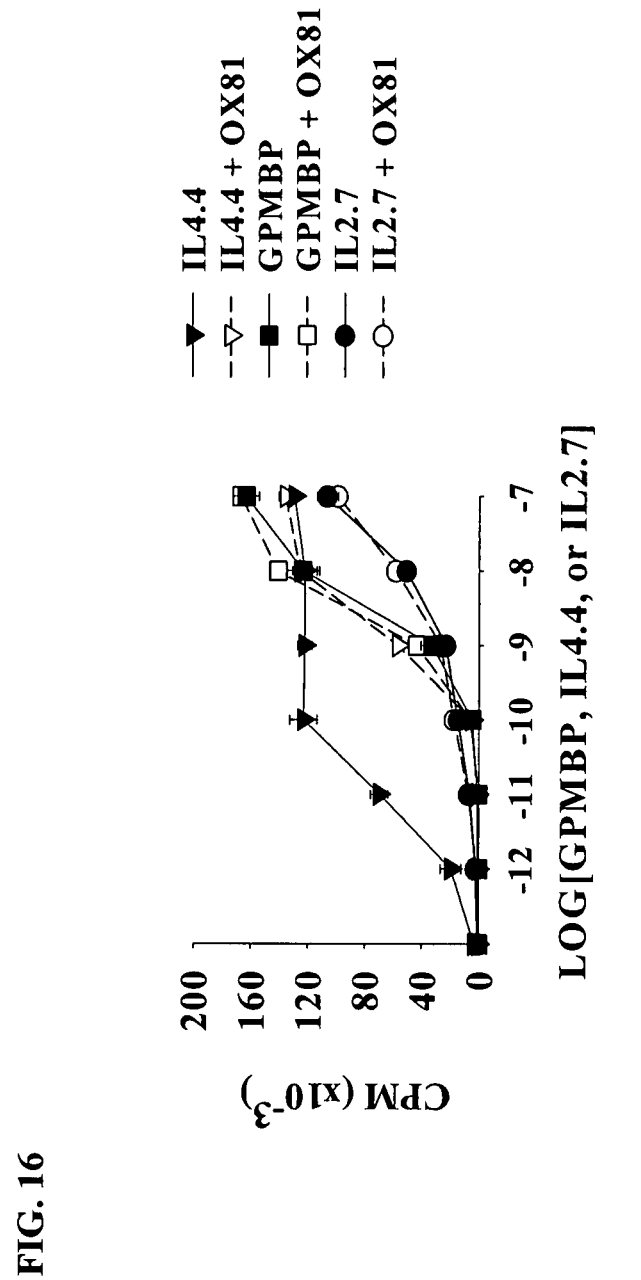

FIG. 16. IL4.4 and MBP are equally accessible to antigen processing. RsL.11 T cells and irradiated splenic APC were cultured for 3 days with designated concentrations of GPMBP, IL4.4, or IL2.7 in the presence or absence of the OX81 mAb against rat IL-4. The mAb were added to culture 3 hr before antigen. Cultures were pulsed with [³H]thymidine during the last 24 hrs of a 72 hr culture. These data are representative of three experiments.

Figure 17:
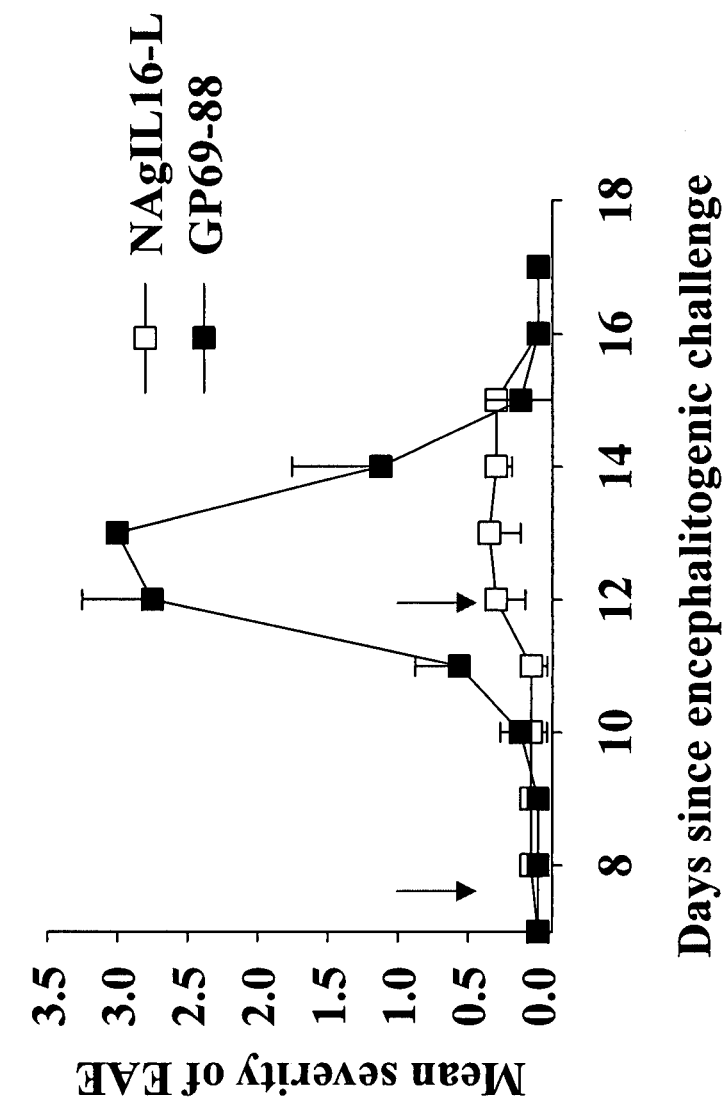

FIG. 17. The time course of the mean severity of experimental autoimmune encephalomyelitis (EAE) based on the data presented in Table 12.

Figure 18:
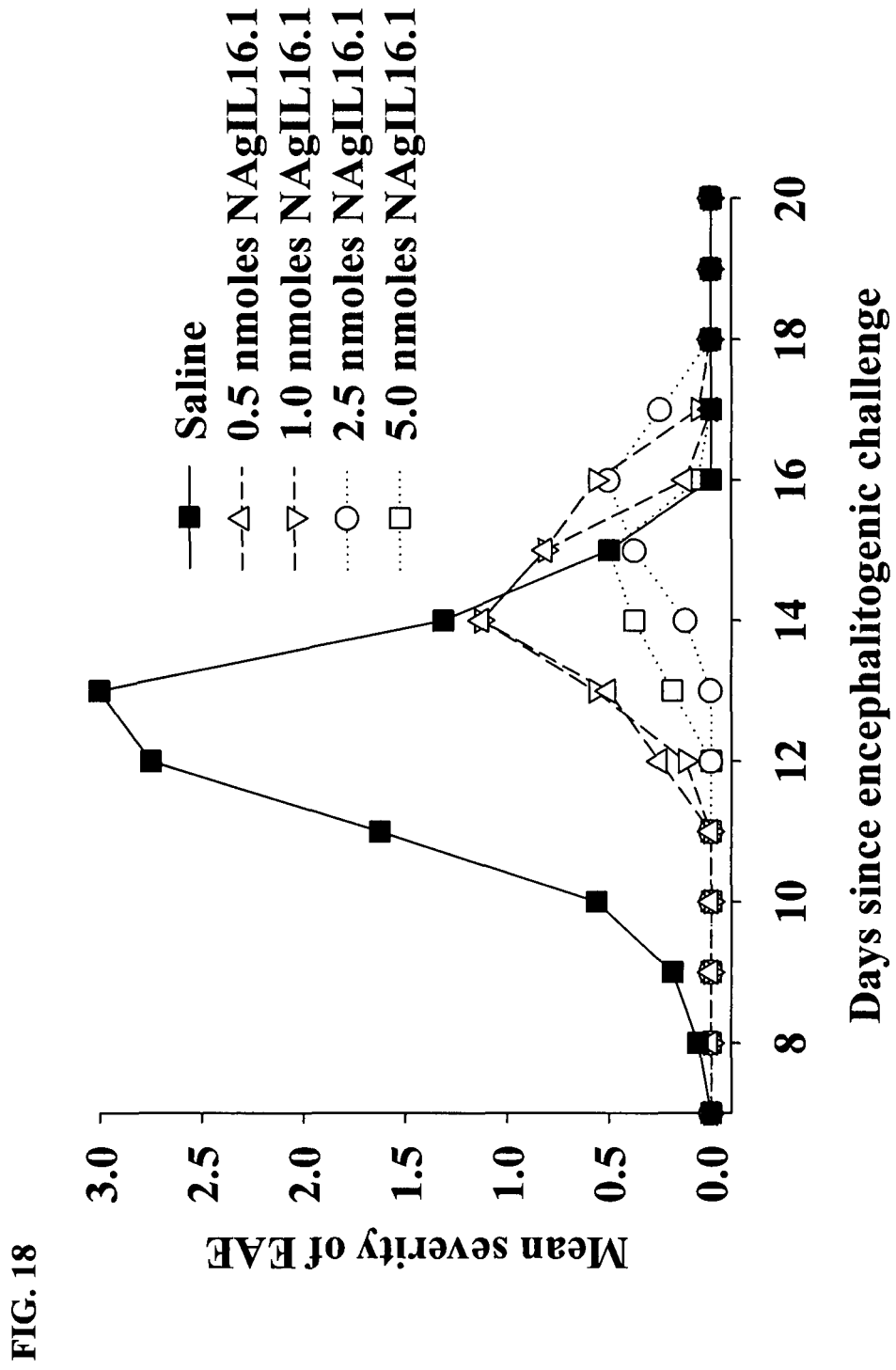

FIG. 18. Higher doses of NAgIL-16 L induced more efficient tolerance. Rats were injected with of designated doses NAgIL16 on days −21, −14, and −7 (n=4 for each group). Rats were then challenged with 50 μg DHFR-NAg in CFA on day 0. The mean cumulative score (p<0.01, p<0.01, p<0.05, p<0.05), the mean maximal intensity (p<0.01, p<0.01, ns, ns), and the mean day of onset (p<0.001; all groups) of rats treated with 0.5, 1.0, 2.5, or 5.0 nmoles NAgIL16-L differed significantly from the control group (saline), respectively.

Figure 19:
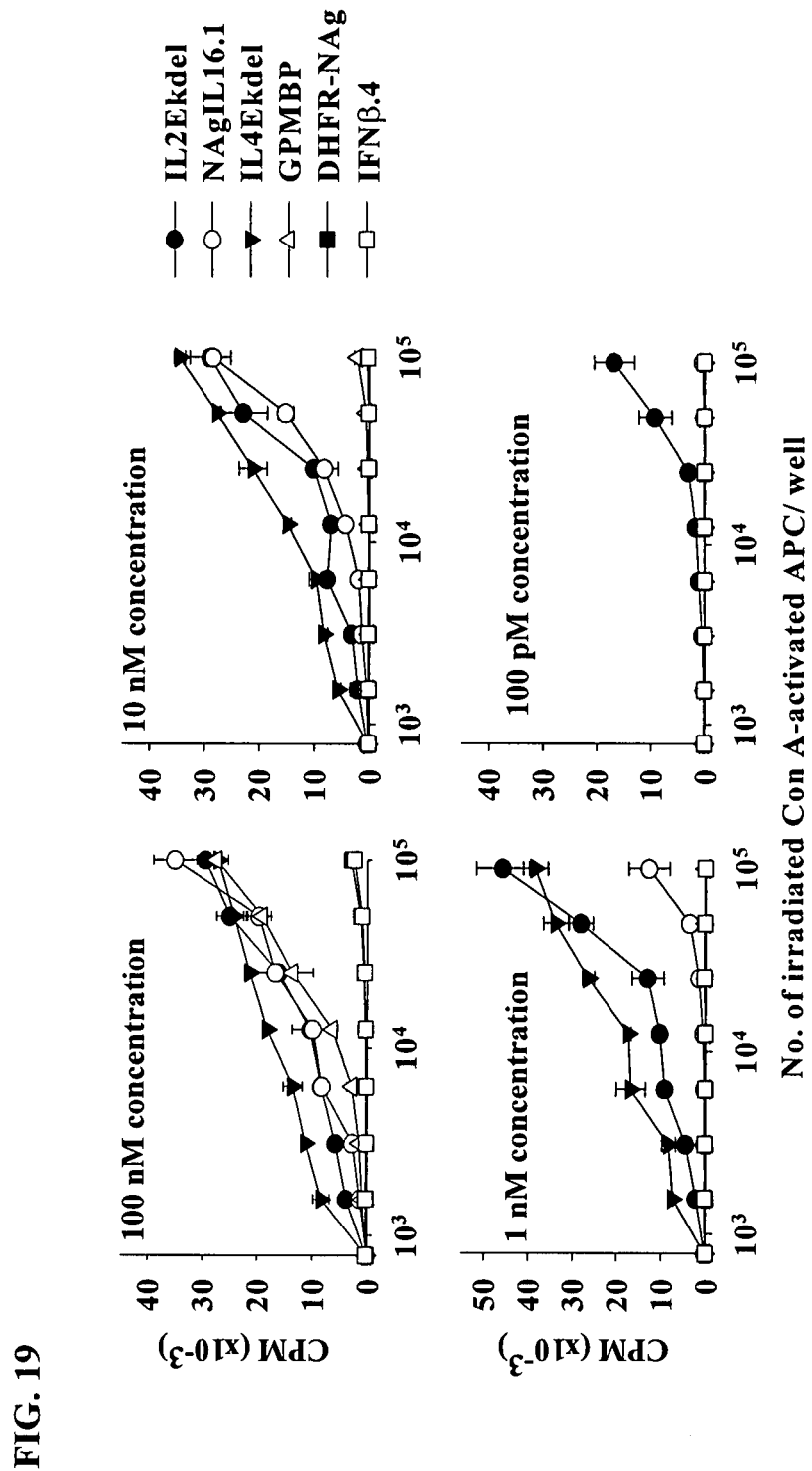

FIG. 19. NAgIL16 was targeted for presentation by non-adherent Con A-activated splenic T cells FIG. 20. Biological activity of IFNβNAg and IL2NAg fusion proteins.

Figure 21A:
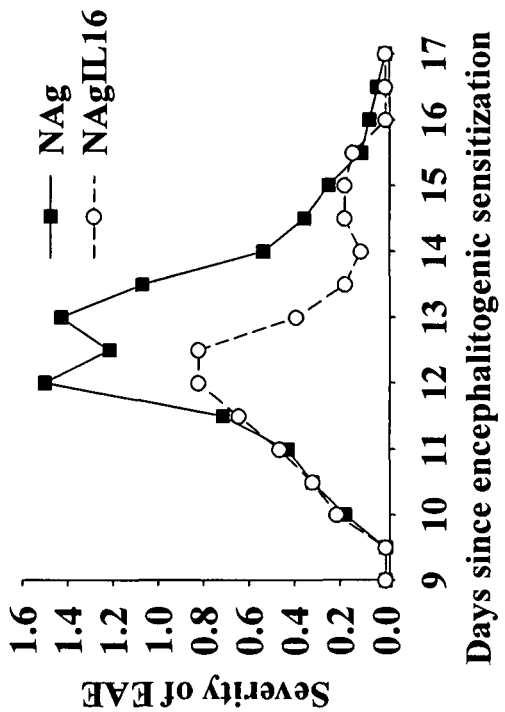
Figure 21B:
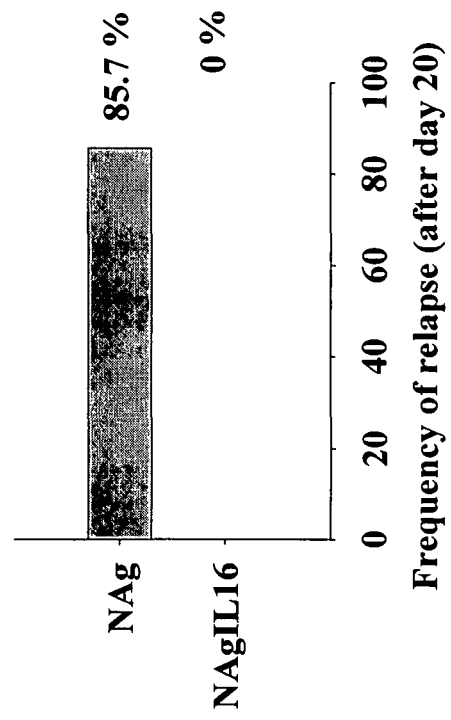

FIGS. 21A and 21B. Administration of NAgIL16 during clinical disease halts EAE progression and prevents subsequent relapse. Data presented in tabular form (Table 19, Experiment 2) are shown as a time course of EAE. On day 11, rats were matched for clinical signs of EAE and were randomly assigned to one of two groups that were injected with either NAg (GP69-88) or NAgIL16L. (FIG. 21A) Treatments were on day 11 (5 nmoles in saline i.v.), day 12 (5 nmoles in saline i.p.), and day 14 (2 nmoles in saline i.v.) (see arrows). The cumulative EAE severity per day for NAgIL16-treated rats was significantly less than that for NAg-treated rats on days 13, 13.5, and 14 (p=0.013, 0.005, and 0.009, respectively). The mean cumulative scores (tallied after the first treatment on day 11) also were significantly different (p<0.001) (Mann-Whitney Test). (FIG. 21B) The frequency of relapses (onset after day 21) for NAg-treated rats (6 of 7, 85.7%) was significantly higher than for NAgIL16-treated rats (0 of 7) (p=0.0047, Fisher's Exact Test).

DETAILED DESCRIPTION

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods can be used for the production of viral and non-viral vectors, manipulation of nucleic acid sequences, production of transformed cells, and the like according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, and other references mentioned herein are incorporated by reference in their entirety.

1. Definitions

As used herein, "a" or "an" or "the" can mean one or more than one. Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

The term "modulate," "modulates" or "modulation" refers to enhancement (e.g., an increase) or inhibition (e.g., a reduction) in the specified activity.

The term "regulate" as used herein refers to the ability to affect a method, process, state of being, disorder or the like. The effect may be that of prevention, treatment or modulation.

By the terms "treat," "treating" or "treatment of," it is intended that the severity of the disorder or the symptoms of the disorder are reduced, or the disorder is partially or entirely eliminated, as compared to that which would occur in the absence of treatment. Treatment does not require the achievement of a complete cure of the disorder.

By the terms "preventing" or "prevention", it is intended that the inventive methods eliminate or reduce the incidence or onset of the disorder, as compared to that which would occur in the absence of the measure taken. Alternatively stated, the present methods slow, delay, control, or decrease the likelihood or probability of the disorder in the subject, as compared to that which would occur in the absence of the measure taken.

A "therapeutically effective" or "effective" amount is intended to designate a dose that causes a relief of symptoms of a disease or disorder as noted through clinical testing and evaluation, patient observation, and/or the like. "Effective amount" or "effective" can further designate a dose that causes a detectable change in biological or chemical activity. The detectable changes may be detected and/or further quantified by one skilled in the art for the relevant mechanism or process. Moreover, "effective amount" or "effective" can designate an amount that maintains a desired physiological state, i.e., reduces or prevents significant decline and/or promotes improvement in the condition of interest. As is generally understood in the art, the dosage will vary depending on the administration routes, symptoms and body weight of the patient but also depending upon the compound being administered.

"Immune response" generally refers to innate and acquired immune responses including, but not limited to, both humoral immune responses (mediated by B lymphocytes) and cellular immune responses (mediated by T lymphocytes). An immune response may be beneficial and lead to immunity against infectious pathogens, or an immune response may be pathogenic and lead to autoimmune or hypersensitivity disease. Immune responses against foreign viruses, bacteria, fungi, parasites typically represent beneficial adaptive immune responses. Immune responses against self tissues, innocuous foreign objects (e.g., dust mite or pollen allergens, etc.), or tissue transplants represent examples of adverse maladaptive immune responses.

The term "antigen" as used herein means a substance or compound that stimulates an immune response. Although usually a protein or polysaccharide, antigens may be any type of molecule, which can include small molecules (haptens) that are coupled to a carrier-protein.

By the term "immunogenic" it is meant any substance or compound that stimulates an immune response.

By the term "tolerogen" it is meant any substance that stimulates immunological tolerance. By the terms "tolerogenic" or "tolerogenic activity" it is meant that a response of immunological tolerance is induced by an antigen or antigenic substance or an activity that results in the induction of immunological tolerance toward an antigen or antigenic substance.

The term "tolerance" as used herein refers to a decreased level of an immune response, a delay in the onset or progression of an immune response and/or a reduced risk of the onset or progression of an immune response. "Specific" immunological tolerance occurs when immunological tolerance is preferentially invoked against certain antigens in comparison with others. "Active" immunological tolerance refers to a state in which the tolerance effect(s) are the result of an ongoing biological process: for example, down-regulation of specific effector cells by suppressor cells. "Sustained tolerance" is tolerance that measurably persists for an extended period of time.

The terms "vaccination" or "immunization" are well-understood in the art. For example, the terms vaccination or immunization can be understood to be a process that increases a subject's immune reaction to antigen and therefore the ability to resist or overcome infection. In the case of the present invention, vaccination or immunization may decrease the recipient's immune response against self antigens thereby decreasing the likelihood of an autoimmune response.

"Polypeptide" as used herein, is used interchangeably with "protein," and refers to a polymer of amino acids (dipeptide or greater) linked through peptide bonds. Thus, the term "polypeptide" includes proteins, oligopeptides, protein fragments, protein analogs and the like. The term "polypeptide" contemplates polypeptides as defined above that are encoded by nucleic acids, are recombinantly produced, are isolated from an appropriate source, or are synthesized.

As used herein, a "functional" polypeptide is one that retains at least one biological activity normally associated with that polypeptide. Preferably, a "functional" polypeptide retains all of the activities possessed by the unmodified peptide. By "retains" biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits essentially no detectable biological activity normally associated with the polypeptide (e.g., at most, only an insignificant amount, e.g., less than about 10% or even 5%).

"Fusion protein" as used herein, refers to a protein produced when two heterologous nucleotide sequences or fragments thereof coding for two (or more) different polypeptides, or fragments thereof, are fused together in the correct translational reading frame. The two or more different polypeptides, or fragments thereof, include those not found fused together in nature and/or include naturally occurring mutants.

As used herein, a "fragment" is one that substantially retains at least one biological activity normally associated with that protein or polypeptide. In particular embodiments, the "fragment" substantially retains all of the activities possessed by the unmodified protein. By "substantially retains" biological activity, it is meant that the protein retains at least about 50%, 60%, 75%, 85%, 90%, 95%, 97%, 98%, 99%, or more, of the biological activity of the native protein (and can even have a higher level of activity than the native protein).

A "recombinant" nucleic acid is one that has been created using genetic engineering techniques.

A "recombinant polypeptide" is one that is produced from a recombinant nucleic acid.

As used herein, an "isolated" nucleic acid (e.g., an "isolated DNA" or an "isolated vector genome") means a nucleic acid separated or substantially free from at least some of the other components of the naturally occurring organism or virus, such as for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide. As used herein, the "isolated" polypeptide is at least about 25%, 50%, 60%, 70%, 75%, 80%, 85%, 90%, 95%, 97%, 98%, 99% or more pure (w/w).

A "heterologous nucleotide sequence" will typically be a sequence that is not naturally-occurring in the vector. Alternatively, a heterologous nucleotide sequence can refer to a sequence that is placed into a non-naturally occurring environment (e.g., by association with a promoter with which it is not naturally associated; in a cell that does not contain an endogenous form of the heterologous nucleotide sequence and/or under the direction of a promoter and/or other regulatory elements with which it is not normally associate, in a cell that does contain an endogenous form of the heterologous nucleotide sequence.).

There are no particular limits to the size of the heterologous nucleic acid. In particular embodiments, the heterologous nucleic acid is at least about 15, 18, 24, 50, 100, 250, 500, 1000, 1500, 2000, 3000, 4000 or more nucleotides long and/or less than about 4000, 3000, 2000, 1500, 1000, 500, 250 or 100 nucleotides long.

As used herein, a "vector" or "delivery vector" can be a viral or non-viral vector that is used to deliver a nucleic acid to a cell, tissue or subject.

A "recombinant" vector or delivery vector refers to a viral or non-viral vector that comprises one or more heterologous nucleotide sequences (i.e., transgenes), e.g., two, three, four, five or more heterologous nucleotide sequences. In an embodiment of the invention, the recombinant vectors and delivery vectors of the invention encode a fusion polypeptide of NAg and cytokines such as IL-2, IL-16 or IFN-β, but can also include one or more additional heterologous sequences, for example, sequences encoding C- or N-terminal modifications and linker moieties.

As used herein, the term "viral vector" or "viral delivery vector" can refer to a virus particle that functions as a nucleic acid delivery vehicle, and which comprises the vector genome packaged within a virion. Alternatively, these terms can be used to refer to the vector genome when used as a nucleic acid delivery vehicle in the absence of the virion.

A viral "vector genome" refers to the viral genomic DNA or RNA, in either its naturally occurring or modified form. A "recombinant vector genome" is a viral genome (e.g., vDNA) that comprises one or more heterologous nucleotide sequence(s).

As used herein, the term "host cell" comprises prokaryotic cells and eukaryotic cells. Exemplary prokaryotic host cells include *E. coli, Bacillus subtilis*, etc. Exemplary eukaryotic cells include yeast cells, insect cells, mammal cells, etc.

2. Active Agents

Embodiments of the present invention provide a fusion protein comprising, consisting essentially of or consisting of an autoimmune antigen or a portion thereof, and an anti-inflammatory cytokine or portion thereof. Embodiments of the present invention provide a fusion protein comprising, consisting essentially of or consisting of an allergen antigen (for example, antigens derived from common allergens that cause allergic hypersensitivity disease) or a portion thereof, and an anti-inflammatory cytokine or portion thereof. Embodiments of the present invention provide a fusion protein comprising, consisting essentially of or consisting of an alloantigen (e.g. an allogeneic tissue transplantation antigen) or a portion thereof, and an anti-inflammatory cytokine or portion thereof.

Autoimmune antigens of the present invention include neuroantigens (NAg) derived from the central or peripheral nervous system. In some embodiments, the neuroantigen is myelin basic protein (MBP) or a portion thereof. In other embodiments, the neuroantigen is proteolipid protein (PLP), myelin oligodendrocyte glycoprotein (MOG), myelin-associated oligodendrocytic basic protein, or other nervous system-derived proteins or a portion thereof. In some embodiments, the autoimmune antigen includes an encephalitogenic determinant of the myelin basic protein or a portion thereof. In other embodiments, the encephalitogenic determinant of the myelin basic protein includes amino acids of SEQ ID NO. 2. In general, the encephalitogenic determinant of neuroantigens include amino acid sequences of any self protein that may become the target of an encephalitogenic autoimmune attack. Further, as understood by one skilled in the art, the location of the encephalitogenic determinant can, in part, be determined by the highly polymorphic peptide binding properties of MHC class II glycoproteins.

Autoimmune antigens also include self-antigens such as insulin (autoimmune diabetes), the thyroid-stimulating hormone receptor (Grave's disease), platelets (thrombocytopenic purpura), neuromuscular junction (myasthenia gravis), red blood cells (autoimmune hemolytic anemia), intracellular antigens (spliceosomes, ribosomes, nucleic acid, etc in systemic lupus erythematosus). Autoimmune antigens can include any self molecule including protein, carbohydrate, lipid, or nucleic acid or any combination thereof that is made normally within the body that would constitute a part of the body that may become targeted in a particular autoimmune disease.

The anti-inflammatory cytokine is a naturally occurring or recombinant protein, analog thereof or fragment thereof that elicits an anti-inflammatory response in a cell that has a receptor for that cytokine. Cytokines of the present invention can include interleukin receptor antagonists from any species including murine and human such as IL-1-RA. Cytokines of the present invention can further include interleukins from any species including murine and human such as IL-1, IL-2, IL-3, IL-4, IL-5, IL-6, IL-7, IL-10, IL-12, IL-13, IL-14, IL-15, IL-16, IL-17 and IL-18, IL-19, IL-20, IL-21, IL-22, IL-23, IL-24, IL-25, IL-26, IL-27, IL-28A, IL-28B, IL-29, IL-31, IL-32, and IL-33, hematopoietic factors such as macrophage colony-stimulating factor (M-CSF), granulocyte-macrophage colony stimulating factor (GM-CSF), granulocyte colony stimulating factor (G-CSF) and erythropoietin, tumor necrosis factors (TNF) such as TNF-α and TGF-β, lymphokines such as lymphotoxin, regulators of metabolic processes such as leptin, interferons such as IFN-α, IFN-β, and IFN-γ and chemokines. In some embodiments of the invention, the cytokine is an interleukin such as IL-2, IL-16 or IFN-β. One or more of the fusion proteins of the present invention can display at least some cytokine biological activity.

According to embodiments of the present invention, the autoimmune antigen, the allergen antigen or the alloantigen and the anti-inflammatory cytokine are covalently linked. In some embodiments, the autoimmune antigen, the allergen antigen or the alloantigen and the anti-inflammatory cytokine are directly linked. In other embodiments, the autoimmune antigen, the allergen antigen or the alloantigen and the anti-inflammatory cytokine are linked through a linking moiety. The linking moiety can be an amino acid or peptide moiety. In some embodiments, the linking moiety is a cleavable linker. In particular embodiments, the linking moiety is an enterokinase domain.

Embodiments of the present invention further provide an isolated nucleic acid (e.g., an "isolated DNA" or an "isolated vector genome") that encodes the fusion protein described herein. The nucleic acid is separated or substantially free from at least some of the other components of the naturally occurring organism or virus, such as for example, the cell or viral structural components or other polypeptides or nucleic acids commonly found associated with the nucleic acid. The coding sequence for a polypeptide constituting the active agents of the present invention is transcribed, and optionally, translated. According to embodiments of the present invention, transcription and translation of the coding sequence will result in production of a fusion protein described. In some embodiments, the isolated nucleic acid encodes a cytokine, an interleukin receptor antagonist, an interleukin and/or a linker moiety to provide a fusion protein including a cytokine and an interleukin receptor antagonist or interleukin. In particular embodiments, the isolated nucleic acid encodes a fusion protein including NAg and IL-2, IL-16 or IFN-β as examples.

It will be appreciated by those skilled in the art that there can be variability in the nucleic acids that encode the fusion polypeptides of the present invention due to the degeneracy of the genetic code. The degeneracy of the genetic code, which allows different nucleic acid sequences to code for the same polypeptide, is well known in the literature (see Table 1).

Further variation in the nucleic acid sequence can be introduced by the presence (or absence) of non-translated sequences, such as intronic sequences and 5' and 3' untranslated sequences.

Moreover, the isolated nucleic acids of the invention encompass those nucleic acids encoding fusion proteins that have at least about 60%, 70%, 80%, 90%, 95%, 97%, 98% or higher amino acid sequence similarity with the polypeptide sequences specifically disclosed herein or to those known sequences corresponding to proteins included in aspects of the present invention (or fragments thereof) and further encode functional fusion proteins as defined herein.

As is known in the art, a number of different programs can be used to identify whether a nucleic acid or polypeptide has sequence identity or similarity to a known sequence. Sequence identity and/or similarity can be determined using standard techniques known in the art, including, but not limited to, the local sequence identity algorithm of Smith & Waterman (1981), *Adv. Appl. Math.* 2, 482, by the sequence identity alignment algorithm of Needleman & Wunsch (1970), *J. Mol. Biol.* 48, 443, by the search for similarity method of Pearson & Lipman (1988), *Proc. Natl. Acad. Sci. USA* 85, 2444, by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984), *Nucl. Acid Res.* 12, 387-395, preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, (1987) *J. Mol. Evol.* 35, 351-360; the method is similar to that described by Higgins & Sharp (1989), *CABIOS* 5, 151-153.

Another example of a useful algorithm is the BLAST algorithm, described in Altschul et al. (1990), *J. Mol. Biol.* 215, 403-410, and Karlin et al. (1993), *Proc. Natl. Acad. Sci. USA* 90, 5873-5787. A particularly useful BLAST program is the WU-BLAST-2 program which was obtained from Altschul et al. (1996), *Methods in Enzymology,* 266, 460-480. WU-BLAST-2 uses several search parameters, which are preferably set to the default values. The parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul et al., (1997) *Nucleic Acids Res.* 25, 3389-3402.

A percentage amino acid sequence identity value can be determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

To modify the amino acid sequences of the fusion proteins of the present invention, amino acid substitutions can be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding a polypeptide of the invention.

In making amino acid substitutions, the hydropathic index of amino acids can be considered. The importance of the hydropathic amino acid index in conferring interactive biologic function on a protein is generally understood in the art (see, Kyte and Doolittle (1982), *J. Mol. Biol.* 157:105; incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, Id.), and these are: isoleucine (+4.5); valine (+4.2); leucine (+3.8); phenylalanine (+2.8); cysteine/cystine (+2.5); methionine (+1.9); alanine (+1.8); glycine. (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Isolated nucleic acids of this invention include RNA, DNA (including cDNAs) and chimeras thereof. The isolated nucleic acids can further comprise modified nucleotides or nucleotide analogs.

The isolated nucleic acids encoding the polypeptides of the invention can be associated with appropriate expression control sequences, e.g., transcription/translation control signals and polyadenylation signals.

It will be appreciated that a variety of promoter/enhancer elements can be used depending on the level and tissue-specific expression desired. The promoter can be constitutive or inducible (e.g., the metalothionein promoter or a hormone inducible promoter), depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

The present invention further provides methods of making fusion proteins described herein. Methods of making fusion proteins are well understood in the art. According to embodiments of the present invention, methods of making fusion proteins include those in accordance with U.S. Pat. Nos. 4,701,416; 5,496,924; 5,521,288; 5,837,816; 5,981,221; 5,994,104; 6,109,885; 6,211,342; 6,211,427; 6,369,199; 6,482,409; 6,555,342; 6,972,322; 6,987,006 7,087,411 and 7,112,659 incorporated herein by reference in their entirety. Such methods include growing a host cell including a vector that includes nucleic acids encoding the fusion protein under conditions appropriate for expression and subsequent isolation of the fusion protein. Accordingly, the isolated nucleic acids encoding a polypeptide constituting the fusion protein of the invention can be incorporated into a vector, e.g., for the purposes of cloning or other laboratory manipulations, recombinant protein production, or gene delivery. Exemplary vectors include bacterial artificial chromosomes, cosmids, yeast artificial chromosomes, phage, plasmids, lipid vectors and viral vectors (described in more detail below).

In particular embodiments, the isolated nucleic acid is incorporated into an expression vector. In further embodiments of the present invention, the vector including the isolated nucleic acids described herein are included in a host cell. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a polypeptide of the invention or active fragment thereof operatively associated with the promoter, and, optionally, a termination sequence including a stop signal for RNA polymerase and a polyadenylation signal for polyadenylase.

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells or mammalian cells. Some suitable host cells are discussed further in Goeddel, *Gene Expression Technology*: Methods in Enzymology 185, Academic Press, San Diego, Calif. (1990). Examples of vectors for expression in yeast *S. cerevisiae* include pYepSec1 (Baldari et al., (1987) *EMBO J.* 6:229-234), pMFa (Kurjan and Herskowitz, (1982) *Cell* 30:933-943), pJRY88 (Schultz et al., (1987) *Gene* 54:113-123), and pYES2 (Invitrogen™, San Diego, Calif.). Baculovirus vectors available for expression of nucleic acids to produce proteins in cultured insect cells (e.g., Sf 9 cells) include the Bac-to-Bac® Baculovirus Expression System from Invitrogen.

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, adenovirus 2, cytomegalovirus and Simian Virus 40.

In addition to the regulatory control sequences discussed above, the recombinant expression vector can contain additional nucleotide sequences. For example, the recombinant expression vector can encode a selectable marker gene to identify host cells that have incorporated the vector and/or may comprise another heterologous sequence of interest.

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

3. Formulations and Administration

Embodiments of the present invention provide a composition including an autoimmune antigen, an allergen antigen or an alloantigen or a portion thereof and an anti-inflammatory cytokine or portion thereof, and a pharmaceutically acceptable carrier, excipient or diluent. In some embodiments, the composition includes at least two fusion proteins. In such embodiments, at least one fusion protein includes an anti-inflammatory cytokine or portion thereof that is different from the anti-inflammatory cytokine or portion thereof of at least one other fusion protein.

In terms of administration, the most suitable route in any given case will depend on the nature and severity of the condition being treated and on the fusion protein, viral vector, nucleic acid or pharmaceutical formulation being administered.

The fusion proteins, viral vectors and nucleic acids (e.g., DNA and/or RNA) of the invention can be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the fusion protein, viral vector or nucleic acid is typically admixed with, inter alia, an acceptable carrier. The carrier can be a solid or a liquid, or both, and is optionally formulated as a unit-dose formulation, which can be prepared by any of the well-known techniques of pharmacy.

The carriers and additives used for such pharmaceutical compositions can take a variety of forms depending on the anticipated mode of administration. Thus, compositions for oral administration may be, for example, solid preparations such as tablets, sugar-coated tablets, hard capsules, soft capsules, granules, powders and the like, with suitable carriers and additives being starches, sugars, binders, diluents, granulating agents, lubricants, disintegrating agents and the like. Because of their ease of use and higher patient compliance, tablets and capsules represent the most advantageous oral dosage forms for many medical conditions.

Similarly, compositions for liquid preparations include solutions, emulsions, dispersions, suspensions, syrups, elixirs, and the like with suitable carriers and additives being water, alcohols, oils, glycols, preservatives, flavoring agents, coloring agents, suspending agents, and the like.

In the case of a solution, it can be lyophilized to a powder and then reconstituted immediately prior to use. For dispersions and suspensions, appropriate carriers and additives include aqueous gums, celluloses, silicates or oils.

For injection, the carrier is typically a liquid, such as sterile pyrogen-free water, pyrogen-free phosphate-buffered saline solution, bacteriostatic water, or Cremophor EL[R] (BASF, Parsippany, N.J.), parenterally acceptable oil including polyethylene glycol, polyvinyl pyrrolidone, lecithin, arachis oil or sesame oil, with other additives for aiding solubility or preservation may also be included. For other methods of administration, the carrier can be either solid or liquid.

For oral administration, the fusion protein, viral vector or nucleic acid can be administered in solid dosage forms, such as capsules, tablets, and powders, or in liquid dosage forms, such as elixirs, syrups, and suspensions. The fusion protein, viral vector or nucleic acid can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges including the fusion protein, viral vector or nucleic acid in a flavored base, usually sucrose and acacia or tragacanth; and pastilles including the fusion protein, viral vector or nucleic acid in an inert base such as gelatin and glycerin or sucrose and acacia.

Formulations of the present invention suitable for parenteral administration can include sterile aqueous and non-aqueous injection solutions of the fusion protein, viral vector or nucleic acid, which preparations are generally isotonic with the blood of the intended recipient. These preparations can contain anti-oxidants, buffers, bacteriostats and solutes, which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets. For example, in one aspect of the present invention, there is provided an injectable, stable, sterile composition including a fusion protein, viral vector or nucleic acid of the invention, in a unit dosage form in a sealed container. Optionally, the composition is provided in the form of a lyophilizate, which is capable of being reconstituted with a suitable pharmaceutically acceptable carrier to form a liquid composition suitable for injection thereof into a subject.

Formulations suitable for rectal or vaginal administration can be presented as suppositories. These can be prepared by admixing the fusion protein, viral vector or nucleic acid with one or more conventional excipients or carriers, for example, cocoa butter, polyethylene glycol or a suppository wax, which are solid at room temperature, but liquid at body temperature and therefore melt in the rectum or vaginal cavity and release the fusion protein, viral vector or nucleic acid.

Formulations suitable for topical application to the skin can take the form of an ointment, cream, lotion, paste, gel, spray, aerosol, or oil. Carriers that can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3 (6):318 (1986)) and typically take the form of an optionally buffered aqueous solution. Suitable formulations comprise citrate or bis\tris buffer (pH 6) or ethanol/water.

The fusion protein, viral vector or nucleic acid can be formulated for nasal administration or otherwise administered to the lungs of a subject by any suitable means, for example, by an aerosol suspension of respirable particles including the fusion protein, viral vector or nucleic acid, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raebum et al. (1992) *J. Pharmacol. Toxicol. Methods* 27:143-159. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles including the fusion protein, viral vector or nucleic acid can likewise be produced with any solid particulate medicament aerosol generator, by techniques known in the pharmaceutical art.

Alternatively, one can administer the fusion protein, viral vector or nucleic acid in a local rather than systemic manner, for example, in a depot or sustained-release formulation.

In particular embodiments of the invention, administration is by subcutaneous or intradermal administration. Subcutaneous and intradermal administration can be by any method known in the art including, but not limited to, injection, gene gun, powderject device, bioject device, microenhancer array, microneedles, and scarification (i.e., abrading the surface and then applying a solution including the fusion protein, viral vector or nucleic acid).

In other embodiments, the fusion protein, viral vector or nucleic acid is administered intramuscularly, for example, by intramuscular injection or by local administration.

Nucleic acids (e.g., DNA and/or RNA) can also be delivered in association with liposomes, such as lecithin liposomes or other liposomes known in the art (for example, as described in WO 93/24640) and may further be associated with an adjuvant. Liposomes including cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. PCT publication WO 94/27435 describes compositions for genetic immunization including cationic lipids and polynucleotides. Agents that assist in the cellular uptake of nucleic acid, such as calcium ions, viral proteins and other transfection facilitating agents, may be included.

Polynucleotide immunogenic preparations may also be formulated as microcapsules, including biodegradable time-release particles. U.S. Pat. No. 5,151,264 describes a particulate carrier of phospholipid/glycolipid/polysaccharide nature that has been termed Bio Vecteurs Supra Moleculaires (BVSM).

According to the present invention, methods of this invention include administering an effective amount of a composition of the present invention as described above to the subject. The effective amount of the composition, the use of which is in the scope of present invention, will vary somewhat from subject to subject, and will depend upon factors such as the age and condition of the subject and the route of delivery. Such dosages can be determined in accordance with routine pharmacological procedures known to those skilled in the art. For example, the active agents of the present invention can be administered to the subject in an amount ranging from a lower limit from about 0.01, 0.05, 0.10, 0.50, 1.0, 5.0, or 10% to an upper limit ranging from about 10, 20, 30, 40, 50, 60, 70, 80, 90, 95, 96, 97, 98, 99, or 100% by weight of the composition. In some embodiments, the active agents include from about 0.05 to about 95% by weight of the composition. In other embodiments, the active agents include from about 0.05 to about 60% by weight of the composition. In still other embodiments, the active agents include from about 0.05 to about 10% by weight of the composition.

In particular embodiments of the present invention, the composition described herein is immunogenic. That is, the administration of the active agents can be carried out therapeutically (i.e., as a rescue treatment) or prophylactically. For example, in some embodiments, to protect against an autoimmune disease, subjects may be vaccinated in anticipation of antigen exposure, as neonates or adolescents. Adults that have not previously been exposed to the disease may also be vaccinated. The immunogenic composition of the present invention can be given as a single dose schedule or in a multiple dose schedule. A multiple dose schedule is one in which a primary course of administration may consist of about 1 to 10 separate doses, followed by other doses (i.e., booster doses) given at subsequent time intervals to maintain and/or reinforce the immune response, for example, at about 1 to 4 months for a second dose, and if needed, a subsequent dose(s) after another several months. The dosage regimen will also, at least in part, be determined by the need of the individual and be dependent upon the judgment of the medical or veterinary practitioner.

Embodiments of the present further provide kits comprising one or more containers having pharmaceutical dosage units including an effective amount of a fusion protein or portion thereof, wherein the container is packaged with optional instructions for the use thereof.

As described in further detail below, the present invention finds use in both veterinary and medical applications. Suitable subjects include avians, mammals and fish, with mammals being preferred. The term "avian" as used herein includes, but is not limited to, chickens, ducks, geese, quail, turkeys and pheasants. The term "mammal" as used herein includes, but is not limited to, primates (e.g., simians and humans), bovines, ovines, caprines, porcines, equines, felines, canines, lagomorphs, rodents (e.g., rats and mice), etc. Human subjects include fetal, neonatal, infant, juvenile and adult subjects.

4. Methods of Use

Embodiments of the present invention provide methods of regulating an immunological disorder including administering an effective amount of a fusion protein including an autoimmune antigen, an allergen antigen or an alloantigen or a portion thereof and an anti-inflammatory cytokine or portion thereof. In some embodiments, the method includes administering at least two fusion proteins that include an anti-inflammatory cytokine or portion thereof, wherein at least one fusion protein includes an anti-inflammatory cytokine or portion thereof that is different from that of at least one other fusion protein.

According to embodiments of the present invention, the immunological disorder includes autoimmune diseases, allergic or hypersensitivity diseases, transplant rejection, and tissue disorders.

Autoimmune diseases include, but are not limited to, those affecting the following organ systems. Nervous system: Acute disseminated encephalomyelitis (demyelinating inflammation following vaccination or infection); Myasthenia Gravis (anti-AchR antibodies, blockade of neuromuscular junction); Multiple sclerosis (inflammation of CNS myelin); Acute inflammatory demyelinating polyneuropathy/Guillain-Barre syndrome (inflammation of peripheral myelin); Endocrine system: Hashimoto's Thyroiditis (anti-thyroid antibodies, hypothyroidism); Grave's Disease (autoantibodies stimulate TSH receptors on thyroid follicular cells, hyperthyroidism); Insulin-Dependent Diabetes Mellitus (i.e. juvenile diabetes, inflammation and deletion of β islet cells); Autoimmune adrenal insufficiency (e.g. Addison's disease, inflammation coupled with progressive scarring and atrophy of adrenal glands); Autoimmune oophoritis (inflammation of ovaries, infertility); Autoimmune orchitis (inflammation of testis); Hematopoietic system: Autoimmune hemolytic anemia (anti-erythrocyte antibodies); Paroxysmal cold hemoglobinuria (mediated by IgM cold agglutinins against erythrocytes); Idiopathic thrombocytopenic purpura (anti-platelet antibodies, bleeding); Autoimmune neutropenia (antibodies against neutrophils cause degranulation, neutrophil depletion, and vasculitis); Pernicious anemia (progressive destruction of gastric fundic gland, loss of intrinsic factor, and malabsorption of vitamin $B_{12}$); Autoimmune coagulopathy (circulating anti-coagulants, anti-phospholipid antibody syndrome, neutralizes phospholipids necessary for clotting activity); Gastrointestinal Tract: Primary biliary cirrhosis (intrahepatic bile duct and portal inflammation leading to fibrosis and cirrhosis); Inflammatory bowel disease (Crohn's disease, ulcerative colitis); Kidney: Glomerulonephritis (antibody against glomerular basement membrane); Immune complex glomerular nephritis (accumulation of deposited immune complexes in basement membrane); Skin: Pemphigus vulgaris (loss of adhesion between epidermal cells, blistering, antibody against stratified squamous epithelium); Systemic autoimmune disease: Systemic Lupus Erythematosus (arthralgias, rash, nephritis, anti-nuclear antibodies); Rheumatoid Arthritis (inflammatory polyarticular arthritis, rheumatoid factor); Sjogren's syndrome (inflammation of lacrymal and parotid glands with arthritis); Polymyositis (inflammation of skeletal muscle); Dermatomyositis (inflammation of skin and skeletal muscle); Scleroderma (progressive systemic sclerosis, sclerosis of skin and internal organs); and Cardiac and vascular diseases: Autoimmune myocarditis (inflammation of cardiac muscle); Immune complex-mediated vasculitis (passive deposition of immune complexes in vessel walls followed by C-mediated lysis and inflammation); Polyarteritis nodosa (type of necrotizing vasculitis that follows certain types of infections). In some embodiments of the present invention, the autoimmune disease is an autoimmune disease affecting the nervous system, endocrine system, hematopoietic system, gastrointestinal tract, renal system, cardiac system, vascular system, musculoskeletal system or a combination thereof. In some embodiments, the autoimmune disease is a systemic autoimmune disease. In particular embodiments, the autoimmune disease is multiple sclerosis.

Allergic or hypersensitivity diseases include, but are not limited to, allergic rhinitis, asthma, atopic dermatitis, allergic gastroenteropathy, contact dermatitis, drug allergy or a combination thereof. In particular embodiments, the present invention provides active agents, compositions and methods to induce antigen-specific immunological tolerance to allergens responsible for the allergic diseases described herein.

Transplant rejection and tissue disorders include, but are not limited to, those affecting the kidney, liver, pancreas, heart, lung, bone, skin and combinations thereof. In particular embodiments, the present invention provides compositions and methods to induce antigen-specific immunological tolerance to allogeneic and xenogeneic transplantation antigens that may contribute to the rejection of tissue transplants, and thus, facilitate acceptance of kidney transplants, liver transplants, pancreas transplants, skin grafts, heart transplants, and heart-lung transplant. The active agents and methods may also alleviate complications of bone marrow transplantation (i.e., graft versus host disease).

It is contemplated that diseases and/or disorders treated by the methods of this invention can include any disease or disorder that can be treated by mounting an effective tolerogenic response to a fusion protein of the invention. Accordingly, embodiments of the present invention provide methods of modulating an immune response including administering a fusion protein in an amount sufficient to elicit a tolerogenic response. In some embodiments, the immune response is antigen-specific. In some embodiments, the administering step is carried out in vivo or ex vivo. In still other embodiments, the tolerogenic response is an active tolerance mechanism. In particular embodiments, the tolerogenic response is a sustained tolerogenic response.

It is also contemplated that the compositions of this invention can be used as a vaccine or prophylactic composition and employed in methods of preventing a disease or disorder in a subject, comprising administering to the subject an effective amount of the active agent of this invention. The vaccine can be administered to a subject who is identified to be at risk of contracting a particular disease or developing a particular disorder and in whom the ability to elicit an immune response to an antigen may be impaired. Identification of a subject at risk can include, for example, evaluation of such factors as family history, genetic predisposition, age, environmental exposure, occupation, lifestyle and the like, as are well known in the art.

The effective dosage of any specific active agent will vary somewhat from composition to composition, patient to patient, and will depend upon the condition of the patient and the route of delivery. As a general proposition, a dosage from about 0.1 to about 50 mg/kg will have therapeutic efficacy, with still higher dosages potentially being employed for oral administration, wherein aerosol administration is usually lower than oral or intravenous administration. Toxicity concerns at the higher level may restrict intravenous dosages to a lower level such as up to about 10 mg/kg, all weights being calculated based upon the weight of the active base, including the cases where a salt is employed. Typically a dosage from about 0.5 mg/kg to about 5 mg/kg will be employed for intravenous or intramuscular administration. A dosage from about 10 mg/kg to about 50 mg/kg may be employed for oral administration.

In particular embodiments, administration to a subject such as a human, a dosage of from about 0.01, 0.1, or 1 mg/kg up to 50, 100, or 150 mg/kg or more for each active agent can be employed. Depending on the solubility of the particular formulation of active agents administered, the daily dose can be divided among one or several unit dose administrations.

Having now described the invention, the same will be illustrated with reference to certain examples, which are included herein for illustration purposes only, and which are not intended to be limiting of the invention.

EXAMPLES

Example 1

Methods of Making Exemplary Fusion Proteins

A. Recombinant Protein Design

The structural design of the fusion proteins are shown in Table 2. A strategy of overlap extension PCR was used to construct genes encoding a given cytokine fused by a cleavable linker (an enterokinase domain) with the dominant encephalitogenic sequence of guinea pig myelin basic protein (GPMBP) and a C-terminal 6-histidine sequence. For example, IL1RA/NAg4 consisted of the native IL1RA signal sequence (ss), the full length IL1-RA cytokine, a GDDDDKG (SEQ ID NO:1) enterokinase (EK) domain, the encephalitogenic peptide of GPMBP (PQKSQRSQDEN-PVVH, SEQ ID NO:2), and a 6-his C-terminal tag. The IL2.7, IL4.4, IL10.6, and IL13.6 constructs were based on a parallel design. The encephalitogenic peptide was the 73-87 sequence of GPMBP (GP73-87). The numbering system for this peptide of GPMBP was based on accession P25188. The upstream and downstream primers used for amplification of the entire cytokine/NAg fusion gene contained 5' Spe I and Kpn I restriction endonuclease sites, respectively.

Several other fusion proteins were also used as controls (Table 2). Baculovirus expression systems for rat IL-2 and IL-4 were described previously (Norris et al. (2001) Cell Immunol 211, 51-60; Mannie et al. (2003) Immunol Cell Biol 81, 8-19). These proteins consisted of the native rat cytokine without N- or C-terminal modifications. The IL2Ekdel and IL4Ekdel constructs were generated via a mutagenesis reaction that deleted the DNA sequence encoding the EK domain from the recombinant IL2.7 and IL4.4 pFastbac1 vectors. These proteins consisted of the native IL-2 or IL-4 cytokine fused directly to the GP73-87 peptide and included the adjoining C-terminal 6his tag. The IL2-D, IL2-C, IL4-A, IL13-A, IL13-B proteins consisted of the native cytokine directly fused to a C-terminal 6his tag. These latter proteins lacked the Ek-NAg sequence and thereby served as relevant comparisons to assess the function of the NAg domain in cytokine/NAg fusion proteins. Primers (Table 3) were designed based on DNA sequences for rat cytokines IL-1RA (Eisenberg et al. (1991) Proc Natl Acad Sci USA 88, 5232-5236) (accession NM_022194), IL-2 (McKnight et al. (1989) Immunogenetics 30, 145-147) (M22899), IL-4 (McKnight et al. (1991) Eur J Immunol 21, 1187-1194) (X16058), IL-10 (Feng et al. (1993) Biochem Biophys Res Commun 192, 452-458) (NM_012854), and IL-13 (Lakkis et al. (1993) Biochem Biophys Res Commun 197, 612-618) (L26913).

B. RNA Isolation, cDNA Synthesis, Overlap Extension PCR of Cytokine/NAg Constructs Lewis rat splenocytes ($3 \times 10^6$/ml) were activated in complete RPMI with 2.5 μg/ml Con A and 10 μg/ml LPS for 24 hours. Total RNA was purified by use of the TRIzol® Reagent (Invitrogen). Rat cytokine cDNA was synthesized in the presence of 200 nM downstream primer (3' primers, see Table 3), 1 μg total RNA, first strand buffer, dNTP, DTT, and either SuperScript II RNase H—Reverse Transcriptase or SuperScript III Reverse Transcriptase (Invitrogen) according to manufacturer's instructions in a total volume of 20 μl. To amplify the cytokine gene, 10 μl of the RT product was mixed with 100 nM upstream primer (5' primers) and Platinum Taq DNA Polymerase High Fidelity (Invitrogen) together with PCR mix, MgSO$_4$, and dNTP. The downstream primer was carried over in the RT product at a final concentration of 100 nM. The PCR cycle was 94° C. 1', 59° C. 1', and 68° C. 1' for 39 cycles followed by a final 68° C.-8' extension step. The PCR products were washed 3 times with H$_2$0 by use of Microcon YM100 Centrifugal Filter Devices.

To generate the neuroantigen, 100 nM 5A01 primer and 100 nM 2F07 primer were mixed and extended with Platinum Pfx DNA polymerase (Invitrogen) in the presence of PCR buffer, MgSO$_4$, and dNTP according to manufacturer's instructions. The PCR cycle was 94° C. 1', 62° C. 1', and 68° C. 5' for 10 cycles followed by a final 68° C.-10' extension step. The resulting DNA encoded the following peptide sequence: DDDDKGPQKSQRSQDENPVVHHHHHH (SEQ ID NO:3) and included a Kpn I endonuclease restriction site. This overlap extension reaction is portrayed in FIG. 1, Panel A. The DDDDK (SEQ ID NO:4) sequence represents an enterokinase cleavage site and the 15mer sequence PQKSQRSQDENPVVH (SEQ ID NO:2) represents the dominant encephalitogenic region of guinea pig myelin basic protein. To generate the IL2NAg, IL4NAg, IL10NAg, IL13NAg cytokine/NAg fusion constructs, 1/20 dilution of cytokine PCR product (2 μl) was mixed with a 1/20 dilution of the NAg PCR product (2 μl), 200 nM of respective upstream primer, and 200 nM of the 2F07 downstream primer, and the reactants were amplified by the Platinum Pfx DNA polymerase. The overlap extension PCR used to generate the IL2.7 (IL2NAg) construct is diagramed in FIG. 1, Panel B. The PCR cycle was 94° C. 1', 57° C. 1', and 68° C. 2' for 39 cycles followed by a final 68° C.-10' extension step.

To generate the IL1RANAg fusion construct, 10 μl of the respective RT product was mixed with 200 nM of 3B05 upstream primer together with 100 nM 5A01 and 200 nM 2F07 primer. In this reaction, the 5A02 downstream primer was carried over in the RT product at a final concentration of 100 nM. In the latter reaction, the cytokine, the NAg, and the cytokine/NAg construct were amplified in a single PCR reaction catalyzed by Platinum High Fidelity Taq DNA Polymerase.

To generate the IL2Ekdel construct, the IL2.7 pFastbac1 plasmid was used as template for a whole plasmid PCR in the presence of the 5H04 and 6E12 primers and Platinum Pfx DNA polymerase. 5H04 was the mutagenic primer that lacked the coding sequence for the EK domain. This primer and the 6E12 primer were overlapping primers that generated linearized copies of the plasmid. To generate the IL4Ekdel construct, the IL4.4 pFastbac1 plasmid was used as template for a whole plasmid PCR in the presence of the 5H05 and 6F01 primers. The 5H05 primer was mutagenic by virtue of lacking the coding sequence for the EK linker. In both of the IL2Ekdel and IL4Ekdel reactions, the reaction mix was melted at 95° C. for 5' followed by 29 cycles at 94° C. for 30", 60° C. for 1', 68° C. for 3' followed by a 68° C. 10' extension step. The products were washed and concentrated by use of Microcon YM100 Centrifugal Filter Devices, were treated with Dpn I restriction endonuclease to deplete residual IL2.7 and IL4.4 parental plasmids, and were used to transform Top10 *E coli* by electroporation. Colonies bearing recombinant pFastbac1 plasmids with deletion of the EK coding region were identified by restriction digestion of purified plasmids and analysis on 1.5% agarose gels. Deletion of the EK coding region in the respective plasmids was verified by DNA sequencing of the cytokine-NAg-6his fusion gene.

To generate the IL2woNAg (IL2-D, IL2-C), IL4woNAg (IL4-A), and IL13woNAg (IL13-A, IL13-B) constructs, purified IL2.7, IL4.4, and IL13.6 plasmids were used as templates, and PCR reactions were run with upstream primers 3B12, 2D11, or 2E01 and downstream primers 6H02, 6H04, and 6H06, respectively (Table 3). The latter three primers had a 5'-Kpn I restriction together with the coding region for the 6his tag and the 5' sequence of the cytokine gene. The coding region for the EK-NAg sequence was deleted from these downstream primers. These PCR products thereby contained sequences encoding the respective cytokine with a 6his C-terminal tag. These PCR products were cut with Spe I and Kpn I restriction endonucleases and were cloned into the pFastbac1 vector for generation of recombinant baculovirus.

C. Derivation of Baculovirus Expression Systems

The IL1RANAg (636 bp), IL2NAg (570 bp), IL4NAg (543 bp), IL10NAg (639 bp), and IL13NAg (495 bp) PCR fusion products exhibited the sizes predicted for each fusion construct. The PCR products were purified on a 1% TAE agarose gel, and DNA was extracted from gel slices by use of Amicon Ultrafree DA Units. PCR products were washed 3 times with $H_2O$ by use of Microcon YM100 Centrifugal Filter Devices. These PCR products were digested with SpeI and KpnI restriction endonucleases (Invitrogen) for 4 hrs at 37° C. according to manufacturer's instructions. Digests were heat-inactivated at 70° C. for 10' and extensively washed by use of Microcon YM100 Centrifugal Filter Devices. Likewise, purified pFastBac1 plasmid (Invitrogen) was digested with Spe I and Kpn I, was purified on a 1% TAE agarose gel, and then extensively washed with Microcon YM100 devices.

To ligate insert DNA into the vector, 90 fmoles of cytokine/NAg DNA were mixed with 30 fmoles of vector plasmid in the presence of T4 DNA ligase for 1 hr at room temperature. Ligation mixes were then used to transform Top10 *E. coli* by electroporation. Colonies exhibiting growth in the presence of 100 μg/ml ampicillin were grown in minicultures. Plasmids were purified, digested with Spe I and Kpn I, and assessed for the appropriate sized inserts on 1.5% agarose gels. Plasmids bearing the appropriate sized inserts were subject to forward and reverse DNA sequencing to verify the predicted sequence of the fusion gene.

Purified recombinant pFastBac1 plasmids were used to transform electrocompetent DH10BAC *E. coli* to facilitate site-specific transposition of the respective expression cassettes into a baculovirus shuttle vector according to modified protocols of the Bac-to-Bac Baculovirus Expression System (Invitrogen). White/blue selection facilitated identification of recombinant DH10BAC colonies. Bacmid DNA containing the recombinant baculovirus shuttle vector was purified and used to transfect Sf9 insect cells according to the manufacturer's protocol. Establishment of recombinant baculovirus was confirmed by the appearance of an infected morphology of Sf9 insect cells in 3-7 day cultures. The presence of recombinant baculovirus were verified by PCR analysis for the presence of the respective cytokine/NAg DNA. Recombinant baculovirus were also verified by the presence of cytokine and NAg activity in supernatants of infected Sf9 cells.

D. Confirmation of Recombinant Baculovirus

A standard bioassay was used to analyze supernatants of P1 (passage #1) baculovirus stocks for the presence of secreted fusion proteins. The bioassay measured whether titrations of the P1 supernatants had antigenic activity. The presence of the NAg domain in the supernatants was measured by the antigen-dependent proliferation of the MBP-specific RsL.11 T cell clone. That is, supernatants from infected Sf9 cultures were titrated in complete RPMI medium followed by the addition of RsL.11 T cells (25,000/well) and irradiated splenic antigen presenting cells (500,000/well). After 2 days of culture, cultures were pulsed with 1 μCi of [$^3$H]thymidine and were harvested after an additional 24 hr of culture. Antigen-specific proliferation was assessed by [$^3$H]thymidine incorporation in triplicate or quadruplicate cultures.

E. Purification of Recombinant Baculovirus

Titrations of baculovirus infected Sf9 supernatant from $10^{-4}$ to $10^{-9}$ were added to Sf9 cells ($10^4$ cells/well in 96 well flat bottomed plates) in Sf900 II SFM medium. Each titration was added to approximately 24 separate wells. In 7-10 days, wells were visually inspected for the presence of an infected cellular morphology, and cultures showing limiting dilution growth of baculovirus was identified as those that likely originated from a single baculovirus particle. Baculovirus supernatants (10 μl) were transferred to replicate plates containing RsL.11 T cells (25,000/well) and irradiated splenocytes (500,000/well). T cell proliferation was measured by [$^3$H]thymidine incorporation. Titrations exhibiting limiting dilution growth of baculovirus and high levels of antigenic activity were harvested and used at a titration of 1/2000 to infect new Sf9 cultures to establish purified baculovirus stocks. These baculovirus stocks were then used to support protein expression experiments.

F. Purification of Fusion Proteins

To purify fusion proteins, baculovirus supernatants were concentrated on YM10 ultrafiltration membranes and then subjected to two consecutive affinity chromatography steps. The first affinity chromatography step was described in (Blank et al. (2002) Protein Expr Purif 24, 313-322) and was based on a plasmid generously provided by Drs. Peter Lindner and Andreas Pluckthun. This plasmid encoded a single chain Fv anti-6his antibody fused to two tandem chitin-binding domains (scFv-CBD2). After expression in E. coli, bacterial lysates were passed through 1 ml of chitin resin column by gravity flow. This step enabled purification of the scFv-CBD2 protein via binding of the tandem chitin binding domains to the chitin bead resin. Thus, the anti-6his single chain antibody was immobilized onto chitin columns and was used to purify recombinant proteins bearing C-terminal 6-histidine tags from concentrated baculovirus supernatants. These affinity chromatography columns were stored in TBST buffer (50 mM TrisHCl, 500 mM NaCl, 0.1 mM EDTA, 1% Triton X-100, 0.1% Na azide, pH 8.0). After equilibration in MBS buffer (20 mM MES, 500 mM NaCl, 0.1 mM EDTA, pH 6.5), concentrated baculovirus-infected Sf9 supernatants were passed through the column to trap the cytokine/NAg fusion protein. Interactions of the scFv-CBD2 with 6his-tagged proteins were stable in weak acids (pH5.5) but were disrupted in basic solutions (pH~10), and cytokine/NAg proteins were eluted in CAPS buffer (50 mM CAPS, 500 mM NaCl, 0.1 mM EDTA, pH 10.0). The second affinity chromatography step involved direct loading of the chitin column eluate onto nickel columns (Qiagen) followed by extensive washing of the Ni resin (50 mM NaH$_2$PO$_4$, 500 mM NaCl, 10 mM imidazole, pH 8.0) and elution with 250 mM imidazole (pH 8.0) or by acid elution (pH 4.0). Protein quantity was assessed by the BCA protein assay (Pierce) and purity was assessed by SDS-PAGE.

Example 2

Biological Activity a. Animals and Reagents

Lewis rats were bred and maintained at East Carolina University School of Medicine. Care and use of experimental animals was performed in accordance with institutional guidelines. GPMBP was purified from guinea pig spinal cords (Rockland). OX6 anti-I-A (RT1B) IgG1, OX17 anti-1-E (RT1D) IgG1 (McMaster and Williams. (1979) Immunological Reviews 47, 117-137), OX39 anti-IL2Ralpha IgG1 (Paterson et al. (1987) Mol Immunol 24, 1281-1290) were concentrated by ultrafiltration of B cell hybridoma supernatants through Amicon spiral wound membranes (100 kDa exclusion). Hybridomas were obtained from the European Collection of Cell Cultures. FITC-conjugated goat anti-mouse IgG1 reagents were purchased from Southern Biotechnology (Birmingham, Ala.). The domain structures of cytokine/NAg fusion proteins used in this study are shown in Table 2. The synthetic peptide GP69-88 (YGSLPQKSQR-SQDENPVVHF) was obtained from Quality Controlled Biologicals, Inc. (Hopkinton, Mass.).

B. Cell Lines and Culture Conditions

The RsL.11 MBP-specific clone was derived from Lewis rats sensitized with rat MBP in CFA. The R1-trans T cell clone was a transformed, IL-2 dependent line that constitutively expressed MHCII, B7.1, and B7.2 (Patel et al. (1999) J Immunol 163, 5201-5210; Mannie and Norris (2001) Cell Immunol 212, 51-62). The GP2 line and the derivative GP2.3H3.16 clone was derived from Lewis rats sensitized with GPMBP (Mannie et al. (1998) Cell Immunol 186, 83-93; Walker et al. (1999) J Leukoc Biol 66, 120-126). Assays were performed in complete RPMI medium [10% heat-inactivated fetal bovine serum (Summit, Boulder, Colo.), 2 mM glutamine, 100 μg/ml streptomycin, 100 U/ml penicillin (Whittaker Bioproducts, Walkersville, Md.), 50 uM 2-ME (Sigma)]. T cell lines were propagated in complete RPMI supplemented with recombinant rat IL-2 (0.4% v/v Sf9 supernatant). Con A (Sigma-Aldrich, St. Louis, Mo.) was used at a final concentration of 2.5 μg/ml.

C. Proliferative Assays

Cultures were pulsed with 1 μCi of [$^3$H]thymidine (6.7 Ci/mmol, New England Nuclear) after 48 hours of a 3-day assay. Cultures were harvested onto filters by use of a Tomtec Mach III harvester. [$^3$H]thymidine incorporation into DNA was measured by use of a Wallac 1450 Microbeta Plus liquid scintillation counter. Error bars represent standard deviations of triplicate or quadruplet sets of wells.

D. Measurement of IL-2 and Nitric Oxide

To measure IL-2 bioactivity, CTLL cells ($10^4$ cells/100 μl complete RPMI/well) were cultured with designated supernatants for 48 hours, and 10 μl of a MTS/PMS solution [2.9 mg/ml MTS (Promega) and 0.1 mg/ml PMS (Sigma)] were added to each well. Plates were read the next day at 492 nm on an Anthos ELISA Reader (ACCSales, Chapel Hill, N.C.). Antigen-stimulated IL-2 production was calculated as the mean OD values from experimental cultures minus the mean OD values from control unstimulated cultures. The production of nitric oxide was measured by formation of the stable decomposition product nitrite in cell-free supernatants (50 μl) after mixing with an equal volume of the Griess reagent (Ding et al (1988) J Immunol 141, 2407-2412).

E. Flow Cytometric Analysis

T cells were incubated with a 1/20 titration of a concentrated supernatant containing OX6, OX17, or OX39 IgG1 mAb for 45 minutes at 4° C. The cells were washed two times and were incubated for 45 minutes with FITC-conjugated goat anti-mouse IgG1 reagents. Dead cells were excluded from analysis by forward versus side scatter profiles. Data were acquired with a Becton Dickinson FACScan flow cytometer and were analyzed with the CELLQuest software program.

F. Tolerance Induction

To determine whether cytokine/NAg proteins prevent active induction of experimental autoimmune encephalomyelitis (EAE) in Lewis rats, rats were given a total of three subcutaneous injections of a given cytokine/NAg protein. A dose of 0.5 to 1 nmole of cytokine/NAg was delivered during each injection at 1-2 week intervals as designated. The cytokine/NAg proteins were either solubilized in saline or were emulsified in alum. At least 7 days after the last injection, rats were challenged with NAg in Complete Freund's adjuvants (CFA) (day 0) to induce EAE.

G. Induction and Clinical Assessment of EAE

EAE was induced in Lewis rats by injection of an emulsion containing 25 or 50 µg GPMBP in CFA (200 µg *Mycobacterium tuberculosis*). In designated experiments, rats were challenged with an emulsion containing 50 µg of the DHFR-NAg fusion protein in CFA. DHFR-NAg was comprised of the mouse dihydrofolate reductase as the N-terminal domain and the encephalitogenic GP69-87 peptide of GPMBP as the C-terminal domain. The emulsion (total volume of 0.1 ml per rat) was injected in two 0.05 ml volumes on either side of the base of the tail. The following scale was used to assign intensity of EAE; paralysis in the distal tail, 0.25; limp tail, 0.5; ataxia, 1.0; hind leg paresis, 2.0; full hind leg paralysis, 3.0. The cumulative score for each rat consisted of the sum of daily scores for each animal. The mean cumulative score for a group was calculated by averaging the cumulative scores for all rats within a group. The mean maximal intensity scores were assigned to each group based on the average maximum score among afflicted rats within a group.

H. Lewis Rat T Cells

The RsL.11 T cell and the R1-trans clone were described previously (Mannie and Norris. (2001) Cell Immunol 212, 51-62). T cells were assayed in complete RPMI medium and were maintained in same medium supplemented with recombinant rat IL-2. The complete RPMI 1640 medium consisted of 10% heat-inactivated fetal bovine serum, 2 mM glutamine, 100 µg/ml streptomycin, 100 U/ml penicillin (Whittaker Bioproducts, Walkersville, Md.), and 50 µM 2-ME (Sigma). Rat IL-2 was obtained from a recombinant baculovirus expression system (Mannie et al. (2003) Immunol Cell Biol 81, 8-19).

I. In Vitro Proliferation

Responder T cells ($2.5 \times 10^4$/well) were cultured with irradiated splenocytes ($5 \times 10^5$/well) and with designated concentrations of antigen. After 2 days of culture, T cells were pulsed with 1 µCi of [$^3$H]thymidine [6.7 Ci/mmol, Perkin-Elmer (Boston, Mass.)]. After another 1 day of culture, T cells were harvested onto filters to measure [3H]thymidine incorporation by scintillation counting. Error bars portray standard deviations.

J. Cytokine-Specific Activity of Cytokine/NAg Fusion Proteins

Recombinant baculovirus were used to infect Sf9 insect cells, and supernatants from infected cultures were tested for expression of the respective cytokine activities. These experiments (FIGS. 2-7) revealed that the cytokine domain of the respective cytokine/NAg fusion proteins had intact cytokine-specific biological activity.

Figure 2A:
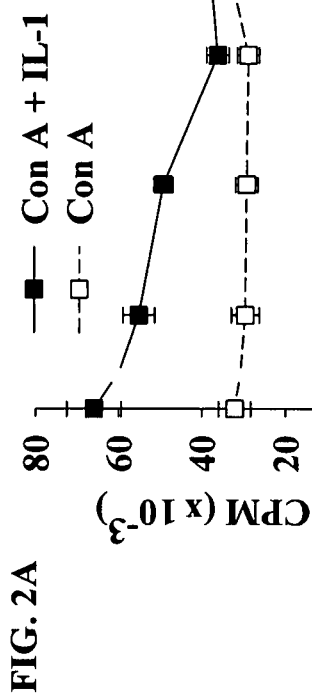
Figure 2B:
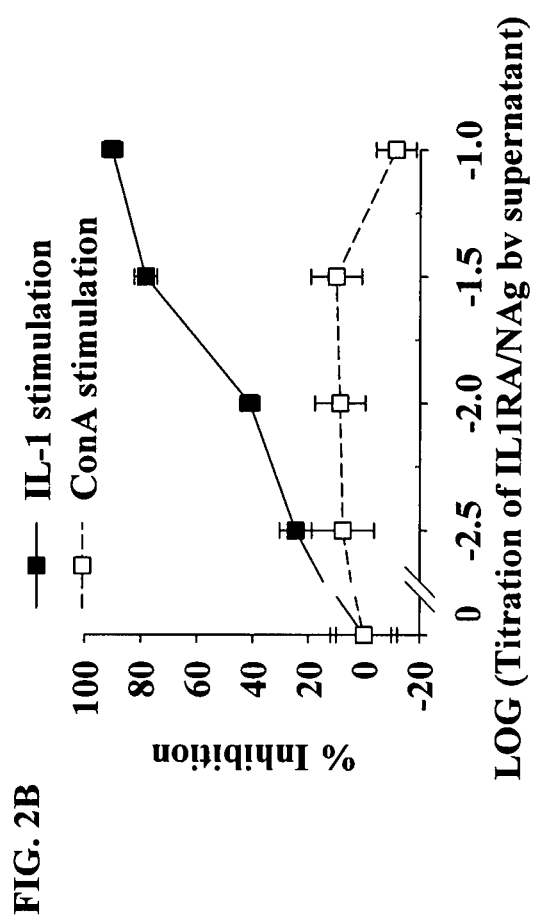

Supernatants containing IL1RA/NAg4 blocked IL-1 activity (FIG. 2). In accordance with a widely-used bioassay for IL-1RA (Arend et al. (1989) J Immunol 143, 1851-1858), IL-1 augmented the proliferation of mitogen-stimulated thymocytes, and the IL1 RA/NAg4 fusion protein blocked the ability of IL-1 to augment mitogen-stimulated proliferation. The IL1RA/NAg baculovirus system inhibited over 90% of IL-1 augmented proliferation. At all titrations tested, the IL1RA/NAg baculovirus supernatant did not significantly inhibit Con A-stimulated proliferation in the absence of recombinant human IL-1β. Thymocyte proliferation in response to Con A or the combination of Con A & IL-1 is shown in FIG. 2, Panel A. The same data are portrayed in FIG. 2, Panel B as percent inhibition of IL-1 stimulated growth versus percent inhibition of Con A-stimulated growth. These data indicated that IL1 RA/NAg4 blocked the action of IL-1 but did not interfere with Con A-stimulated mitogenesis per se. These findings were consistent with the predicted bioactivities of IL1 RA, and the specificity of the inhibitory effect discounted a nonspecific inhibitory mechanism.

Four different IL-2 fusion proteins exhibited equivalent IL-2 activity in a CTLL bioassay (Gillis et al. (1978) J Immunol 120, 2027-2032) (FIG. 3, Panel A) when the respective baculovirus supernatants were titrated from 10% ($10^{-1}$) to approximately 0.00001% ($10^{-7}$). The exponent of the titration was plotted on the x-axis. The C-terminal addition of Ek-GP-6his (IL2.7), GP-6his (IL2Ekdel), or 6his (IL2-D) domains did not appear to affect IL-2 bioactivity or the efficiency of the baculovirus expression system. A normative $Ala^2$ was inserted into the signal sequence after the N-terminal Met in IL2.7, IL2Ekdel, IL2-D, & IL2-C to provide an optimal Kozak translation initiation sequence (Kozak (1997) Embo J 16, 2482-2492). This structural alteration however appeared to be without consequence (FIG. 3, Panel A). A single mutation ($Y^{146}$ for $C^{146}$) in the IL2-C protein however was associated with an approximate 1,000 fold reduction in activity (FIG. 3, Panel B). Because supernatants rather than purified protein were assessed, the reduction in activity may be associated with decreased expression, stability, or activity of the mutant protein. By homology to human IL-2 (Wang et al. (1984) Science 224, 1431-1433), rat IL-2 likely has a single disulfide bond between $C^{78}$ and $C^{126}$ and a single unpaired $C^{146}$. The substitution of $Y^{146}$ for $C^{146}$ was a chance mutation detected during DNA sequencing of recombinant pFastbac1 plasmids. In prokaryotic expression systems for human or murine IL-2, this unpaired Cys was deliberately substituted with Ser or Ala to prevent inappropriate disulfide bond formation, and these substitutions did not compromise biological activity (Wang et al. (1984) Science 224, 1431-1433; Liang et al. (1986) J Biol Chem 261, 334-337). However, the $Y^{146}$ for $C^{146}$ mutation in rat IL-2 was not well tolerated.

IL-4 is a known T cell growth factor (Yokota et al. (1986) Proc Natl Acad Sci USA 83, 5894-5898; Mitchell et al. (1989) J Immunol 142, 1548-1557). Accordingly, the IL4.4 cytokine/NAg fusion protein, like IL2.7, had mitogenic activity in thymocyte cultures that were co-stimulated with PHA and IL-1β (FIG. 4, Panel A). Baculovirus supernatants containing these proteins exhibited mitogenic activity at titrations as low as 0.02% ($10^{-3.7}$). The mitogenic activity was attributed to IL-2 and IL-4, because fusion proteins incorporating other cytokines [IL1 RA (not shown), IL-10, or IL-13] were without activity. IL-4 activity was distinguished from IL-2 by assays in which thymocytes were co-stimulated with IL-2 and PMA (FIG. 4, Panel B). IL2.7 did not stimulate additional proliferation in this assay because IL-2 was present in saturating concentrations in all wells. In this assay, IL4.4 and a sister clone IL4.8 stimulated thymocyte proliferation whereas the IL2.7, IL10.6, and IL13.6 fusion proteins had no activity.

Consistent with the known activities of IL-4 and IL-13 (Doherty et al. (1993) J Immunol 151, 7151-7160; Doyle et al. (1994) Eur J Immunol 24, 1441-1445; Bogdan et al. (1997) J Immunol 159, 4506-4513), the IL4.4 and IL13.6 fusion proteins (native ss-cytokine-EK-GP-6his) also inhibited nitric oxide production by γ IFN-stimulated macrophages. When added together into the same culture, the IL4.4 and IL13.6 fusion proteins resulted in an approximate nonadditive inhibition of nitric oxide production (FIG. 5, Panels A and B). This observation is consistent with the existence of a shared signal transduction pathway involving a common IL-4R alpha chain in the respective receptor signaling complexes (Aversa, G et al. (1993) J Exp Med 178, 2213-2218; Mentink-Kane and Wynn (2004) Immunol Rev 202, 191-202; Arima et al. (2005) J Biol Chem 280, 24915-24922). IL4.4 and IL13.6 were the only fusion proteins capable of inhibiting γIFN-induced nitric oxide production whereas other fusion proteins such as IL2.6, IL10.6, and IL1RA/NAg4 lacked inhibitory activity (FIG. 5, Panel C and data not shown). IL2.6 and IL2.7 proteins were derived from sister clones and had identical protein sequence. These data verify IL-4 and IL-13 as cytokines that modulate macrophage activity.

Unlike IL4.4, IL13.6 had no activity on T cells. Both IL4.4 and IL4 (without NAg) profoundly inhibited the IL-2 dependent growth of the MBP-specific RsL.11 clone and the con-albumin-specific Conal.8D9 clone (FIG. 6, Panels A and B) whereas IL4.4, IL4, and IL4-A elicited T cell growth in thymocyte cultures costimulated with IL-2 and PMA (FIG. 6, Panel C). These data indicated that IL-4 receptors exist on both IL-2 dependent lines of memory rat Th1 T cells and on naïve thymocytes and mediate inhibitory or stimulatory action according to the differentiated function of either subset. In contrast, the IL-13 fusion proteins (IL13.6, IL13-A, nor IL13-B) did not modulate the proliferation of the IL-2 dependent T cell lines (RsL.11 or Conal.8D9) and did not affect the growth of thymocytes even though IL13-based fusion proteins inhibited nitric oxide production by macrophages (FIG. 6, Panel D). These data are consistent with previous reports indicating that IL4 receptors but not IL-13 receptors are present on T cells, whereas both IL-4 and IL-13 receptors exist on macrophages (Zurawski and de Vries (1994) Immunol Today 15, 19-26).

In accordance with the ability of IL-10 to augment IL-2 dependent T cell proliferation (MacNeil et al. (1990) J Immunol 145, 4167-4173), Baculovirus supernatants containing the IL10.6 fusion protein (native ss-IL10-EK-GP-6his) augmented the IL-2 dependent growth of several rat T cell lines, including that of the GP.3H3.16 clone, the RsL.11 clone, and the GP2 line (data not shown). IL10.6 augmented IL-2 dependent growth even at high concentrations (1 nM) of IL-2 but had no stimulatory effect on T cell growth in the absence of IL-2 (FIG. 7, Panel A). In RsL.11 T cell cultures supplemented with IL-2, IL10.6 also increased cell size as measured by forward scatter (FIG. 7, Panel B, left) and augmented expression of the IL-2Rα chain (OX39 marker) whereas other cytokine/NAg fusion proteins had no activity in this assay (FIG. 7, Panel B, right). These data are consistent with the known ability of IL-10 to augment IL-2 dependent T cell growth and facilitate expression of IL-2 receptors on T cells.

Together, these data (FIGS. 2-7) indicate that cytokine domains in the IL1RANAg, IL2NAg, IL4NAg, IL10NAg, and IL13NAg fusion proteins are biologically active. The baculovirus expression systems resulted in the efficient secretion of these fusion proteins into the supernatant.

K. Antigen-Specific Activity of Cytokine/NAg Fusion Proteins

The baculovirus expression system coupled with a two-step affinity chromatography procedure resulted in yields of approximately 0.5-2.0 mg of purified protein per 400 ml starting volume of culture. Protein fractions were qualitatively assessed on 12% SDS-PAGE gels, were typically 90% pure, and exhibited a size range and banding pattern consistent with the predicted MW and potential number of N-linked glycosylation sites (FIG. 8). Recombinant proteins secreted from Sf9 insect cells are known to contain high mannose structures (Altmann et al. (1999) Glycoconj J 16, 109-123; Chang et al. (2003) J Biotechnol 102, 61-71). Over-expression of recombinant protein may overwhelm the N-glycosylation machinery and lead to incomplete addition of high mannose sugars. Several of the cytokine/NAg proteins; IL4.4 and IL13.6 in particular, showed MW patterns consistent with incomplete N-linked glycosylation.

The cytokine/NAg proteins exhibited antigenic activity when tested in the presence of the RsL.11 T cell clone and irradiated splenic APC (FIG. 9, Panel A). The IL4Ekdel (IL4/GP73-87/6his) protein was at least 1000 times more potent as an antigen than GPMBP. Likewise, IL4.4 had an enhanced antigenic potency that was similar to IL4Ekdel (data not shown). Fusion proteins IL2Ekdel, IL10.6, and IL13.6 had antigenic potency that was commensurate to that of GPMBP whereas IL1RA/NAg4 had potency that was typically about 10-fold less than GPMBP. The stimulatory activity of these cytokine/NAg fusion proteins in this assay was entirely dependent upon MHC class II glycoproteins because an anti-MHCII I-A IgG1 mAb (OX6) abrogated the proliferative response. In contrast, the OX17 mAb anti-MHCII I-E IgG1 mAb had no inhibitory action (data not shown). Therefore, this assay measured antigenic rather than cytokine dependent responses.

Even though IL-2 is known to drive the proliferation of RsL.11 T cells, IL-2 was only effective when RsL.11 T cells were activated and expressed high levels of IL-2 receptor. When RsL.11 T cells were quiescent, as they were at the outset of this assay (FIG. 9, Panel A), these T cells did not respond to IL-2. Rather, engagement of the T cell antigen receptor was required to enable IL-2 responsiveness. Overall, these data (FIG. 9) indicate that these cytokine/NAg fusion proteins, including IL2NAg, are efficiently processed by splenic APC for presentation of the NAg on MHCII glycoproteins.

These fusion proteins were also tested in the presence of draining lymph node cells (LNC) obtained from Lewis rats sensitized with DHFR/NAg in CFA. The DHFR/NAg protein was a recombinant protein bearing dihydrofolate reductase as a N-terminal domain fused to the C-terminal GP69-87 peptide of GPMBP. The IL1 RA/NAg4, IL13.6, and GPMBP proteins stimulated approximately 30,000 cpm of [$^3$H]thymidine, and the OX6 mAb blocked this response (background of ~5,000 cpm) (FIG. 9, Panel B). In the case of IL2Ekdel, IL4Ekdel, and IL10.6, the fusion proteins stimulated mixed responses that were in part due to the cytokine domain and in part due to antigenic stimulation of NAg-specific T cells. For example, 100 nM IL2Ekdel stimulated approximately 156,000 cpm and 100,000 cpm of [3H]thymidine incorporation in the absence or presence of OX6 respectively. The same concentration of IL4Ekdel stimulated approximately 71,000 cpm and 29,000 cpm of [$^3$H]thymidine incorporation in the absence or presence of OX6 respectively.

These fusion proteins were also tested in an MHCII-dependent assay of T cell-mediated killing. In these experiments, blastogenic MHCII$^+$ T cells from the R1-trans T cell clone were APC. Previous studies (Patel et al. (1999) J Immunol 163, 5201-5210; Mannie and Norris (2001) Cell Immunol 212, 51-62; Patel et al. (2001) Cell Immunol 214, 21-34) showed that presentation of NAg (or conalbumin) by R1-trans T cells to irradiated MBP-specific (or conalbumin-specific) responders resulted in antigen-specific killing of R1-trans T cells by a MHCII-restricted mechanism. In this assay, R1-trans T cells grew rapidly in the presence of IL-2 unless these T-APC were killed by irradiated RsL.11 responders. As shown in FIG. 10, Panel A, 1 µM GPMBP completely inhibited the IL-2 dependent proliferation of R1-trans T cells, and the anti-I-A MHCII mAb OX6 abrogated this inhibition by preventing antigen recognition. In this assay of MHCII-dependent T cell-mediated killing, the IL2Ekdel protein was more potent than GPMBP or DHFR-NAg by at least 5 orders of magnitude (FIG. 10, Panel B). Indeed, the IL2Ekdel fusion protein was fully active at the lowest concentration tested—100 fM. The IL4Ekdel protein was approximately 1000 times more potent than GPMBP. These data indicate that the cytokine domains of the IL2Ekdel and IL4Ekdel fusion proteins may potentiate antigen presentation based on high affinity interactions with the respective cytokine receptors on the surfaces of APC.

L. Cytokine/NAg Protects Against the Subsequent Active Induction of EAE:

Subcutaneous injection of the cytokine/NAg fusion proteins in saline or in alum did not cause EAE and did not cause adverse reactions or signs of inflammation at the injection site. The following scale was used to assign intensity of EAE; paralysis in the distal tail, 0.25; limp tail, 0.5; ataxia, 1.0; hind leg paresis, 2.0; full hind leg paralysis, 3.0. The cumulative score for each rat consisted of the sum of daily scores for each animal. The mean cumulative score for a group was calculated by averaging the cumulative scores for all rats within a group. Mean maximal intensity was calculated for each group based on the average maximum score among afflicted rats within a group. The mean severity of EAE (y-axis of graphs) was the average score of all rats in a group on a given day.

Three fusion proteins (IFNβNAg, NAgIL16, IL2NAg) proved to be effective tolerogens as measured by the development of resistance to the subsequent induction of EAE. IFNβNAg (referred to IFN 3.4) was one of these tolerogenic proteins. Rats were pretreated with saline or with 1 nmole GP69-88 (encephalitogenic peptide YGSLPQKSQRSQDENPVVHF, SEQ ID NO:33) or 1 nmole IFNβ.4 (native ss-IFNβ-EK-NAg-6his) on days −21, −14, −7 and were challenged with 50 µg DHFR-NAg in CFA on day 0. DHFR-NAg is a fusion protein comprised of murine dihydrofolate reductase fused with the encephalitogenic GP69-87 peptide. DHFR-NAg was derived in our laboratory as prokaryotic expression system for the encephalitogenic peptide (Qiagen). DHFR-NAg has the full encephalitogenic activity of GPMBP (not shown).

Rats pretreated with the IFNβ.4 fusion protein had less severe EAE compared to rats pretreated with either GP68-89 or saline (Table 4). These data show marked inhibition of clinical EAE by IFNβ.4.

Subcutaneous injection of the IL2NAg or IL4NAg fusion proteins in saline or in alum did not cause EAE and did not cause adverse reactions at the injection site. Pretreatment of rats with IL2NAg (IL2.7) in saline or alum significantly attenuated the subsequent induction of EAE (Table 5). A total of three subcutaneous injections of IL2.7 (0.5 or 1 nmole per injection) were administered to each rat over the course of 1-2 months, and then rats were then challenged with GPMBP in CFA to elicit EAE. Pretreatment of 12.7 in saline or alum significantly reduced the mean cumulative score and the mean maximal intensity of EAE. When administered in saline, IL2.7 also resulted in a delayed onset of disease. The mechanism by which IL2.7 inhibited EAE most likely involved tolerance induction because at least one week elapsed between the last fusion protein injection and the encephalitogenic challenge—a delay that allowed ample time for clearance of the fusion proteins before challenge.

The tolerogenic activity of the IL-2NAg fusion protein was contingent upon the covalent linkage of IL-2 and NAg (Table 6). Rats pretreated with IL2Ekdel had a lower mean cumulative score and a reduced mean maximal intensity compared to rats pretreated with saline, the encephalitogenic GP69-88 synthetic peptide, purified rat IL-2, or the combination of IL-2 and GP69-88. Rats pretreated with IL2Ekdel also had a delayed onset of EAE compared to rats pretreated with saline, GP69-88, or IL-2 alone. These findings indicated that the tolerogenic activity of IL2NAg was antigen-specific rather than a cytokine-dependent, antigen-nonspecific activity. The tolerogenic activity of IL2NAg also could not be attributed to the antigen alone. Rather, the tolerogenic activity reflected a synergy attributed to the covalent linkage of IL-2 and NAg. Lastly, these data provide evidence that two independently derived IL2NAg fusion proteins, (IL2.7, Table 5 and IL2Ekdel, Table 6) had tolerogenic activity.

Rats challenged with DHFR-NAg in CFA often had a single relapse marked by a milder second course of EAE (FIG. 11). Pretreatment with IL2Ekdel completely prevented relapse in rats challenged with DHFR-NAg whereas over 50% of rats in the other four groups had spontaneous relapses. The finding of reduced disease severity in primary EAE and abrogation of EAE in the subsequent relapse indicated that the tolerogenic consequences of IL2NAg treatment endured for over one month.

When delivered in either saline or alum, the IL4.4 fusion protein lacked tolerogenic activity (Table 7). Rats were given subcutaneous injections of IL4.4, IL2.7, or GPMBP at a dose of 1 nmole on day −42, −28, and −14, and then were challenged with 25 µg GPMBP in CFA on day 0. Again, pretreatment of rats with IL2.7 significantly decreased the mean cumulative score and the mean maximal intensity of EAE and delayed the onset of EAE compared to control groups. These data indicate that IL-2 is more efficient than IL-4 as a fusion partner for induction of tolerance to NAg. When cytokine/NAg fusion proteins were injected in alum rather than saline (Tables 5 & 6), the encephalitogenic challenge resulted in an accelerated onset of EAE. The ability of alum to accelerate the course of disease was independent of the ability of IL2.7 to suppress disease. Thus, pretreatment with IL2.7 in alum decreased incidence and severity of EAE but nonetheless accelerated disease onset.

IL2NAg (IL2Ekdel) was also substantially more tolerogenic than IL4NAg (IL4Ekdel) when delivered after encephalitogenic challenge. Rats were sensitized with DHFR-NAg in CFA on day 0 and then administered the respective fusion protein on days 5, 7, and 9 (Table 8, experiment #1) or on days 5, 7, 9, and 11 (Table 8, experiment #2). These data reinforce the concept that IL2NAg fusion proteins are more tolerogenic than IL4NAg fusion proteins and that IL2NAg fusion can suppress EAE when administered either before or after an encephalitogenic challenge.

M. Cytokine/NAg Fusion Proteins Target NAg to APC

As shown in FIG. 12, Panel A, purified cytokine/NAg fusion proteins stimulated proliferation of an encephalitogenic $CD4^+$ clone specific for the 72-86 region of MBP in the presence of irradiated splenic APC. The IL4.4 fusion protein was over 100-fold more potent than GPMBP based on a comparison of the antigen concentrations eliciting a half maximal response. The proliferative response to IL2.7 was bimodal. Concentrations of IL2.7 in the 10 pM to 1 nM range stimulated approximately 20,000 cpm of [$^3$H]thymidine incorporation. IL2.7 concentrations of 1 nM to 1 uM stimulated the second mode of responsiveness.

IL4.4 and IL2.7 stimulated T cell proliferation by a mechanism restricted by MHCII I-A but not I-E (FIG. 12, Panel B). Responses elicited by IL4.4 and IL2.7 were completely abrogated by the OX6 mAb (anti-I-A MHCII) but were not affected by the OX17 (anti-1-E MHCII) mAb. Indeed, the antigenic reactivity of IL4.4 was inhibited by over 5 orders of magnitude by OX6 whereas the response to GPMBP was inhibited by an ~100 fold margin. These findings were in accordance with the known antigen restriction of the RsL.11 clone. Thus, when cultured with these cytokine/NAg fusion proteins and irradiated splenic APC, RsL.11 T cells exhibited antigen-stimulated proliferation rather than a mitogenic response to the cytokine domain. Other control cytokine/NAg fusion proteins (IL10.6, IL13.6, and NAgIL16-S) had antigenic reactivity similar to that of GPMBP (FIG. 12, Panel A). These responses were also fully blocked by an anti-MHCII I-A mAb (OX6) and thereby represented antigenic responses to the encephalitogenic peptide (not shown). These data indicated that the encephalitogenic GP73-87 sequence in each fusion protein was processed and presented on MHCII glycoproteins.

Covalent linkage of the respective cytokine with the NAg was required for enhanced potency of antigen recognition. IL4.4 was ~100 fold more potent than GPMBP even when GPMBP was added in culture with saturating concentrations of IL-4 as a separate molecule (FIG. 13, Panel A). IL-4 activity of the IL4.4 protein and of the 1% and 0.1% IL4.4 baculovirus supernatants was confirmed in a mitogenesis assay of thymocytes (FIG. 13, Panel C). Because thymocytes were costimulated with PMA and saturating concentrations of IL-2 in all wells, the assay specifically detected IL-4 activity but not IL-2 activity. The enhanced antigenic potency of IL4.4 could not be explained by an independent action of IL-4 on either APC or T cell responders. For example, the ability of IL-4 to induce MHCII on B cells could not explain the enhanced potency of the IL4.4 antigen because IL4-induced MHCII induction would increase antigenic potency without requirement for cytokine-antigen linkage. The antigenic activity of IL4.4 was also substantially more active than the IL-4 activity of IL4.4 (compare FIG. 13, Panel A & FIG. 13, Panel C).

Covalent linkage of IL-2 and NAg was involved in the enhanced potency of IL2.7 (FIG. 13, Panel B). That is, IL2.7 was ~100 fold more potent than GPMBP even when GPMBP was added to culture with saturating concentrations of IL-2 as a separate molecule. The IL-2 activity of IL2.7 and the 1% and 0.1% IL2.7 baculovirus supernatants was confirmed in a mitogenesis assay of CTLL cells (FIG. 13, Panel D). IL-2 did not directly stimulate RsL.11 T cells because these T cells were rested and had low concentrations of IL-2 receptors. Thus, the enhanced potency of IL2.7 compared to GPMBP could not be explained by the mitogenic activity of IL-2. Rather, the covalent tethering of IL-2 and NAg allowed synergistic antigenic activity that was not be duplicated by adding IL-2 and NAg to culture as separate molecules.

The IL2.7 fusion protein was also substantially more potent than GPMBP in a T cell-mediated cytotoxic assay (FIG. 14). In these experiments, blastogenic MHCII$^+$ T cells from the R1-trans T cell clone were APC. Previous studies showed that presentation of antigen by R1-trans T cells to irradiated antigen-specific responders resulted in antigen-specific killing of R1-trans T cells by a MHCII-restricted mechanism. In this assay, R1-trans T cells grew rapidly in the presence of IL-2 unless these T-APC were killed by irradiated RsL.11 responders (14, 23). The assays were devised such that IL2.7 fusion protein competed with IL-2 for IL-2R on T-APC. Cultures were supplemented with rat IL-2 at the initiation of culture (IL-2 at 0 hrs), 4 hrs after the initiation of culture (IL-2 at 4 hrs), or 24 hrs after initiation of culture (IL-2 at 24 hrs). R1-trans T-APC mediated rapid IL-2 dependent growth (y-axis) unless irradiated RsL.11 T cells killed R1-trans T cells upon recognition of antigen on R1-trans T cells. Irradiation of RsL.11 T cells prevented their antigen-specific proliferation but not cytotoxicity. The data indicated that when addition of IL-2 was delayed until 24 hours after the initiation of culture, IL2.7 was over 1000 times more potent than GPMBP. However, when IL-2 was added at the initiation of culture with IL2.7 or GPMBP, IL2.7 was only ~32 fold more potent than GPMBP. These data indicate that the IL2.7 fusion protein competed with IL-2 for cell surface IL-2 receptors and that this competition determined the quantity of the IL2.7-associated NAg loaded into the MHCII-antigen processing pathway. Overall, these data support the hypothesis that IL-2 receptors on T cells can be used to target antigen to the MHCII-antigen processing pathway of activated T cells to enhance antigen recognition.

The potentiated responses of RsL.11 T cells to IL4.4 and IL2.7 that were stimulated in the presence of irradiated splenic APC were also inhibited in part by IL-4 and IL-2, respectively. For example, IL-4 inhibited the response to IL4.4 by ~10 fold but only slightly inhibited the response to GPMBP (FIG. 15, Panel A) or IL2.7 (not shown). Likewise, IL-2 inhibited the IL2.7 proliferative activity by ~10 fold but slightly enhanced proliferative responses to GPMBP (FIG. 15, Panel B) and IL4.4 (not shown). These data provide additional evidence that the enhanced antigenic potency of IL4.4 and IL2.7 was due to targeting of fusion proteins to the respective cytokine receptors.

The availability of a monoclonal antibody (mAb) specific for IL-4 (OX81) provided another approach to assess the ability of the cytokine domain of the fusion protein to target the NAg to APC. This mAb allowed neutralization of the IL-4 domain in the IL4NAg fusion protein. The antigenic activity of IL4.4 was inhibited by the OX81 mAb by approximately 100-fold to the extent that IL4.4 was rendered equipotent to GPMBP (FIG. 16). The inhibitory action of OX81 was specific in that OX81 did not affect antigenic responses stimulated by either GPMBP or IL2.7. These data indicate that in the presence of OX81, the NAg in IL4.4 had antigenic reactivity that was essentially equal to GPMBP and that the encephalitogenic 73-89 sequences in IL4.4 and GPMBP were processed and presented equally as measured by responses of cloned RsL.11 T cells.

N. Derivation and Expression of IL-16/NAg Fusion Proteins

Three different IL-16 expression systems were generated for this study: NAgIL16-S, IL16-S, and NAgIL16-L (Table 2). IL-16 is known to be synthesized as a large precursor protein that is cleaved by caspase-3 into an N-terminal domain (~1285 aa) that is translocated into the nucleus and a C-terminal domain (~118 aa) that constitutes the active secreted IL-16 (Zhang et al. (1998) J Biol Chem 273, 1144-1149; Zhang et al. (2001) J Biol Chem 276, 1299-1303). The NAgIL16-S, IL16-S, and NAgIL16-L fusion proteins were comprised of the 118 aa IL-16 C-terminal domain.

Like the other cytokine/NAg fusion proteins described above (Tables 2 and 9), the initial IL16NAg was expressed as a N-terminal IL-16 domain fused to a C-terminal EK-NAg-6his domain. However, this expression system resulted in suboptimal antigenic activity. Hence, new IL16 were derived that positioned the NAg at the N-terminus and IL-16 at the C-terminus. Thus, the NAgIL16-S construction encoded the HBM signal sequence, a 7-histidine tag, the 69-87 sequence of GPMBP, and the C-terminal 118 aa fragment of IL-16. Primer design was based on the mouse IL-16 sequence (Keane et al. (1998) J Immunol 160, 5945-5954) (accession AF006001). IL-16 cDNA was synthesized in the presence of 200 nM of the 7H01 downstream primer, 1 μg total RNA, first strand buffer, dNTP, DTT, and SuperScript III Reverse Transcriptase (Invitrogen) according to manufacturer's instructions. To generate this fusion construct, an overlap extension reaction was used to generate the HBMss-7his-NAg DNA, and the IL-16 DNA was amplified in the same reaction tube.

Primers were designed such that the HBMss-7his-NAg construct overlapped the IL-16 DNA. Given the presence of excess upstream and downstream primer, the full length HBMss-7his-NAg-IL16 construct resolved as a major product of this single PCR reaction. This reaction included the 3F09 upstream primer (200 nM) and the 3F12 primer (100 nM) to generate the N-terminal HBM-7his-GP69-87 construct together with the 3F11 primer (100 nM) and the downstream 7H01 primer (200 nM) to amplify the IL16 DNA. The reaction was catalyzed by Platinum High Fidelity Taq DNA Polymerase (Invitrogen). Cycling parameters included an initial denaturation at 95° C. 5' followed by 29 cycles of 94° C. 1', 62° C. 2', and 68° C. 2', and then a final 68° C. 10' extension step. The upstream 3F09 and the downstream 7H01 primers included Spe I and Kpn I restriction endonuclease sites that facilitated cloning of the construct into the multiple cloning site of the pFastbac1 plasmid (Invitrogen). The recombinant NAgIL16-S pFastbac1 plasmid was then used for derivation of recombinant baculovirus as described in the BAC-TO-BAC Baculovirus Expression System (Invitrogen).

The IL16-S construct was generated by a similar overlap extension—PCR strategy. The NAgIL16-S pFastbac1 plasmid was used as a template, and primers (6H08 and 7H11) were designed to delete the sequence encoding the GP69-87 NAg. The 3E06 upstream primer (200 nM) and the 6H08 primer (100 nM) were used to generate an N-terminal HBM-7his construct as an extension product, and in the same reaction tube, the 7H11 primer (100 nM) and the 7H01 primer (200 nM) were used to amplify the IL-16 sequence from the plasmid. Due to overlap between these two constructs, the final amplification product resolved as a contiguous HBMss-7his-IL16 construct flanked by Spe I and Kpn I restriction endonuclease sites. This construct was inserted into the pFastbac1 vector, which was used to derive the IL16-S recombinant baculovirus.

Publication of the predicted rat IL-16 sequence (XP_218851) revealed that the C-terminal amino acid accounted for the only difference between the predicted rat sequence (C-terminal leucine) and either NAgIL16-S or IL16-S(C-terminal serine). To express authentic rat IL-16 (C-terminal leucine), site-directed mutagenesis was used to alter this codon. To generate the NAgIL16-L construct, the NAgIL16-S pFastbac1 plasmid was used as template for a whole plasmid PCR in the presence of the 7A01 and 1F07 primers and Platinum Pfx DNA polymerase. 7A01 was the mutagenic primer containing a 2-nucleotide substitution (TTG substituted in place of for TCA) in the terminal 5' codon. This primer and the 1F07 primer were overlapping primers that generated linearized copies of the plasmid. The reaction mix was melted at 95° C. for 5' followed by 29 cycles at 94° C. for 30", 60° C. for 1', 68° C. for 3' followed by a 68° C. 10' extension step. The products were washed and concentrated by use of Microcon YM100 Centrifugal Filter Devices, were treated with Dpn I restriction endonuclease to deplete residual parental plasmid, and were used to transform Top10 *E coli* by electroporation.

Upstream primers contained a Spe I site (ACTAGT) and downstream primers contained a Kpn I site (GGTACC) to facilitate cloning of fusion inserts into the multiple cloning site of the pFastBac1 vector (Table 3). The DNA constructs were cut with the combination of KpnI and SpeI restriction endonucleases and were ligated into (Kpn I×Spe I)-cut pFastbac1 vector (Invitrogen). Recombinant plasmids were transformed into Top10 *E. coli*. Plasmid DNA was purified and sequenced to confirm the predicted sequence. Recombinant plasmids were then transformed into DH10Bac *E. coli* to achieve transposition of the fusion construct into the baculovirus genome. Baculovirus DNA was purified and transfected into Sf9 insect cells to generate supernatants containing recombinant baculovirus. Supernatants containing the recombinant fusion proteins were confirmed by PCR and by secretion of the predicted protein into supernatants of infected Sf9 cells.

O. Purification of Cytokine/NAg Fusion Proteins

Purification of proteins bearing a C-terminal 6-histidine tag including IL1RA/NAg4, IL2.7, IL2Ekdel, IL2, IL10.6, and IL13.6 were described previously. Proteins bearing an N-terminal histidine tag (NAgIL16-S, IL16-S, and NAgIL16-L) were purified by immobilized metal ion affinity chromatography (IMAC) on Ni resin (Qiagen). Fusion proteins were secreted into the supernatant by Sf9 insect cells infected with the respective baculovirus and were concentrated on YM10 or YM5 ultrafiltration membranes. Concentrated supernatants were loaded onto 1 ml beds of Ni resin, were extensively washed (50 mM $NaH_2PO_4$, 500 mM NaCl, 10 mM imidazole, pH 8.0) and then eluted with 250 mM imidazole (pH 8.0). Proteins were then concentrated and reapplied to a second step of IMAC. Protein quantity was assessed by the BCA protein assay (Pierce), and purity was assessed by SDS-PAGE.

P. Tolerance Induction

To determine whether cytokine/NAg proteins prevent active induction of EAE in Lewis rats, rats were given 3 subcutaneous injections of a given cytokine/NAg protein (1 nmole dose) in saline at 1-2 week intervals as designated. At least 7 days after the last injection of the respective fusion protein, rats were challenged with NAg in CFA (day 0) to induce EAE. Alternatively, cytokine/NAg fusion proteins were tested to determine whether these proteins could ameliorate EAE when administered after challenge.

Q. Induction and Clinical Assessment of EAE

EAE was induced in Lewis rats by injection of an emulsion containing GPMBP in CFA (200 µg *Mycobacterium tuberculosis*). In designated experiments, rats were challenged with the DHFR-NAg fusion protein. This protein was comprised of the mouse dihydrofolate reductase as the N-terminal domain and the encephalitogenic GP69-87 peptide of GPMBP as the C-terminal domain (manuscript in preparation). The following scale was used to assign intensity of EAE: paralysis in the distal tail, 0.25; limp tail, 0.5; ataxia, 1.0; hind leg paresis, 2.0; full hind leg paralysis, 3.0. The cumulative score for each rat consisted of the sum of daily scores for each animal. The mean cumulative score for a group was calculated by averaging the cumulative scores for all rats within a group. The mean maximal intensity scores were assigned to each group based on the average maximum score among afflicted rats within a group. The mean severity of EAE (y-axis of graphs) was the average score of all rats in a group on a given day.

R. Cytokine/NAg Fusion Proteins

The baculovirus expression systems for cytokine/NAg fusion proteins IL1RANAg, IL2NAg, IL4NAg, IL10NAg, IL13NAg were described previously. These fusion proteins had predicted cytokine activities as assessed by bioassay. The IL1RA/NAg4 protein blocked the ability of IL-1 to enhance proliferation of Con A-stimulated thymocytes without inhibiting Con A-stimulated thymocyte proliferation in the absence of IL-1. IL2NAg stimulated proliferation of rat splenic T cells, thymic T cells, and established T cell lines. IL4NAg stimulated proliferation of PMA-costimulated thymocytes but inhibited the IL-2 dependent growth of MBP-specific and conalbumin-specific T cell clones. Both IL4NAg and IL13NAg blocked γIFN-induced nitric oxide production by macrophages. IL10NAg enhanced the IL-2 dependent growth of established T cell clones.

S. Comparative Tolerogenic Activity of Cytokine/NAg Fusion Proteins

NAgIL16 and NAgIL2 fusion proteins were injected subcutaneously in saline at a dose of 1 nmole every 1-2 weeks for a total of three injections. Two different forms of NAgIL16 (NAgIL16-S and NAgIL16-L) and two different forms of IL2NAg (IL2.7 and IL2Ekdel) were tested for tolerance induction. Seven days after the last injection of cytokine/NAg, rats were actively challenged with GPMBP or with DHFR-NAg. As shown in Table 9, both NAgIL16 and IL2NAg had tolerogenic activity. Both versions of NAgIL16 were highly effective tolerogens and significantly reduced the mean cumulative score of EAE compared to rats pretreated with equal doses of NAg (GPMBP or GP69-88 peptide). NAgIL16 also significantly decreased the mean maximal intensity and delayed the onset of EAE. Although IL2.7 and IL2Ekdel were not as efficient as NAgIL16, both IL2NAg proteins were effective tolerogens compared to GPMBP or the synthetic peptide GP69-88. IL2NAg significantly reduced the mean cumulative score and mean maximal intensity of EAE and significantly delayed onset of disease. Thus, two independently derived versions of NAgIL16 and two independently derived versions of IL2NAg had tolerogenic activity.

Other anti-inflammatory or tolerogenic fusion proteins were tested to address the question of whether NAgIL16 and IL2NAg fusion proteins exhibited unique tolerogenic activity (Table 10). Again, the fusion proteins were administered in three injections (days –21, –14, & –7, 1 nmole/injection), and 7 days were allowed to elapse between the last pretreatment and the encephalitogenic challenge (50 µg GPMBP in CFA). The IL10.6 did not exhibit tolerogenic activity whereas the IL13.6 and IL1RA/NAg4 fusions proteins decreased the mean cumulative score and mean maximal activity and delayed disease onset compared to rats pretreated with saline. However, these measures were not significant compared to those of rats pretreated with GPMBP. Overall, the rank order of tolerogenic activity for the six fusion proteins in the Lewis rat model of EAE was: NAgIL16>IL2NAg>>IL1RANAg, IL13NAg≥IL10NAg, GP69-88, GPMBP≥saline (Tables 9 and 10).

T. Linkage of IL-16 and NAg was Indicated in Tolerance

The tolerogenic activity of the NAgIL16 fusion proteins was contingent upon the covalent linkage of IL-16 and NAg (Table 11). Rats pretreated with NAgIL16 were resistant to the subsequent active induction of EAE. These rats showed a significant reduction in the mean cumulative score and mean maximal intensity together with a delayed onset of disease. Furthermore, rats pretreated with NAgIL16 did not exhibit a spontaneous relapse of EAE. In contrast, rats pretreated with a combination of IL16 and GP69-88 as separate molecules or with either agent alone were fully susceptible to EAE, and many of these rats showed a spontaneous relapse of disease. These data indicated that tolerance induction reacted to the linked activity of IL-16 and NAg. Thus, the mechanism of tolerance induction was antigen-specific rather than an antigen-nonspecific cytokine-mediated effect. Furthermore, the tolerogenic activity elicited by NAgIL16 endured long after the last administration of the fusion protein.

Example 3

Tolerogenic Vaccines

Because immunological tolerance is antigen-dependent, a pretreatment regimen was best suited for finding an antigen-specific tolerogenic vaccine. Conversely, treatment regimens whereby fusion proteins were administered during or after encephalitogenic sensitization may reveal the immunosuppressive activities of the anti-inflammatory cytokine domain and may not involve an antigen-dependent tolerogenic response. Experiments were performed to determine whether these fusion proteins would inhibit EAE when administered during the sensitization or effector phase of EAE or whether these fusion proteins may augment EAE or have unanticipated allergic or anaphylactic activities.

The NAgIL16 fusion protein was highly effective when delivered systemically at the onset of the effector phase (Table 12 and FIG. 17). Rats challenged on day 0 with DHFR-NAg in CFA were treated with 5 nmoles NAgIL16-L intravenously on day 8 and then were given an equivalent intraperitoneal injection on day 12. These injections completely blocked progression to severe EAE. Compared to control rats that received equivalent dosages of GP69-88, rats receiving NAgIL16-L exhibited a significant reduction in the mean cumulative score and the mean maximal intensity and showed a delayed onset of disease. These data indicate that NAgIL16 regulates events that are involved in the effector phase of EAE.

Systemic administration may provide sufficient bioavailability, such that the fusion protein may interact with effector cells that have disseminated from lymph nodes to the spleen and CNS.

Subcutaneous administration of NAgIL16 during the effector phase also reduced the severity of EAE (Table 13). Pre-challenge treatment regimens (Tables 5-11) showed that NAgIL16 and IL2NAg were the most effective tolerogens compared to the other cytokine/NAg fusion proteins or to NAg alone. Likewise, this post-challenge treatment regimen (administration of cytokine/NAg on days 5, 7, and 9) revealed the same finding—that NAgIL16 and IL2NAg were the most effective for inhibition of EAE. Treatment with IL2NAg or NAgIL16 significantly reduced the mean cumulative score and mean maximal intensity of EAE (Table 13). IL4Ekdel, IL10.6, IL13.6, and IL1RA/NAg4 were administered to parallel groups and were less effective inhibitors. Subcutaneous injections were administered at sites adjacent to the encephalitogenic challenge so that the fusion protein would enter the same lymphatic drainage. These data indicate that the two fusion proteins exhibiting the greatest tolerogenic potency in pretreatment regimens were also the two most effective proteins for attenuating the effector phase of EAE. NAgIL16 and IL1RA/NAg4 were also tested in a regimen to deliver the fusion protein subcutaneously throughout the sensitization phase (days –1, 3, and 7) of EAE (Table 14). Again, NAgIL16 reduced the severity of EAE whereas IL1RA/NAg4 was less effective. The ability of NAgIL16 to inhibit the effector phase of EAE was antigen-dependent (Table 15). The fusion protein NAgIL16 reduced the mean cumulative score, the mean maximal intensity, and decreased the incidence of severe EAE whereas administration of IL-16 and NAg as separate molecules was ineffective and did not alter the course of disease.

To test the effect of dosage for NAgIL16-mediated tolerance, rats were pretreated with NAgIL16 at four different doses (FIG. 18). The data show that the ability of NAgIL16 to induce tolerance was dose dependent. The highest two doses elicited the most profound tolerogenic response.

The NAgIL16 fusion protein was the most effective tolerogen. This fusion protein decreased severity of EAE and decreased the incidence of severe EAE. Both pre-challenge and post-challenge delivery regimens were effective. When a pre-challenge delivery regimen was combined with a post-challenge delivery regimen (Table 16), the NAgIL16 also significantly suppressed disease incidence to 22% (compared to 100% in the two respective control groups). These data indicate that more chronic treatment regimens have the potential to completely inhibit a paralytic demyelinating autoimmune disease in rodents.

Example 4

Fusion Proteins Target the MHCII Antigen Processing Pathway

A. IL2NAg

IL2NAg may target the covalently-tethered NAg into the major histocompatibility complex class II (MHCII) antigen processing pathway of activated T cells.

First, purified cytokine/NAg fusion proteins stimulated antigenic proliferation of an encephalitogenic CD4$^+$ clone specific for the 72-86 region of MBP in the presence of irradiated splenic APC. The proliferative response to IL2NAg was bimodal (data not shown). Concentrations of IL2NAg in the 10 pM to 1 nM range stimulated approximately 20,000 cpm of [$^3$H]thymidine incorporation. At this concentration range, IL2.7 was substantially more active than GPMBP. In this assay, IL4NAg also exhibited enhanced antigenic potency. IL4NAg was ~100 fold more active than GPMBP. Other control cytokine/NAg fusion proteins (IL10NAg, IL13NAg, and NAgIL16) had antigenic reactivity similar to that of GPMBP. These fusion proteins stimulated T cell proliferation by a mechanism restricted by MHCII I-A but not 1-E. These data indicated that the encephalitogenic GP73-87 sequence IL2NAg was processed and presented on MHCII glycoproteins.

Second, covalent linkage of IL-2 with the NAg was required for enhanced potency of antigen recognition of IL2NAg. IL2.7 was ~100 fold more potent than GPMBP even when GPMBP was added to culture with saturating concentrations of IL-2 as a separate molecule. The IL-2 activity of IL2.7 and the 1% and 0.1% IL2 baculovirus supernatants was confirmed in a mitogenesis assay of CTLL cells. IL-2 did not directly stimulate RsL.11 T cells because these T cells were rested and had low concentrations of IL-2 receptors. Thus, the enhanced potency of IL2.7 compared to GPMBP could not be explained by the mitogenic activity of IL-2. Rather, the covalent tethering of IL-2 and NAg enabled synergistic antigenic activity that could not be duplicated by adding IL-2 and NAg to culture as separate molecules. The most consistent interpretation is that the cytokine domain interacted with the respective cytokine receptor on APC to target the covalently linked NAg into the MHCII antigen processing pathway.

Third, IL4NAg was ~100 fold more potent than GPMBP even when GPMBP was added in culture with saturating concentrations of IL-4 as a separate molecule. IL-4 activity of the IL4.4 protein and of the 1% and 0.1% IL4 baculovirus supernatants was confirmed in a mitogenesis assay of thymocytes. Because thymocytes were costimulated with PMA and saturating concentrations of IL-2 in all wells, the assay specifically detected IL-4 activity but not IL-2 activity. The enhanced antigenic potency of IL4.4 could not be explained by an independent action of IL-4 on either APC or T cell responders. For example, the ability of IL-4 to induce MHCII on B cells could not explain the enhanced potency of the IL4.4 antigen because IL4-induced MHCII induction would increase antigenic potency without requirement for cytokine-antigen linkage.

Fourth, the IL2NAg fusion protein was also more potent than GPMBP in a T cell-mediated cytotoxic assay. The enhanced potency of IL2NAg was reversed by the addition of IL-2 at the initiation of culture. When IL-2 was added at the initiation of culture, IL2NAg was only ~32 fold more potent than GPMBP. When the addition of IL-2 was delayed until 24 hours after the initiation of culture, IL2NAg was over 1000 times more potent than GPMBP. Thus, IL2NAg competed with IL-2 for cell surface IL-2 receptors, and this competition determined the amount of IL2NAg-associated NAg loaded into the MHCII-antigen processing pathway of these activated T cells. Overall, these data support the hypothesis that IL-2 receptors on activated T cells can be used to target antigen to the MHCII-antigen processing pathway of activated T cells to enhance antigen recognition Fifth, the potentiated responses of RsL.11 T cells to IL4NAg and IL2NAg that were stimulated in the presence of irradiated splenic APC were also inhibited in part by IL-4 and IL-2, respectively. For example, IL-4 inhibited the response to IL4NAg by ~10 fold but only slightly inhibited the response to GPMBP. Likewise, IL-2 inhibited the IL2NAg stimulated proliferative activity by ~10 fold but slightly enhanced proliferative responses to GPMBP. Lastly, the potentiated responses of RsL.11 T cells to IL4NAg were specifically blocked in the presence of the OX81 anti-IL4 mAb. These data provide additional evidence that the enhanced antigenic potency of IL4NAg and IL2NAg was due to targeting of fusion proteins to the respective cytokine receptors.

B. NAgIL16

NAgIL16 may target the covalently-tethered NAg into the MHCII antigen processing pathway of activated T cells. NAgIL16 was targeted for presentation by nonadherent Con A-activated splenic T cells (FIG. 19). Lewis rat splenocytes were cultured for 2 days in complete RPMI medium. Nonadherent splenocytes were then cultured with 100 nM, 10 nM, 1 nM, or 100 pM of designated fusion proteins in the presence of 2.5 µg/ml Con A. After 3 days of culture, splenic lymphoblasts were washed, irradiated, and used at designated cell densities as APC (x-axis) to stimulate the GPMBP-specific RsL.11 T cell line. Thus, antigen was incorporated into MHC class II glycoproteins during a 3-day culture in the presence of Con A, and then antigen presentation was measured in a subsequent 3-day culture in the absence of soluble antigen. The results showed that a concentration of 1 nM NAgIL16-L elicited stronger antigen presentation than 10 nM GPMBP or 100 nM DHFR-NAg. These data indicated that the IL16 moiety potentiated antigen presentation by at least 10-fold compared to NAg alone.

C. IFNβNAg

The cytokine domain of IFNβNAg has potent cytolytic activity for IL-2 activated T cells. The IFNβ domain endows APC with cytotoxic activity and simultaneously loads the covalently tethered NAg into the MHCII antigen processing compartment. The relevant APC in this model may or may not be T cells. This mechanism would deplete NAg-specific T cell responders and render rats resistant to EAE.

Example 5

In Vitro Activity of Purified IFNβNAg and IL2NAg Fusion Proteins

The IFNβNAg & IL2NAg fusion proteins exhibited potent biological activity (FIG. 20). The IL2NAg fusion proteins were active in the low picomolar range (half maximal responses in the 3-10 pM in standard CTLL assays). The IFNβNAg also exhibited a potency in the 1-10 pM range in a T cell cytotoxicity assay. In this assay, IFNβNAg directly killed IL-2 stimulated T cells (either the BN-GP T cell clone or the RsL.11 T cell clone) during a 3 day culture. These potencies compare very favorably to commercial IL-2 and IFNβ preparations.

Example 6

Cytokine/NAg Effects on Ongoing Autoimmune Encephalomyelitis

The results from an experiment in which in vivo tolerogenic activities of the NAgIL16 fusion protein in the Lewis rat model of Autoimmune encephalomyelitis (EAE) EAE are summarized in Tables 12 and 15. These data indicate that NAgIL16 can also reverse an ongoing encephalitogenic immune response and that this inhibitory activity is specific for NAg.

Example 7

NAgIL16 Treatment Inhibits Progression of EAE after Disease Onset

Administration of NAgIL16 during clinical disease halted EAE progression and prevented subsequent relapse as shown in FIG. 21. Data presented in tabular form (Table 19, Experiment 2) are shown as a time course of EAE. On day 11, rats were matched for clinical signs of EAE and were randomly assigned to one of two groups that were injected with either NAg (GP69-88) or NAgIL16L. (A) Treatments were on day 11 (5 nmoles in saline i.v.), day 12 (5 nmoles in saline i.p.), and day 14 (2 nmoles in saline i.v.) (see arrows). The cumulative EAE severity per day for NAgIL16-treated rats was significantly less than that for NAg-treated rats on days 13, 13.5, and 14 ($p=0.013$, $0.005$, and $0.009$, respectively). The mean cumulative scores (tallied after the first treatment on day 11) also were significantly different ($p<0.001$) (Mann-Whitney Test). (B) The frequency of relapses (onset after day 21) for NAg-treated rats (6 of 7, 85.7%) was significantly higher than for NAgIL16-treated rats (0 of 7) ($p=0.0047$, Fisher's Exact Test).

Thus, NAgIL16 had an acute inhibitory effect that suppressed an ongoing encephalitogenic attack and facilitated recovery. NagIL16 also exhibited longer term tolerogenic activity that prevented a subsequent relapse.

Example 8

Covalent Tethering of IL-2 and NAg in IL2NAg-Induced EAE Inhibition During the Onset of EAE The covalent linkage of IL2 and NAg played a role in the immunosuppressive activity of the post-challenge treatment regimen (Table 20). IL2NAg substantially reduced the median cumulative score, the median maximal intensity, the incidence of severe EAE, and the mean number of days that rats were afflicted with severe EAE whereas delivery of IL-2 and NAg simultaneously as separate molecules had no tolerogenic activity. These data indicate that IL2NAg is a highly effective inhibitor when delivered after encephalitogenic challenge and that IL2NAg can attenuate an ongoing encephalitogenic immune response. Comparison of the post-challenge treatment regimens (days 5, 7, & 9; days 5, 7, 9, & 11; days 5, 7, 9, 11, & 13) for data shown in Table 20 see above showed progressively more effective inhibition of EAE as treatments were extended into the phase of disease onset and maximal paralysis. These data provide suggestive evidence that IL2NAg directly impairs the effector phase of an ongoing encephalitogenic immune response.

Example 9

Dosing Regimens

Optimal doses that inhibit the subsequent induction of EAE are established. A dose of 1 nmole per injection (divided as 0.5 nmole on each side of the base of the tail) with a total of three injections is given at 1-2 week intervals. Dosing of fusion protein and induction of tolerance is shown by subcutaneous injection of NAgIL16-L, IFNβ.4, or IL2.7 by a regimen (total of 3 injections, one injection each on day −21, −14, and −7 followed by an encephalitogenic challenge with 50 μg DHFR-NAg on day 0). Groups of rats (n=10) receive 100 pmoles, 320 pmoles, 1 nmole, or 3.2 nmoles of each cytokine/NAg. One additional group of rats (n=4) receives 10 nmoles cytokine/NAg protein.

Higher doses of cytokine/NAg will either induce more profound tolerance, or induction is dependent upon low dose administration of the cytokine/NAg and that a high dose may be neutral or may promote sensitization as indicated by acceleration or more intense disease after challenge. High dose administration provides information regarding safety of each cytokine/NAg. At 1 nanomole doses, these fusion proteins did not result in a local reaction or any indication of EAE induction. Establishment of dose-response curves reveals an optimal dose as a balanced consideration of efficacy versus practicality of generating the given dosage. If high dose administration promotes any aspect of EAE induction, then using low doses exclusively or an escalating dose strategy similar to those currently used in the clinic for allergic desensitization are considered.

Dose-Dependence of NAgIL16-Mediated Inhibition of EAE

Cytokine/antigen fusion proteins may elicit a balance of effector and regulatory cells, and this balance may vary with dosage. Tolerogenic fusion proteins would predictably cause tolerance by dose—dependent mechanisms. Higher doses should induce more profound tolerance. However, paradoxical dosage effects are possible, and higher doses may more efficiently prime effector cells and promote immunity. To test the effect of dosage for NAgIL16-mediated tolerance, rats were pretreated with NAgIL16 at four different doses (FIG. 18). Rats were injected with saline or with 0.5, 1.0, 2.5, or 5.0 nmoles NAgIL16 on days −21, −14, and −7 and then were challenged with 50 μg DHFR-NAg in CFA on day 0. All four dosages of NAgIL16 resulted in significant tolerance, and the two highest two doses elicited the most profound tolerogenic response. These data indicate that the tolerogenic activity of NAgIL16 was dose dependent and that optimal tolerance may be induced with doses of 2.5-5.0 nmoles.

Example 10

Combination Treatments

NAgIL16 and IL2NAg fusion proteins can act synergistically. IFNβ may facilitate expansion of regulatory T cell subsets. Hence, the combination of IFNβNAg and either NAgIL16 or IL2NAg can load NAg into the MHCII antigen processing pathway of regulatory T cells.

Rats were immunized with 50 μg of DHFR-NAg in CFA on day 0. Rats (cytokine/NAg group) were injected subcutaneously with 1 nmole IL2/NAg (IL2Ekdel) in saline on days 5, 7, 10, and 12 and were also injected intravenously with 5 nmoles NAgIL16 in saline on days 8 and 11.

The experiment shown in Table 21 verified the efficacy of a combined treatment protocol including the use of IL2NAg and NAg IL6 fusion proteins injected on alternative days into the same group of rats. This combined treatment protocol eliminated severe paralytic disease and minimized disease to the distal tip of the tail. In contrast, control rats exhibited a full course of paralytic EAE. These data indicate that two fusion proteins (IL2NAg and NAgIL16) can be used in a combined treatment protocol to control an encephalitogenic attack.

Example 11

NAgIL16-Induced Tolerance

These experiments provide a balanced experimental design that assess the antigen specificity of the tolerogenic pathway, as opposed to a disease-specific or organ-specific mechanism or an antigen nonspecific cytokine-dependent mechanism of tolerance.

The mechanism by which the NAgIL16 fusion protein induced tolerance was addressed by adoptive transfer experiments discussed in Table 20. The prediction was that a mechanism of active dominant tolerance would be transferred from tolerant donors to naïve recipients by the transfer of lymphoid cells. In contrast, a passive mechanism of tolerance could not be transferred from tolerant donors to naïve recipients.

Rats were pretreated with 4 nmoles of GP69-88 (NAg) or 4 nmoles NAgIL16 in saline on days −28, −21, and −14. On day −7, draining lymph node cells and splenocytes were pooled from rats of each group and were injected (i.p.) into recipient rats (1:1 donor to recipient ratio). Seven days after adoptive transfer, recipient rats were challenged on day 0 with 50 µg of DHFR-NAg in CFA.

Table 22 provides evidence that sensitization of rats with NAgIL16 in saline promotes a mechanism of active tolerance as assessed by adoptive transfer. Donor rats were pretreated with 4 nmoles of NAgIL16 in saline or with 4 nmoles of the encephalitogenic peptide GP69-88 (NAg) in saline on days −28, −21, and −14. Sensitized splenocytes and draining lymph node cells from donor rats were harvested on day −7 and were transferred to recipients without culture. Seven days later, on day 0, recipient rats were challenged with DHFR-NAg in CFA to induce EAE. The results suggest that the NAgIL16 fusion protein elicited a dominant mechanism of active tolerance.

TABLES

TABLE 1

| Amino Acids | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

TABLE 2

Design of cytokine/NAg fusion proteins.

| Descriptor[a] | Name[b] | N to C terminal order of domains[c] |
|---|---|---|
| IL1RANAg | IL1RA/NAg4 | native ss-IL1RA-EK-(GP73-87)-6his |
| IL1RAwoNAg | IL1RA | native ss-IL1RA--6his |
| IL2NAg | IL2.7 | native ss-IL2-EK-(GP73-87)-6his |
| IL2NAg | IL2Ekdel | native ss-IL2-(GP73-87)-6his |
| IL2woNAg | IL2-D | native ss-IL2-6his |
| IL2woNAg | IL2 | native ss-IL2 |
| IL4NAg | IL4.4 | native ss-IL4-EK-(GP73-87)-6his |
| IL4NAg | IL4Ekdel | native ss-IL4-(GP73-87)-6his |
| IL4woNAg | IL4-A | native ss-IL4-6his |
| IL4woNAg | IL4 | native ss-IL4 |
| IL10NAg | IL10.6 | native ss-IL10-EK-(GP73-87)-6his |
| IL10woNAg | IL10 | native ss-IL10-EK-6his |
| IL13NAg | IL13.6 | native ss-IL13-EK-(GP73-87)-6his |
| IL13woNAg | IL13-A | native ss-IL13-6his |
| IL13woNAg | IL13-B | native ss-IL13-6his |
| IFN□ | IFN□.4 | native ss-IFN□-EK-(GP73-87)-6his |
| IFN□woNAg | IFN□ | native ss-IFN□-6his |
| NAgIL16[d] | NAgIL16-S | HBM ss-7his-NAg-C-terminal IL16 |
| IL16 alone[d] | IL16-S | HBM ss-7his-C-terminal IL16 |
| NAgIL16[d] | NAgIL16-L | HBM ss-7his-NAg-C-terminal IL16 |

[a]The descriptor defines the presence and the relative orientation of the cytokine and NAg domains in the fusion protein.
[b]The name refers to the specific names given to specific proteins.
[c]N to C terminal order of domains provides for a more detailed description of the relative order of domains for each recombinant protein. For example, in IL1RA/NAg4, the protein consisted of the native IL1RA signal sequence (ss), the mature IL-1RA cytokine, a enterokinase (EK) domain (G-D-D-D-D-K-G, SEQ ID NO:1), the major encephalitogenic peptide of GPMBP (P-Q-K-S-Q-R-S-Q-D-E-N-P-V-V-H, SEQ ID NO:2), and a 6-his C-terminal tag. The IL2.7, IL4.4, IL10.6, IL13.6, and IFNβ.4 fusion proteins had a parallel structural design comprised of an N-terminal cytokine domain and a C-terminal EK-NAg-6his domain. These latter fusions also had the native ss of the respective cytokine. In the IL1RAwoNAg, IL2woNAg, IL4woNAg, IL10woNAg, IL13woNAg, and IFNβwoNAg proteins, the cytokine was expressed without the Ek-NAg domain. Rat IL2Ekdel and IL4Ekdel had a deletion of the EK domain but were otherwise identical to IL2.7 and IL4.4 respectively. Rat IL2 and IL4 lacked the EK-NAg domain and were the only proteins lacking a C-terminal 6his tag.
[d]NAgIL16-S and IL16-S were cloned before the rat IL-16 sequence was available, and the cloning was accomplished by use of primers based on the mouse IL-16 sequence. These proteins have a C-terminal serine of the mouse sequence whereas the remainder of the protein encompasses the native rat sequence. The native C-terminal amino acid in rat IL-16 is a leucine. NAgIL16-S protein consisted of the honey bee mellitin (HBM) signal sequence (M-K-F-L-V-N-V-A-L-V-F-M-V-V-Y-I-S-Y-I-Y-A, SEQ ID NO:34), a 7-histidine tag, the encephalitogenic 69-87 peptide of GPMBP (Y-G-S-L-P-Q-K-S-Q-R-S-Q-D-E-N-P-V-V-H, SEQ ID NO:35), and the C-terminal 118 aa sequence of IL-16 with a C-terminal serine. NAgIL16-L was identical to NAgIL16-S except for the C-terminal substitution of leucine. IL16-S had a modified HBM ss (M-A-F-L-V-N-V-A-L-V-F-M-V-V-Y-I-S-Y-I-Y-A, SEQ ID NO:36), a 7-histidine tag, and the C-terminal 118 aa sequence of IL-16 with a C-terminal serine.

TABLE 3

Primers used to construct genes encoding cytokine/NAg fusion proteins.

| Primer name (code) | | Sequence of primer* |
|---|---|---|
| 5' IL-1RA | (3B05) | ATA<u>ACTAGT</u>ATGGAAATCTGCAGGGGACCTTACAGTCAC (SEQ ID NO:5) |
| 5' IL-2 | (3B12) | ATA<u>ACTAGT</u>ATGGCCTACAGCATGCAGCTC (SEQ ID NO:6) |
| 5' IL-4 | (2D11) | ATA<u>ACTAGT</u>ATGGGTCTCAGCCCCCACCTTGCTG (SEQ ID NO:7) |
| 5' IL-10 | (2D12) | ATA<u>ACTAGT</u>ATGGCACTTGGCTCAGCACTGCTATGTT (SEQ ID NO:8) |
| 5' IL-13 | (2E01) | ATA<u>ACTAGT</u>ATGGCACTCTGGGTGACTGCAG (SEQ ID NO:9) |
| 3' IL-1RA | (5A02) | CCTTTGTCATCGTCATCACCTTGGTCTTCCTGGAAGTAGAA (SEQ ID NO:10) |
| 3' IL-2 | (5A03) | CCTTTGTCATCGTCATCACCCTGAGTCATTGTTGAGATGAT (SEQ ID NO:11) |
| 3' IL-4 | (5A04) | CCTTTGTCATCGTCATCACCGGACATGGAAGTGCAGGACTG (SEQ ID NO:12) |
| 3' IL-10 | (5A05) | CCTTTGTCATCGTCATCACCATTTTTCATTTTGAGTGTCAC (SEQ ID NO:13) |
| 3' IL-13 | (5A06) | CCTTTGTCATCGTCATCACCGTGGCCATAGCGGAAAAGTTG (SEQ ID NO:14) |
| 5' EK-NAg | (5A01) | GATGACGATGACAAAGGACCCCAGAAGTCGCAGCGGTCCCAAG (SEQ ID NO:15) |
| 3' NAg | (2F07) | TAT<u>GGTACC</u>TTAGTGATGGTGATGGTGATGGACTACAGGGTTTTCATCTTGGGACCGCTGCGACT (SEQ ID NO:16) |
| IL2EKdel | (5H04) | ATCATCTCAACAATGACTCAG\CCCCAGAAGTCGCAGCGGTCCCAA (SEQ ID NO:17) |
| IL2EKdel | (6E12) | CTGAGTCATTGTTGAGATGATGCTTTGACAGAT (SEQ ID NO:18) |
| IL4EKdel | (5H05) | CAGTCCTGCACTTCCATGTCC\CCCCAGAAGTCGCAGCGGTCCCAA (SEQ ID NO:19) |
| IL4EKdel | (6F01) | GGACATGGAAGTGCAGGACTGCAAGTATTTCCCTCGT (SEQ ID NO:20) |
| 3' IL2-D | (6H03) | TAT<u>GGTACC</u>TTAGTGATGGTGATGGTGATG\CTGAGTCATTGTTGAGATGATGCT (SEQ ID NO:21) |
| 3' IL4-A | (6H04) | TAT<u>GGTACC</u>TTAGTGATGGTGATGGTGATG\GGACATGGAAGTGCAGGACTGCA (SEQ ID NO:22) |
| 3' IL13-A | (6H06) | TAT<u>GGTACC</u>TTAGTGATGGTGATGGTGATG\GTGGCCATAGCGGAAAAGTTGCTT (SEQ ID NO:23) |
| 5' HBM7hNAg | (3F12) | GACCGCTGCGACTTCTGGGGCAGGGAGCCATAATGGTGATGGTGATGGTGATGGGCATAGATGTAAGAAATGTA (SEQ ID NO:24) |
| 3' HBM7hNAg | (3F09) | ATA <u>ACTAGT</u>ATGAAATTCTTAGTCAACGTTGCCCTTGTTTTATGGTCGTATACATTTCTTACATCTATGCC (SEQ ID NO:25) |
| 5' NAgIL16S | (3F11) | TCCCTGCCCCAGAAGTCGCAGCGGTCCCAAGATGAAAACCCTGTAGTCCATTCTGCTGCATCAGCTTCAGTA (SEQ ID NO:26) |
| 3' NAgIL16S | (7H01) | TAT<u>GGTACC</u>TTATGAGTCTGCAGAAGCTGTTGTCTG (SEQ ID NO:27) |
| 5' HBM7h | (3E06) | ATA<u>ACTAGT</u>ATGGCATTCTTAGTCAACGTTGCCCTTGTTTTATGGTCGTATACATTTCTTACAT (SEQ ID NO:28) |
| 3' HBM7h | (6H08) | GCAGAATGGTGATGGTGATGGTGATGGGCATAGATGTAAGAAATGTATACGACCATAAAAAC (SEQ ID NO:29) |
| 5' IL16S | (7H11) | CATCACCATCACCATCACCATTCTGCTGCATCAGCTTCAGTAGC (SEQ ID NO:30) |
| NAgIL16Lmut | (7A01) | GACAACAGCTTCTGCAGACTTGTAAGGTACCAAGCTTGTC (SEQ ID NO:31) |
| NAgIL16L | (1F07) | AGTCTGCAGAAGCTGTTGTCTGCTTGCCCT (SEQ ID NO:32) |

*Upstream primers contained a Spe I site (ACTAGT) and downstream primers contained a Kpn I site (GGTACC) to facilitate cloning of fusion inserts into the multiple cloning site of the pFastBac1 vector. These restriction sites are underlined. The \ symbol shown for the 5H04 and 5H05 primers represents the juncture for deletion of the EK encoding region. The \ symbol shown for the 6H03, 6H04, and 6H06 primers represents the juncture for deletion of the EK-NAg encoding region. Overlap extension PCR was used to generate many of these constructs. For example, the NAgIL16-S construction encoded the HBM signal sequence, a 7-histidine tag, the 69-87 sequence of GPMBP, and the C-terminal 118 aa fragment of IL-16. Primer design was based on the mouse IL-16 sequence. IL-16 cDNA was synthesized in the presence of the 7H01 downstream primer. An overlap extension reaction included the 3F09 upstream primer and the 3F12 primer to generate the N-terminal HBM-7his-NAg construct together with the 3F11 primer and the downstream 7H01 primer to amplify the IL16 DNA. Overlap of the constructs resulted in the resolution of an amplification product encoding the full length fusion protein. The IL16-S construct was generated by a similar overlap extension - PCR strategy. The NAgIL16-S pFastbac1 plasmid was used as a template, and primers (6H08 and 7H11) were designed to delete the sequence encoding the GP69-87 NAg. The 3E06 upstream primer and the 6H08 primer were used to generate an N-terminal HBM-7his construct as an extension product, and in the same reaction tube, the 7H11 primer and the 7H01 primer were used to amplify the IL-16 sequence from the plasmid. Due to overlap between these two constructs, the final amplification product resolved as a contiguous HBMss-7his-IL16 construct flanked by Spe I and Kpn I restriction endonuclease sites. To generate the NAgIL16-L construct, the NAgIL16-S pFastbac1 plasmid was used as template for a whole plasmid PCR in the presence of the 7A01 and 1F07 primers. 7A01 was the mutagenic primer containing a 2-nucleotide substitution (TTG substituted in place of for TCA) in the terminal 5' codon. This primer and the 1F07 primer were overlapping primers that generated linearized copies of the plasmid.

TABLE 4

Vaccination with the IFNβ/NAg fusion protein elicits protection against EAE.

| Treatment of rats | Incidence of EAE | Mean cumulative score ± sd | Mean maximal EAE ± sd | Mean day of onset ± sd |
|---|---|---|---|---|
| Saline alone | 13 of 13 | 10.5 ± 3.0 | 2.9 ± 0.3 | 9.6 ± 1.5 |
| GP68-89 | 15 of 15 | 8.6 ± 3.3 | 2.7 ± 0.6 | 10.7 ± 1.1 |
| IFNβ.4 | 9 of 9 | 3.4 ± 2.7 | 1.4 ± 0.9 | 10.6 ± 0.5 |

The mean cumulative scores and the mean maximal EAE of rats pretreated with IFNβNAg (IFNβ.4) was significantly different from those treated with saline ($p < 0.001$) or GP68-89 ($p < 0.001$) (ANOVA, Tukey-Kramer Multiple Comparisons Test).

TABLE 5

Vaccination with the IL2NAg fusion protein protected against EAE.

| Exp. # | Treatment[a] | Incidence of EAE | Median cumulative score[b] | Median maximal intensity[b] | Mean day of onset[b] | Incidence of severe EAE[c] | Mean # days with severe EAE[d] |
|---|---|---|---|---|---|---|---|
| 1 | Saline alone | 6 of 6 | 9.5 | 3.0 | $11.5 \pm 1.5$ | 6 of 6 | $4.7 \pm 1.5$ |
|   | IL2.7-saline | 3 of 4 | 1.0 | 0.3 | $15.3 \pm 1.5$ | 0 of 4 | 0.0 |
| 2 | Saline alone | 6 of 6 | 11.1 | 3.0 | $8.7 \pm 0.8$ | 5 of 6 | $3.3 \pm 1.8$ |
|   | IL2.7-saline | 5 of 6 | 1.1 | 0.4 | $12.8 \pm 1.3$ | 2 of 6 | $1.0 \pm 1.6$ |
|   | IL2.7-alum | 1 of 6 | 0.0 | 0.0 | $8.0 \pm 0.0$ | 0 of 6 | 0.0 |
| 1&2 | Saline alone | 12 of 12 | 10.4 | 3.0 | $10.1 \pm 1.9$ | 11 of 12 | $4.0 \pm 1.7$ |
|   | IL2NAg-saline | 8 of 10 | 1.0 | 0.3 | $13.8 \pm 1.8$ | 2 of 10 | $0.6 \pm 1.4$ |
|   | IL2NAg-alum | 1 of 6 | 0.0 | 0.0 | 8.0 | 0 of 6 | 0.0 |

[a]Data were pooled from two independent experiments. In experiment #1, rats were pretreated with saline or 0.5 nmole IL2.7 (IL2NAg) on days −60, −42, and −20 and were challenged with 50 ug GPMBP in CFA on day 0. In experiment #2, rats were pretreated with saline or 1 nmole IL2.7 (in saline or alum) on days −35, −21 and −7 and were challenged with 25 ug GPMBP in CFA on day 0.

[b]Combined experiments: Median cumulative scores and median maximal intensity scores of rats pretreated with IL2NAg/saline ($p < 0.001$) or IL2NAg/alum ($p < 0.001$) were significantly less than the respective scores for rats treated with saline (two-way nonparametric ANOVA on ranks, Bonferroni Post Hoc Test). The mean day of onset of rats treated with IL2NAg in saline was significantly delayed compared to that for rats pretreated with saline (unpaired t test, $p = 0.0004$).

[c]Combined experiments: Rats that exhibited ataxia (A), early paresis (EP), or full hindlimb paralysis (P) were scored as positive for severe EAE. Incidence of severe EAE in rats pretreated with IL2NAg/alum ($p = 0.0004$) or with IL2NAg/saline ($p = 0.0015$) was significantly less than the respective incidence in rats pretreated with saline (pair-wise comparisons by Fisher's Exact Test).

[d]Each rat was scored for the total number of days that the rat exhibited severe EAE. The mean number of days that IL2NAg/alum-pretreated rats ($p < 0.001$) and IL2NAg/saline-treated rats ($p < 0.001$) exhibited severe EAE was significantly less than that for saline pre-treated rats (two-way parametric ANOVA, Bonferroni Post Hoc Test).

TABLE 6

Covalent tethering of IL-2 and NAg was necessary for tolerogenic activity.

| Exp. # | Treatment[a] | Incidence of EAE | Median cumulative score[b] | Median maximal intensity[b] | Mean day of onset[c] | Incidence of severe EAE[d] | Mean # of days with severe EAE[d] |
|---|---|---|---|---|---|---|---|
| 1 | Saline alone | 5 of 5 | 9.5 | 2.0 | $8.2 \pm 0.8$ | 5 of 5 | $4.0 \pm 1.0$ |
|   | GP69-88 | 5 of 5 | 9.8 | 3.0 | $8.8 \pm 2.2$ | 5 of 5 | $3.8 \pm 0.8$ |
|   | IL2 | 5 of 5 | 6.3 | 2.0 | $8.8 \pm 1.3$ | 5 of 5 | $4.4 \pm 1.1$ |
|   | IL2 & GP69-88 | 4 of 4 | 10.8 | 2.5 | $8.8 \pm 1.0$ | 4 of 4 | $4.3 \pm 1.0$ |
|   | IL2Ekdel | 4 of 4 | 3.6 | 1.3 | $10.0 \pm 0.8$ | 2 of 4 | $1.5 \pm 1.7$ |
| 2 | Saline alone | 7 of 7 | 9.3 | 3.0 | $11.0 \pm 1.2$ | 7 of 7 | $3.3 \pm 1.0$ |
|   | GP69-88 | 7 of 7 | 8.5 | 3.0 | $10.7 \pm 1.0$ | 7 of 7 | $3.3 \pm 0.5$ |
|   | IL2 | 8 of 8 | 11.3 | 3.0 | $9.8 \pm 0.9$ | 8 of 8 | $3.5 \pm 0.5$ |
|   | IL2 & GP69-88 | 6 of 6 | 12.0 | 3.0 | $11.3 \pm 0.8$ | 6 of 6 | $3.3 \pm 0.8$ |
|   | IL2Ekdel | 8 of 8 | 4.6 | 2.0 | $12.5 \pm 0.5$ | 7 of 8 | $2.0 \pm 1.2$ |
| 1 & 2 | Saline alone | 12 of 12 | 9.4 | 3.0 | $9.8 \pm 1.7$ | 12 of 12 | $3.6 \pm 1.0$ |
|   | NAg | 12 of 12 | 9.0 | 3.0 | $9.9 \pm 1.8$ | 12 of 12 | $3.5 \pm 0.7$ |
|   | IL2 | 13 of 13 | 9.3 | 3.0 | $9.4 \pm 1.1$ | 13 of 13 | $3.8 \pm 0.9$ |
|   | IL2 & NAg | 10 of 10 | 12.0 | 3.0 | $10.3 \pm 1.6$ | 10 of 10 | $3.7 \pm 0.9$ |
|   | IL2NAg | 12 of 12 | 4.3 | 2.0 | $11.7 \pm 1.4$ | 9 of 12 | $1.8 \pm 1.3$ |

[a]Rats were pretreated with saline, 1 nmole of IL2Ekdel (IL2NAg), 1 nmole GP69-88 (NAg), 1 nmole of IL2 (without NAg), or the combination of GP69-88 and IL2. Rats (IL2 & GP69-88) were treated with separate injections of 1 nmole IL2 and 1 nmole GP69-88 at a distance of <0.5 cm apart near the base of the tail. In experiment #1, rats were pretreated on days −27, −20, and −13 and were challenged with 50 ug GPMBP in CFA on day 0. In experiment #2, rats were pretreated on days −35, −21, and −7 and were challenged with 50 ug DHFR-NAg in CFA on day 0.

[b]Combined experiments: The median cumulative score ($p < 0.002$ all comparisons) and the median maximal score ($p < 0.02$ all comparisons) of rats pretreated with IL2NAg was significantly less than the respective scores of rats treated with saline, NAg, IL-2 alone, or the combination of IL2 and NAg (two-way nonparametric ANOVA on ranks; Bonferroni Post Hoc Test).

[c]Combined experiments: The mean day of onset of rats pretreated with IL2NAg was significantly delayed compared to the respective means of rats treated with either saline ($p = 0.049$) or IL-2 alone ($p = 0.005$) (two-way parametric ANOVA; Bonferroni Post Hoc Test).

[d]Combined experiments: Rats that exhibited ataxia (A), early paresis (EP), or full hindlimb paralysis (P) were scored as positive for severe EAE. Shown is the incidence of severe EAE together with the mean number of days each group exhibited severe EAE. The mean number of days that IL2NAg-treated rats were severely afflicted with EAE was significantly less than the respective means for groups pretreated with saline, NAg, IL2, or the combination of IL2 & NAg ($p \leq 0.001$ for all comparisons) (two-way parametric ANOVA; Bonferroni Post Hoc Test).

TABLE 7

IL2NAg was a more effective tolerogen than the IL4NAg fusion protein.

| Treatment[a] | Incidence of EAE | Mean day of onset[b] | Pooled treatment groups[c] | Median cumulative score[c] | Median maximal intensity[c] | Incidence of severe EAE[d] | Mean # of days with severe EAE[e] |
|---|---|---|---|---|---|---|---|
| Saline alone | 15 of 15 | 10.1 ± 1.5 | Saline | 2.5 | 1.0 | 8 of 15 (53%) | 1.6 ± 1.5 |
| GPMBP/saline | 3 of 4 | 12.3 ± 2.5 | GPMBP | 2.5 | 1.0 | 5 of 9 (56%) | 1.2 ± 1.3 |
| GPMBP/alum | 4 of 5 | 7.0 ± 1.4 | | | | | |
| IL4.4/saline | 9 of 10 | 11.0 ± 3.3 | IL4NAg | 3.1 | 1.0 | 11 of 16 (69%) | 1.6 ± 1.2 |
| IL4.4/alum | 6 of 6 | 7.0 ± 0.6 | | | | | |
| IL2.7/saline | 2 of 5 | 16.5 ± 2.1 | IL2NAg | 0.3 | 0.1 | 0 of 10 (0%) | 0.0 ± 0.0 |
| IL2.7/alum | 3 of 5 | 7.3 ± 1.5 | | | | | |

[a] Rats were given subcutaneous injections of IL4.4 (IL4NAg), IL2.7 (IL2NAg), or GPMBP at a dose of 1 nmole on days −42, −28, and −14, and then were challenged with 25 ug GPMBP in CFA on day 0.
[b] The mean day of onset of rats treated with IL2NAg in saline was significantly delayed compared to that for rats treated with IL4NAg in saline ($p = 0.0364$) (Mann-Whitney U Test). To assess the effects of the alum adjuvant on the mean day of onset, pooled data for the GPMBP/saline, IL4NAg/saline, and IL2NAg/saline groups ($n = 14$) revealed a significant delay compared to that for pooled data of the GPMBP/alum, IL4NAg/alum, and IL2NAg/alum groups ($n = 13$) ($p = 0.0002$). Unpaired t-tests were used to confirm these differences: (GPMBP/saline vs GPMBP/alum; $p = 0.0153$), (IL4NAg/saline vs IL4NAg alum; $p = 0.0128$), (IL2NAg/saline vs IL2NAg alum; $p = 0.0105$).
[c] Because the median cumulative score and median maximal intensity were not affected by the saline or alum adjuvant despite differences in mean day of onset, the data for each respective protein injected in saline or alum were pooled for statistical analysis of disease intensity. The median cumulative score and the median maximal intensity score for rats injected with IL2NAg (pooled saline & alum groups) was significantly less than the respective medians of the control group (saline only; $p < 0.01$), the pooled GPMBP group ($p < 0.05$), and the pooled IL4NAg group ($p < 0.001$) (Kruskal-Wallis nonparametric ANOVA on ranks; Dunn's Multiple Comparison Test).
[d] Rats that exhibited ataxia (A), early paresis (EP), or full hindlimb paralysis (P) were scored as positive for severe EAE. The incidence of severe EAE in rats treated with IL2NAg was significantly less than the respective incidences of rats treated with saline ($p = 0.0077$), GPMBP ($p = 0.0108$), IL4NAg ($p = 0.0007$) by Fisher's Exact Test. These differences were confirmed for groups possessing a sufficient n (saline, IL4NAg, and IL2NAg) by the Chi-Squared Test for Independence.
[e] Each rat was scored for the total number of days that the rat exhibited severe EAE. Shown are the mean and standard deviation for each pooled group (saline & alum). The mean number of days that IL2NAg-treated rats were severely afflicted with EAE was significantly less than the respective means of groups pretreated with saline ($p < 0.05$), GPMBP ($p < 0.05$), or IL4NAg ($p < 0.01$) (ANOVA, Tukey-Kramer Multiple Comparisons Test).

TABLE 8

Administration of IL2NAg after encephalitogenic sensitization also attenuated EAE.

| Exp. # | Treatment[a] | Incidence of EAE | Median cumulative score[b] | Median maximal intensity[b] | Mean day of onset[c] | Incidence of severe EAE[d] | Mean # days with severe EAE[d] |
|---|---|---|---|---|---|---|---|
| 1 | GP69-88 | 8 of 8 | 11.3 | 3.0 | 10.9 ± 1.4 | 8 of 8 | 3.1 ± 0.6 |
|  | IL4Ekdel | 6 of 6 | 7.6 | 3.0 | 12.8 ± 1.2 | 6 of 6 | 2.8 ± 0.4 |
|  | IL2Ekdel | 6 of 6 | 3.8 | 2.0 | 13.5 ± 0.8 | 5 of 6 | 1.8 ± 1.0 |
| 2 | GP69-88 | 8 of 8 | 7.5 | 3.0 | 9.9 ± 1.1 | 8 of 8 | 2.6 ± 0.9 |
|  | IL4Ekdel | 9 of 9 | 6.3 | 2.0 | 12.4 ± 1.3 | 7 of 9 | 3.0 ± 1.3 |
|  | IL2Ekdel | 8 of 9 | 1.0 | 1.0 | 12.5 ± 2.6 | 3 of 9 | 1.1 ± 1.2 |
| 1 & 2 | NAg | 16 of 16 | 9.4 | 3.0 | 10.4 ± 1.3 | 16 of 16 | 2.9 ± 0.8 |
|  | IL4NAg | 15 of 15 | 7.3 | 3.0 | 12.6 ± 1.2 | 14 of 15 | 2.9 ± 1.0 |
|  | IL2NAg | 14 of 15 | 3.3 | 2.0 | 12.9 ± 2.0 | 10 of 15 | 1.4 ± 1.1 |

[a] Rats were sensitized with 50 ug DHFR-NAg in CFA on day 0. Rats were then subcutaneously injected with 1 nmole of GP69-88 (NAg), IL4NAg (IL4Ekdel), or IL2NAg (IL2Ekdel) in saline on days 5, 7, and 9 (experiment #1) or on days 5, 7, 9, and 11 (experiment #2).
[b] Combined experiments: The median cumulative score and the median maximal intensity of rats treated with IL2NAg was significantly less than the respective medians for rats treated with either IL4NAg or NAg ($p < 0.001$ for all comparisons) (two-way nonparametric ANOVA on ranks, Bonferroni Post Hoc Test).
[c] Combined experiments: The mean day of onset of groups treated with IL2NAg or IL4NAg was significantly delayed compared to rats treated with NAg ($p \leq 0.001$ for both comparisons) (two-way parametric ANOVA; Bonferroni Post Hoc Test).
[d] Combined experiments: Rats that exhibited ataxia (A), early paresis (EP), or full hindlimb paralysis (P) were scored as positive for severe EAE. The mean number of days that IL2NAg-treated rats were severely afflicted with EAE was significantly less than the respective means for groups treated with IL4NAg or NAg ($p < 0.001$ for each comparison) (two-way parametric ANOVA; Bonferroni Post Hoc Test).

TABLE 9

IL-16NAg and IL-2NAg vaccination protect against the subsequent active induction of EAE.

| Exp.[a] | Treatment | Incidence of EAE | Mean cumulative score[b] ± sd | Mean maximal EAE[c] ± sd | Mean day of onset[d] ± sd |
|---|---|---|---|---|---|
| 1 | Saline alone | 10 of 10 | 9.4 ± 3.1 | 2.5 ± 0.7 | 10.6 ± 1.3 |
|  | GPMBP | 7 of 7 | 8.3 ± 4.1 | 2.6 ± 0.8 | 10.4 ± 0.8 |
|  | IL2.7 | 7 of 8 | 4.4 ± 3.3 | 1.8 ± 1.0 | 12.1 ± 1.2 |

TABLE 9-continued

IL-16NAg and IL-2NAg vaccination protect against the subsequent active induction of EAE.

| Exp.[a] | Treatment | Incidence of EAE | Mean cumulative score[b] ± sd | Mean maximal EAE[c] ± sd | Mean day of onset[d] ± sd |
|---|---|---|---|---|---|
|  | NAgIL16-S | 7 of 8 | 3.2 ± 2.5 | 1.5 ± 0.9 | 12.6 ± 1.0 |
| 2 | Saline alone | 6 of 6 | 9.2 ± 0.7 | 3.0 ± 0.0 | 10.0 ± 1.5 |
|  | GP69-88 | 7 of 7 | 8.5 ± 1.4 | 2.9 ± 0.4 | 10.4 ± 0.5 |
|  | IL2EKdel | 9 of 9 | 5.1 ± 2.6 | 2.1 ± 0.7 | 12.2 ± 0.7 |
|  | NAgIL16-L | 9 of 9 | 2.4 ± 1.2 | 1.1 ± 0.7 | 12.2 ± 0.4 |
| Combined | Saline alone | 16 of 16 | 9.3 ± 2.4 | 2.7 ± 0.6 | 10.4 ± 1.4 |
|  | NAg | 14 of 14 | 8.4 ± 3.0 | 2.7 ± 0.6 | 10.4 ± 0.6 |
|  | IL2NAg | 16 of 17 | 4.8 ± 2.9 | 1.9 ± 0.8 | 12.2 ± 0.9 |
|  | NAgIL16 | 16 of 17 | 2.8 ± 1.9 | 1.3 ± 0.8 | 12.4 ± 0.7 |

[a]In experiment #1, rats were pretreated with 1 nmole GPMBP, IL2.7, or NAgIL16.1 on days −31, −17, −7 and were challenged with 50 μg GPMBP in CFA on day 0. In experiment #2, rats were pretreated 1 nmole synthetic peptide GP69-88, IL2Ekdel, or rat NAgIL16 on days −21, −14, −7 and were challenged with 50 μg DHFR/NAg in CFA on day 0.
[b]Combined experiments: Mean cumulative scores of rats pretreated with IL16NAg or IL2NAg were significantly different from those treated with saline ($p < 0.001$) or NAg ($p < 0.001$ and $0.01$ respectively). The mean maximal intensity of rats pretreated with IL16NAg was significantly different from those treated with IL2NAg ($p < 0.05$), NAg ($p < 0.001$), or saline ($p < 0.001$). The mean maximal intensity of rats pretreated with IL2NAg was significantly different from those treated with NAg ($p < 0.05$) or saline ($p < 0.05$). The mean day of onset of rats pretreated with IL16NAg or IL2NAg was significantly different from those treated with NAg or saline ($p < 0.001$).

TABLE 10

Inhibitory Activity of IL10.6, IL-13.6 and IL1RA/NAg fusion proteins.

| Exp. | Treatment | Incidence of EAE | Mean cumulative score ± sd | Mean maximal intensity ± sd | Mean day of onset ± sd |
|---|---|---|---|---|---|
| 1 | Saline | 7 of 7 | 9.4 ± 4.4 | 2.9 ± 0.7 | 10.7 ± 1.0 |
|  | GP69-88 | 8 of 8 | 7.3 ± 3.7 | 2.4 ± 1.3 | 11.1 ± 2.2 |
|  | IL10.6 | 8 of 8 | 7.3 ± 3.8 | 2.3 ± 1.0 | 11.3 ± 1.3 |
| 2 | Saline | 17 of 17 | 9.5 ± 2.6 | 2.7 ± 0.5 | 10.6 ± 1.2 |
|  | GPMBP | 20 of 20 | 7.0 ± 3.4 | 2.4 ± 0.9 | 10.9 ± 0.9 |
|  | IL13.6 | 15 of 15 | 5.2 ± 2.9[a] | 2.0 ± 1.1 | 11.6 ± 0.7 |
|  | IL1RA/NAg4 | 13 of 13 | 4.8 ± 2.9[a] | 1.7 ± 0.9[b] | 12.2 ± 1.2[c] |

[a]The mean cumulative scores of rats pretreated with IL13NAg or IL1RA/NAg significantly differed from those treated with saline ($p < 0.001$).
[b]The mean maximal intensity of rats pretreated with IL1RA/NAg4 was significantly different from those treated with saline ($p < 0.01$).
[c]The mean day of onset of rats pretreated with IL1RA/NAg4 was significantly different from those treated with NAg or ($p < 0.01$) or saline ($p < 0.001$).

TABLE 11

Covalent tethering of IL-16 and NAg was involved in tolerogenic activity.

| Treatment of rats[a] | Incidence of EAE | Mean cumulative score ± sd[b] | Mean maximal intensity ± sd | Mean day of onset ± sd | Incidence of relapse |
|---|---|---|---|---|---|
| Saline alone | 6 of 6 | 10.5 ± 4.2 | 2.8 ± 0.4 | 10.3 ± 0.5 | 4 of 6 (33%) |
| NAgIL16-L | 9 of 9 | 2.2 ± 1.7 | 0.8 ± 0.7 | 13.2 ± 0.8 | 0 of 9 (0%) |
| GP69-88 | 7 of 7 | 9.0 ± 2.0 | 2.7 ± 0.5 | 10.3 ± 0.5 | 2 of 7 (29%) |
| IL16-S | 8 of 8 | 12.5 ± 2.6 | 3.0 ± 0.0 | 9.9 ± 1.0 | 5 of 8 (63%) |
| IL16-S & GP69-88 | 7 of 7 | 9.0 ± 2.1 | 2.9 ± 0.4 | 10.3 ± 0.5 | 3 of 7 (43%) |

[a]Rats were pretreated with saline, 1 nmole of NAgIL16-L, 1 nmole GP69-88, 1 nmole of IL16-S (no NAg), or the combination of GP69-88 and IL16-S. Rats (5th row) were treated with separate injections of 1 nmole IL16-S and 1 nmole GP69-88 at a distance of <0.5 cm apart near the base of the tail. Rats were pretreated on days −21, −14, and −7 and were challenged with 50 μg DHFR-NAg in CFA on day 0.
[b]The mean cumulative score, the mean maximal intensity, and the mean day of onset of rats pretreated with NAgIL16-L was significantly different from those treated with saline, GP69-88, IL16-S alone, or the combination of IL16-S and GP69-88 as separate molecules ($p < 0.001$). (ANOVA, Tukey-Kramer Multiple Comparisons Test).

TABLE 12

High-dose, systemic treatment with NAgIL16-L inhibited the effector phase of EAE.

| Treatment[a] | Incidence | Mean cum. Score ± sd | Mean max. intensity ± sd | Mean day of onset ± sd | Incidence of relapse |
|---|---|---|---|---|---|
| GP69-88 | 4 of 4 | 8.9 ± 2.6 | 3.0 ± 0.0 | 10.5 ± 0.6 | 2 of 4 (50%) |
| NagIL16-L[b] | 5 of 5 | 1.5 ± 0.9 | 0.5 ± 0.3 | 12.5 ± 1.0 | 0 of 5 (0%) |

[a]Rats were challenged with 50 μg DHFR-NAg in CFA on day 0. On day 8, rats were treated with 5 nmoles of GP69-88 or NagIL16-L intravenously. On day 12, rats were treated with 5 nmoles of GP69-88 or NagIL16-L by intraperitoneal injection. Injection of GP69-88 or NagIL16-L via these routes did not cause any notable adverse reaction. In the IL16-L treatment group, one rat exhibited initial signs of EAE (0.25) before administration of the first treatment. None of the other rats exhibited EAE at this timepoint (day 8). The day of onset for this rat was excluded from the calculation of the mean day of onset for the NagIL16-L treatment group.
[b]Mean cumulative score, the mean maximal intensity, and the mean day of onset of rats treated with NagIL16-L were significantly different from rats treated with GP69-88 (unpaired t test, $p < 0.0005$, $p < 0.0001$, and $p < 0.0135$, respectively).

TABLE 13

Subcutaneous IL2Ekdel and NagIL16-L injected on days 5, 7, & 9 attenuated EAE.

| Treatment[a] | Incidence | Mean cum. score[b] ± sd | Mean max. intensity ± sd | Mean day of onset[b] ± sd | Incidence of relapse |
|---|---|---|---|---|---|
| Saline | 8 of 8 | 10.3 ± 4.7 | 2.5 ± 0.9 | 11.0 ± 1.1 | 6 of 8 (75%) |
| GP69-88 | 8 of 8 | 10.5 ± 2.8 | 3.0 ± 0.0 | 10.9 ± 1.4 | 6 of 8 (75%) |
| IL4Ekdel | 6 of 6 | 7.6 ± 1.1 | 3.0 ± 0.0 | 12.8 ± 1.2 | 2 of 6 (33%) |
| IL10.6 | 6 of 6 | 6.5 ± 1.0 | 2.8 ± 0.4 | 12.5 ± 0.8 | 0 of 6 (0%) |
| IL13.6 | 6 of 6 | 6.4 ± 4.0 | 2.3 ± 1.2 | 12.3 ± 1.5 | 2 of 6 (33%) |
| IL1RA/NAg4 | 6 of 6 | 5.5 ± 2.0 | 2.4 ± 1.0 | 12.8 ± 0.4 | 0 of 6 (0%) |
| NAgIL16-L | 6 of 6 | 4.7 ± 1.8 | 2.1 ± 0.9 | 12.5 ± 1.0 | 0 of 6 (0%) |
| IL2Ekdel | 6 of 6 | 4.3 ± 2.4 | 2.0 ± 1.0 | 13.5 ± 0.8 | 0 of 6 (0%) |

[a]Rats were challenged with 50 μg DHFR-NAg in CFA on day 0. On days 5, 7, and 9, rats were treated with 1 nmole of GP69-88 or 1 nmole of the designated cytokine/NAg fusion protein by subcutaneous injection.
[b]Mean cumulative scores of rats treated with IL2Ekdel ($p < 0.01$) or with NAgIL16-L ($p < 0.05$) were significantly different from mean cumulative scores of rats treated with GP69-88 or saline. The mean cumulative score of rats treated with IL1RA/NAg4 was significantly different for that for rats treated with GP69-88 ($p < 0.05$). Mean day of onset of rats treated with IL1RA/NAg4 ($p < 0.05$), IL2Ekdel ($p < 0.01$), or IL4Ekdel ($p < 0.05$) were significantly different from the mean day of onset of rats treated with GP69-88. Mean day of onset of rats treated with IL2Ekdel ($p < 0.01$) was significantly different from the mean day of onset of rats treated with saline. (ANOVA; Tukey-Kramer Multiple Comparisons Test)

TABLE 14

The NAgIL16 vaccine was effective when delivered during sensitization.

| Exp.[a] | Treatment[a] | Incidence | Mean cumulative score | Mean max. EAE | Mean day of onset | Incidence of relapse |
|---|---|---|---|---|---|---|
| 1[b] | Saline | 5 of 5 | 11.8 ± 2.6 | 3.0 ± 0.0 | 11.2 ± 1.3 | |
| | IL1RA/NAg4 | 5 of 5 | 5.3 ± 3.8 | 2.0 ± 1.0 | 13.0 ± 1.2 | |
| | NAgIL16 | 5 of 5 | 5.3 ± 4.4 | 1.7 ± 1.3 | 12.0 ± 1.9 | |
| 2[c] | Saline | 10 of 10 | 11.6 ± 7.3 | 3.0 ± 0.0 | 9.6 ± 0.8 | 7 of 8 (88%) |
| | GP69-88 | 8 of 8 | 11.2 ± 2.7 | 3.0 ± 0.0 | 10.4 ± 0.7 | 5 of 8 (63%) |
| | IL1RA/NAg4 | 6 of 6 | 8.3 ± 3.9 | 2.5 ± 0.8 | 11.7 ± 1.0 | 3 of 6 (50%) |
| | NAgIL16 | 8 of 9 | 4.0 ± 3.1 | 1.9 ± 1.2 | 12.3 ± 0.5 | 1 of 8 (13%) |

[a]Rats were challenged with 50 μg GPMBP (experiment #1) or DHFR-NAg (experiment #2) in CFA on day 0. On days -1, 3, and 7, rats were treated with saline, GP69-88, or the designated cytokine/NAg fusion protein by subcutaneous injection. Either 1 nmole or 2 nmole doses per injection were administered in experiments 1 and 2, respectively.
[b]In experiment 1, mean cumulative score of rats treated with NAgIL16 or IL1RA/NAg4 was significantly different from those treated with saline ($p < 0.05$).
[c]In experiment 2, mean cumulative score and the mean maximal intensity of rats treated with NAgIL16 was significantly different from those treated with saline ($p < 0.01$) or GP69-88 ($p < 0.05$). The mean day of onset of rats treated with NAgIL16 was significantly different from those treated with saline or GP69-88 ($p < 0.001$). The mean day of onset of rats treated with IL1RA/NAg4 was significantly different from those treated with saline ($p < 0.001$) or GP69-88 ($p < 0.05$).

TABLE 15

NAgIL16-L treatment causes the antigen-specific inhibition of the encephalitogenic effector phase.

| Treatment[a] | Incidence of EAE | Mean cumulative score[b] ± sd | Mean maximal intensity[c] ± sd | Mean day of onset ± sd | Incidence of severe EAE (EP & P)[d] | Mean number of days afflicted with severe EAE[e] |
|---|---|---|---|---|---|---|
| NAgIL16L | 6 of 8 | 2.5 ± 2.5 | 1.0 ± 1.0 | 10.5 ± 0.5 | 2 of 8 (25%) | 0.4 ± 0.7 |
| Both | 8 of 8 | 6.8 ± 2.3 | 2.6 ± 0.5 | 10.1 ± 0.8 | 8 of 8 (100%) | 2.0 ± 0.8 |
| GP69-88 | 8 of 8 | 7.4 ± 2.1 | 2.9 ± 0.4 | 9.5 ± 1.2 | 8 of 8 (100%) | 2.4 ± 1.2 |
| IL-16 | 8 of 8 | 7.3 ± 1.1 | 3.0 ± 0.0 | 10.0 ± 0.9 | 8 of 8 (100%) | 2.1 ± 0.4 |

[a]Rats were challenged with 50 µg DHFR-NAg in CFA on day 0 and then were treated on day 8 with intravenous injections of 5 nmoles NAgIL16-L (1st row), a combined solution of 5 nmoles IL-16 & 5 nmoles GP69-88 (2nd row), 5 nmoles GP69-88 (3rd row), or 5 nmoles IL-16 (4th row). These same injections (5 nmoles) for each group were repeated by intraperitoneal injection on day 12.
[b]Parametric ANOVA (Tukey-Kramer Multiple Comparison's Test) revealed that the mean cumulative score of rats treated with NAgIL16 significantly differed from the respective scores for groups treated with IL-16 & GP69-88 ($p < 0.01$), GP69-88 ($p < 0.001$), or IL-16 ($p < 0.001$).
[c]Nonparametric Kruskal-Wallis ANOVA (Dunn's Multiple Comparisons Test) revealed that the mean maximal intensity score of rats treated with NAgIL16 significantly differed from those for groups treated with IL-16 & GP69-88 ($p < 0.05$), GP69-88 ($p < 0.01$), or IL-16 ($p < 0.001$).
[d]Rats that exhibited early paresis (EP) or full hindlimb paralysis (P) were scored as positive for severe EAE. The incidence of severe EAE in rats treated with NAgIL16L significantly differed from that for rats treated with the combination of IL-16 & GP69-88 ($p = 0.007$) by Fisher's Exact Test.
[e]Each rat was scored for the total number of days that the rat exhibited severe EAE (EP or P). Shown are the mean and standard deviation for each group. Nonparametric Kruskal-Wallis ANOVA (Dunn's Multiple Comparisons Test) revealed that the mean number of days that NAgIL16L-treated rats were severely afflicted with EAE significantly differed from the respective means of groups that were treated with the combination with IL-16 & GP69-88 ($p < 0.05$), GP69-88 ($p < 0.01$), or IL-16 ($p < 0.01$).

TABLE 16

A pre- and post-challenge NAgIL16 treatment regimen inhibits disease incidence.

| Treatment[a] | Incidence of EAE[b] | Mean cumulative score[c] | Mean maximal intensity[c] | Mean day of onset[d] | Incidence of severe EAE (A, EP, P)[e] | Mean number of days[e] afflicted with: mild EAE (dLT-LT) | Mean number of days[e] afflicted with: severe EAE (A-P) |
|---|---|---|---|---|---|---|---|
| NAgIL16L | 2 of 9 | 0.3 ± 0.8 | 0.3 ± 0.7 | 14.0 ± 2.8 | 1 of 9 | 0.3 ± 0.7 | 0.1 ± 0.3 |
| GP69-88 | 9 of 9 | 6.9 ± 3.3 | 2.8 ± 0.7 | 10.3 ± 1.4 | 9 of 9 | 2.4 ± 1.0 | 2.9 ± 1.4 |
| Saline | 9 of 9 | 8.5 ± 2.1 | 2.7 ± 0.5 | 8.8 ± 0.7 | 9 of 9 | 2.6 ± 1.0 | 3.8 ± 0.8 |

[a]Rats were pretreated with 2 nmoles NAgIL16L (1st row), 2 nmoles GP69-88 (2nd row), or saline (3rd row) on days −21, −14, and −7. Rats were challenged with 50 ug DHFR-NAg in CFA on day 0 and then were treated on days 8 and 11 with intraperitoneal injections of 5 nmoles of the respective antigen or saline.
[b]The incidence of EAE of rats treated with NAgIL16L was significantly less compared to the incidence of EAE in rats treated with GP69-88 ($p = 0.0023$) (Fisher's Exact Test).
[c]The mean cumulative score of rats treated with NAgIL16 was significantly reduced compared to the respective scores for rats treated with GP69-88 ($p < 0.01$) or saline ($p < 0.001$). The mean maximal intensity of rats treated with NAgIL16 was significantly reduced compared to the respective scores for rats treated with GP69-88 ($p < 0.001$) or saline ($p < 0.01$) (Nonparametric Kruskal-Wallis ANOVA; Dunn's Multiple Comparisons Test).
[d]The mean day of onset of rats treated with NAgIL16 was significantly delayed compared to the respective disease onset for rats treated with GP69-88 ($p < 0.01$) or saline ($p < 0.001$) (parametric ANOVA; Tukey-Kramer Multiple Comparisons Test).
[e]Rats that exhibited distal limp tail (dLT) or limp tail (LT) were scored as positive for mild EAE, and rats that exhibited ataxia (A), early paresis (EP), or full hindlimb paralysis (P) were scored as positive for severe EAE. The incidence of severe EAE in rats treated with NAgIL16L was significantly reduced compared to that for rats treated with GP69-88 ($p = 0.0004$) (Fisher's Exact Test). The mean number of days that NAgIL16L-treated rats were either mildly or severely afflicted with EAE was significantly reduced compared to the respective means of groups that were treated with GP69-88 ($p < 0.001$) or saline ($p < 0.001$) (parametric ANOVA; Tukey-Kramer Multiple Comparisons Test).

TABLE 17

Examination of combinations of vaccines for synergy for induction of tolerance.
Treatment groups (n = 10)

1. NAgIL16-L (1x dose)
2. IFNβ.4 (1x dose)
3. IL2.7 (1x dose)
4. GP68-89 (1x dose)
5. NAgIL16-L (2x dose)
6. IFNβ.4 (2x dose)
7. IL2.7 (2x dose)
8. GP68-89 (2x dose)
9. NAgIL16-L plus IL2.7
10. NAgIL16-L plus IFN□.4
11. IL2.7 plus IFNβ.4
12. Saline

TABLE 18

Tolerance elicited by cytokine/NAg vaccines is antigen-specific.

| Tolerance induction | Challenge of rats with: | Outcome: |
|---|---|---|
| 1. NAgIL16-L | DHFR-NAg in CFA | Resistance to EAE |
| 2. IL2.7 | P0 peptide 180-199/CFA | Full susceptibility to EAN |
| 3. IFNβ.4 | P0 peptide 56-71/CFA | Full susceptibility to EAN |
| 4. Optimal combinations. | P2 peptide 53-81/CFA | Full susceptibility to EAN |
| 5. GP68-89 | | |
| 6. Saline | | |

TABLE 19

NAgIL16 treatment inhibits progression of EAE when administered after disease onset

| Exp. | Treatment[a] | Incidence of EAE | Mean cumulative score | Median cumulative score | Mean cumulative score (2.5 day window) | Median cumulative score (2.5 day window) | Mean intensity score | Median intensity score | Incidence severe EAE (EP & P) |
|---|---|---|---|---|---|---|---|---|---|
| 1 | NAg | 7 of 7 | 13.3 ± 7.0 | 12.5 | 4.9 ± 2.5 | 4.5 | 2.1 ± 1.0 | 2.0 | 5 of 7 |
|   | NAgIL16 | 8 of 8 | 6.7 ± 5.4 | 4.5 | 1.2 ± 0.7 | 1.0 | 1.0 ± 0.7 | 1.0 | 2 of 8 |
| 2 | NAg | 7 of 7 | 9.1 ± 1.6 | 8.3 | 3.6 ± 1.8 | 3.8 | 2.0 ± 0.8 | 2.0 | 5 of 7 |
|   | NAgIL16 | 7 of 7 | 3.5 ± 1.5 | 3.3 | 1.0 ± 0.5 | 0.8 | 0.9 ± 0.6 | 0.5 | 1 of 7 |
| 1 & 2 | NAg | 14 of 14 | 11.2 ± 5.4 | 10.0 | 4.3 ± 2.2 | 4.4 | 2.0 ± 0.9 | 2.0 | 10 of 1 |
|   | NAgIL16[b] | 15 of 15 | 5.2 ± 4.2 | 3.8 | 1.1 ± 0.6 | 0.8 | 1.0 ± 0.6 | 1.0 | 3 of 1 |

[a]Rats were challenged with 50 ug DHFR-NAg in CFA on day 0. Rats were randomly assigned to one of two treatment groups based on expression of distal limp tail (0.25) or limp tail (0.5) immediately before the first treatment. In experiment 1 (NAg group; 0.25, n = 2; 0.5, n = 5 and NAgIL16 group; 0.25, n = 2; 0.5, n = 6), treatments were administered on day 10 (5 nmoles i.v.) and day 11 (5 nmoles i.p.). In experiment 2 (NAg group; 0.25, n = 2; 0.5, n = 5 and NAgIL16 group; 0.25, n = 1; 0.5, n = 6), NAg and NAgIL16 were administered on day 11 (5 nmoles i.v.), day 12 (5 nmoles i.p.), and day 14 (2 nmoles i.v.). In experiments 1 & 2, rats were scored on approximate 12 hr intervals.
[b]The mean and median cumulative score, the mean and median cumulative scores for a 2.5-day window following the second treatment (days 12-14.5 and days 13-15.5 for experiments 1 & 2 respectively), and the mean and median maximal intensity scores for NAgIL16-treated rats were significantly less than those for NAg-treated rats (p < 0.001, Independent Samples T-Test). Differences in median values were assessed by comparison of ranked data. The incidence of severe EAE in NAgIL16-treated rats was significantly less than the respective incidence in NAg-treated rats (Fisher's Exact Test, p = 0.0092).

TABLE 20

Covalent tethering of IL-2 and NAg involvement in EAE inhibition with IL2NAg treatment during onset of EAE.

| Treatment[a] | Incidence of EAE | Median cumulative score[b] | Median maximal intensity[b] | Mean day of onset[c] | Incidence of severe EAE[d] | Mean # days with severe EAE[d] |
|---|---|---|---|---|---|---|
| Saline alone | 10 of 10 | 8.6 | 3.0 | 9.8 ± 0.6 | 10 of 10 | 3.0 ± 0.7 |
| IL2 & GP69-88 | 10 of 10 | 7.9 | 3.0 | 9.9 ± 0.9 | 9 of 10 | 3.0 ± 1.3 |
| IL2NAg | 8 of 10 | 0.6 | 0.3 | 11.5 ± 1.6 | 2 of 10 | 0.5 ± 1.1 |

[a]Rats were sensitized with 50 ug DHFR-NAg in CFA on day 0. Rats were then injected with saline, 1 nmole of IL2NAg (IL2Ekdel) in saline, or with separate injections of 1 nmole IL2 and 1 nmole GP69-88 in saline s.c. at a distance of <0.5 cm apart near the base of the tail on days 5, 7, 9, 11, and 13.
[b]The median cumulative score of rats treated with IL2NAg was significantly less than the respective scores of rats treated with saline or the combination of IL2 and GP69-88 (p < 0.01 or p < 0.05 respectively). The median maximal score (p < 0.01 all comparisons) of rats pretreated with IL2NAg was significantly less than the respective scores of rats treated with saline or the combination of IL2 and GP69-88 (Kruskal-Wallis nonparametric ANOVA on ranks; Dunn's Multiple Comparison Test).
[c]The mean day of onset of rats pretreated with IL2NAg was significantly delayed compared to the respective means of rats treated with either saline (p < 0.01) or the combination of IL-2 and GP69-88 (p < 0.05) (one-way parametric ANOVA; Tukey-Kramer Multiple Comparisons Test).
[d]Rats that exhibited ataxia (A), early paresis (EP), or full hindlimb paralysis (P) were scored as positive for severe EAE. The incidence of severe EAE in rats treated with IL2NAg was significantly less than the incidence for rats treated with the combination of IL2 and NAg (p = 0.0055, Fisher's Exact Test). The mean number of days that IL2NAg-treated rats were severely afflicted with EAE was significantly less than the respective means for groups pretreated with saline or the combination of IL2 & GP69-88 (p ≤ 0.001 for all comparisons) (one-way parametric ANOVA; Tukey-Kramer Multiple Comparisons Test).

TABLE 21

The combination of NAgIL16 and IL2NAg strongly inhibits the effector phase of EAE.

| Treatment[a] | Incidence of EAE | Mean cumulative score | Median cumulative score | Mean maximal score | Median maximal score | Mean day of onset | Incidence of severe EAE (A-P) | Mean # days with severe EAE |
|---|---|---|---|---|---|---|---|---|
| Control | 7 of 7 | 8.5 ± 3.3 | 9.8 | 2.6 ± 0.8 | 3.0 | 9.4 ± 1.3 | 7 of 7 | 2.6 ± 1.4 |
| Cytokine/NAg | 5 of 5 | 0.5 ± 0.3 | 0.5 | 0.2 ± 0.1 | 0.3 | 11.3 ± 3.4 | 0 of 5 | 0.0 |

TABLE 22

NAgIL16 induces an active, dominant mechanism of tolerance.

| Exp. | Treatment[a] | Incidence of EAE | Mean cumulative score | Median cumulative score | Mean maximal score | Median maximal score | Incidence of severe EAE | Mean # days with severe EAE |
|---|---|---|---|---|---|---|---|---|
| 1 females | control | 9 of 9 | 9.1 ± 2.7 | 10.0 | 2.8 ± 0.4 | 3.0 | 9 of 9 | 2.8 ± 1.0 |
|   | NAg | 4 of 4 | 7.2 ± 3.0 | 6.8 | 2.8 ± 0.5 | 3.0 | 4 of 4 | 2.3 ± 1.3 |
|   | NAgIL16 | 4 of 4 | 3.9 ± 1.9 | 3.8 | 1.9 ± 1.0 | 2.0 | 3 of 4 | 1.0 ± 0.8 |

TABLE 22-continued

NAgIL16 induces an active, dominant mechanism of tolerance.

| Exp. | Treatment[a] | Incidence of EAE | Mean cumulative score | Median cumulative score | Mean maximal score | Median maximal score | Incidence of severe EAE | Mean # days with severe EAE |
|---|---|---|---|---|---|---|---|---|
| 2 males | control | 10 of 10 | 9.4 ± 2.9 | 8.5 | 2.8 ± 0.4 | 3.0 | 10 of 10 | 2.9 ± 0.9 |
| | NAg | 6 of 6 | 12.5 ± 2.4 | 12.3 | 3.0 ± 0.0 | 3.0 | 6 of 6 | 3.8 ± 1.2 |
| | NAgIL16 | 6 of 6 | 7.4 ± 4.7 | 7.6 | 2.1 ± 1.1 | 2.5 | 4 of 6 | 2.0 ± 1.7 |
| 1 & 2 | control | 19 of 19 | 9.2 ± 2.8 | 9.5 | 2.8 ± 0.4 | 3.0 | 19 of 19 | 2.8 ± 0.9 |
| | NAg | 10 of 10 | 10.4 ± 3.7 | 11.0 | 2.9 ± 0.3 | 3.0 | 10 of 10 | 3.2 ± 1.4 |
| | NAgIL16[b] | 10 of 10 | 6.0 ± 4.1 | 5.4 | 2.0 ± 1.0 | 2.0 | 7 of 10 | 1.6 ± 1.4 |

[a]Rats were pretreated with 4 nmoles of GP69-88 (NAg) or 4 nmoles NAgIL16 in saline on days −28, −21, and −14. On day −7, draining lymph node cells and splenocytes were pooled from rats of each group and were injected (i.p.) into recipient rats (1:1 donor to recipient ratio). Seven days after adoptive transfer, recipient rats were challenged on day 0 with 50 ug of DHFR-NAg in CFA.
[b]Combined experiments 1 & 2: Compared to recipients of NAgIL16-treated donor cells, the mean (p = 0.009, p = 0.034) and median (p = 0.007, p = 0.066) cumulative score, the mean (p = 0.010, p = 0.010) and median (p = 0.021, p = 0.049) maximal score, and the mean number of days afflicted with severe EAE (EP & P) (p = 0.010, p = 0.024) were significantly less than the respective scores of recipients of NAg-treated donor cells or untreated (control) rats, respectively.

The foregoing is illustrative of the present invention, and is not to be construed as limiting thereof. The invention is defined by the following claims, with equivalents of the claims to be included therein.

SEQUENCE LISTING

```
<160> NUMBER OF SEQ ID NOS: 33

<210> SEQ ID NO 1
<211> LENGTH: 7
<212> TYPE: PRT
<213> ORGANISM: Artificial
<220> FEATURE:
<223> OTHER INFORMATION: Cytokine-based fusion protein enterokinase
      domain sequence

<400> SEQUENCE: 1

Gly Asp Asp Asp Asp Lys Gly
1               5

<210> SEQ ID NO 2
<211> LENGTH: 15
<212> TYPE: PRT
<213> ORGANISM: Artificial
<220> FEATURE:
<223> OTHER INFORMATION: Cytokine-based fusion protein GPMBP
      encephalitogenic peptide sequence

<400> SEQUENCE: 2

Pro Gln Lys Ser Gln Arg Ser Gln Asp Glu Asn Pro Val Val His
1               5                   10                  15

<210> SEQ ID NO 3
<211> LENGTH: 26
<212> TYPE: PRT
<213> ORGANISM: Artificial
<220> FEATURE:
<223> OTHER INFORMATION: Cytokine-based fusion protein peptide sequence
      with His tag

<400> SEQUENCE: 3

Asp Asp Asp Asp Lys Gly Pro Gln Lys Ser Gln Arg Ser Gln Asp Glu
1               5                   10                  15

Asn Pro Val Val His His His His His His
            20                  25

<210> SEQ ID NO 4
<211> LENGTH: 5
<212> TYPE: PRT
<213> ORGANISM: Artificial
```

```
<220> FEATURE:
<223> OTHER INFORMATION: enterokinase cleavage site sequence

<400> SEQUENCE: 4

Asp Asp Asp Asp Lys
1               5

<210> SEQ ID NO 5
<211> LENGTH: 39
<212> TYPE: DNA
<213> ORGANISM: Artificial
<220> FEATURE:
<223> OTHER INFORMATION: PCR primer

<400> SEQUENCE: 5
ataactagta tggaaatctg caggggacct tacagtcac                          39

<210> SEQ ID NO 6
<211> LENGTH: 30
<212> TYPE: DNA
<213> ORGANISM: Artificial
<220> FEATURE:
<223> OTHER INFORMATION: PCR primer

<400> SEQUENCE: 6
ataactagta tggcctacag catgcagctc                                    30

<210> SEQ ID NO 7
<211> LENGTH: 34
<212> TYPE: DNA
<213> ORGANISM: Artificial
<220> FEATURE:
<223> OTHER INFORMATION: PCR primer

<400> SEQUENCE: 7
ataactagta tgggtctcag cccccacctt gctg                               34

<210> SEQ ID NO 8
<211> LENGTH: 37
<212> TYPE: DNA
<213> ORGANISM: Artificial
<220> FEATURE:
<223> OTHER INFORMATION: PCR primer

<400> SEQUENCE: 8
ataactagta tggcacttgg ctcagcactg ctatgtt                            37

<210> SEQ ID NO 9
<211> LENGTH: 31
<212> TYPE: DNA
<213> ORGANISM: Artificial
<220> FEATURE:
<223> OTHER INFORMATION: PCR primer

<400> SEQUENCE: 9
ataactagta tggcactctg ggtgactgca g                                  31

<210> SEQ ID NO 10
<211> LENGTH: 41
<212> TYPE: DNA
<213> ORGANISM: Artificial
<220> FEATURE:
<223> OTHER INFORMATION: PCR primer

<400> SEQUENCE: 10
cctttgtcat cgtcatcacc ttggtcttcc tggaagtaga a                       41
```

<210> SEQ ID NO 11
<211> LENGTH: 41
<212> TYPE: DNA
<213> ORGANISM: Artificial
<220> FEATURE:
<223> OTHER INFORMATION: PCR primer

<400> SEQUENCE: 11
cctttgtcat cgtcatcacc ctgagtcatt gttgagatga t         41

<210> SEQ ID NO 12
<211> LENGTH: 41
<212> TYPE: DNA
<213> ORGANISM: Artificial
<220> FEATURE:
<223> OTHER INFORMATION: PCR primer

<400> SEQUENCE: 12
cctttgtcat cgtcatcacc ggacatggaa gtgcaggact g         41

<210> SEQ ID NO 13
<211> LENGTH: 41
<212> TYPE: DNA
<213> ORGANISM: Artificial
<220> FEATURE:
<223> OTHER INFORMATION: PCR primer

<400> SEQUENCE: 13
cctttgtcat cgtcatcacc atttttcatt ttgagtgtca c         41

<210> SEQ ID NO 14
<211> LENGTH: 41
<212> TYPE: DNA
<213> ORGANISM: Artificial
<220> FEATURE:
<223> OTHER INFORMATION: PCR primer

<400> SEQUENCE: 14
cctttgtcat cgtcatcacc gtggccatag cggaaaagtt g         41

<210> SEQ ID NO 15
<211> LENGTH: 43
<212> TYPE: DNA
<213> ORGANISM: Artificial
<220> FEATURE:
<223> OTHER INFORMATION: PCR primer

<400> SEQUENCE: 15
gatgacgatg acaaaggacc ccagaagtcg cagcggtccc aag         43

<210> SEQ ID NO 16
<211> LENGTH: 65
<212> TYPE: DNA
<213> ORGANISM: Artificial
<220> FEATURE:
<223> OTHER INFORMATION: PCR primer

<400> SEQUENCE: 16
tatggtacct tagtgatggt gatggtgatg gactacaggg ttttcatctt gggaccgctg    60
cgact                                                                65

<210> SEQ ID NO 17
<211> LENGTH: 45
<212> TYPE: DNA

```
<213> ORGANISM: Artificial
<220> FEATURE:
<223> OTHER INFORMATION: PCR primer

<400> SEQUENCE: 17
atcatctcaa caatgactca gccccagaag tcgcagcggt cccaa          45

<210> SEQ ID NO 18
<211> LENGTH: 33
<212> TYPE: DNA
<213> ORGANISM: Artificial
<220> FEATURE:
<223> OTHER INFORMATION: PCR primer

<400> SEQUENCE: 18
ctgagtcatt gttgagatga tgctttgaca gat                      33

<210> SEQ ID NO 19
<211> LENGTH: 45
<212> TYPE: DNA
<213> ORGANISM: Artificial
<220> FEATURE:
<223> OTHER INFORMATION: PCR primer

<400> SEQUENCE: 19
cagtcctgca cttccatgtc cccccagaag tcgcagcggt cccaa          45

<210> SEQ ID NO 20
<211> LENGTH: 37
<212> TYPE: DNA
<213> ORGANISM: Artificial
<220> FEATURE:
<223> OTHER INFORMATION: PCR primer

<400> SEQUENCE: 20
ggacatggaa gtgcaggact gcaagtattt ccctcgt                  37

<210> SEQ ID NO 21
<211> LENGTH: 54
<212> TYPE: DNA
<213> ORGANISM: Artificial
<220> FEATURE:
<223> OTHER INFORMATION: PCR primer

<400> SEQUENCE: 21
tatggtacct tagtgatggt gatggtgatg ctgagtcatt gttgagatga tgct    54

<210> SEQ ID NO 22
<211> LENGTH: 53
<212> TYPE: DNA
<213> ORGANISM: Artificial
<220> FEATURE:
<223> OTHER INFORMATION: PCR primer

<400> SEQUENCE: 22
tatggtacct tagtgatggt gatggtgatg ggacatggaa gtgcaggact gca     53

<210> SEQ ID NO 23
<211> LENGTH: 54
<212> TYPE: DNA
<213> ORGANISM: Artificial
<220> FEATURE:
<223> OTHER INFORMATION: PCR primer

<400> SEQUENCE: 23
tatggtacct tagtgatggt gatggtgatg gtggccatag cggaaaagtt gctt    54
```

<210> SEQ ID NO 24
<211> LENGTH: 74
<212> TYPE: DNA
<213> ORGANISM: Artificial
<220> FEATURE:
<223> OTHER INFORMATION: PCR primer

<400> SEQUENCE: 24
gaccgctgcg acttctgggg cagggagcca taatggtgat ggtgatggtg atgggcatag    60
atgtaagaaa tgta                                                      74

<210> SEQ ID NO 25
<211> LENGTH: 72
<212> TYPE: DNA
<213> ORGANISM: Artificial
<220> FEATURE:
<223> OTHER INFORMATION: PCR primer

<400> SEQUENCE: 25
ataactagta tgaaattctt agtcaacgtt gcccttgttt ttatggtcgt atacatttct    60
tacatctatg cc                                                        72

<210> SEQ ID NO 26
<211> LENGTH: 72
<212> TYPE: DNA
<213> ORGANISM: Artificial
<220> FEATURE:
<223> OTHER INFORMATION: PCR primer

<400> SEQUENCE: 26
tccctgcccc agaagtcgca gcggtcccaa gatgaaaacc ctgtagtcca ttctgctgca    60
tcagcttcag ta                                                        72

<210> SEQ ID NO 27
<211> LENGTH: 36
<212> TYPE: DNA
<213> ORGANISM: Artificial
<220> FEATURE:
<223> OTHER INFORMATION: PCR primer

<400> SEQUENCE: 27
tatggtacct tatgagtctg cagaagctgt tgtctg                              36

<210> SEQ ID NO 28
<211> LENGTH: 65
<212> TYPE: DNA
<213> ORGANISM: Artificial
<220> FEATURE:
<223> OTHER INFORMATION: PCR primer

<400> SEQUENCE: 28
ataactagta tggcattctt agtcaacgtt gcccttgttt ttatggtcgt atacatttct    60
tacat                                                                65

<210> SEQ ID NO 29
<211> LENGTH: 62
<212> TYPE: DNA
<213> ORGANISM: Artificial
<220> FEATURE:
<223> OTHER INFORMATION: PCR primer

<400> SEQUENCE: 29

```
gcagaatggt gatggtgatg gtgatgggca tagatgtaag aaatgtatac gaccataaaa    60
ac                                                                  62

<210> SEQ ID NO 30
<211> LENGTH: 44
<212> TYPE: DNA
<213> ORGANISM: Artificial
<220> FEATURE:
<223> OTHER INFORMATION: PCR primer

<400> SEQUENCE: 30
catcaccatc accatcacca ttctgctgca tcagcttcag tagc                    44

<210> SEQ ID NO 31
<211> LENGTH: 40
<212> TYPE: DNA
<213> ORGANISM: Artificial
<220> FEATURE:
<223> OTHER INFORMATION: PCR primer

<400> SEQUENCE: 31
gacaacagct tctgcagact tgtaaggtac caagcttgtc                         40

<210> SEQ ID NO 32
<211> LENGTH: 30
<212> TYPE: DNA
<213> ORGANISM: Artificial
<220> FEATURE:
<223> OTHER INFORMATION: PCR primer

<400> SEQUENCE: 32
agtctgcaga agctgttgtc tgcttgccct                                    30

<210> SEQ ID NO 33
<211> LENGTH: 20
<212> TYPE: PRT
<213> ORGANISM: Artificial
<220> FEATURE:
<223> OTHER INFORMATION: GP69-88 encephalitogenic peptide sequence

<400> SEQUENCE: 33

Tyr Gly Ser Leu Pro Gln Lys Ser Gln Arg Ser Gln Asp Glu Asn Pro
1               5                   10                  15

Val Val His Phe
            20
```

What is claimed is:

1. A method of treating multiple sclerosis comprising administering to a subject an effective amount of a first and at least a second fusion protein, wherein the first and the at least second fusion protein each independently comprise:
   (a) an encephalitogenic determinant of an autoimmune antigen selected from the group consisting of myelin basic protein (MBP), proteolipid protein (PLP), myelin oligodendrocyte glycoprotein (MOG) and myelin-associated oligodendrocytic basic protein; and
   (b) an anti-inflammatory cytokine selected from the group consisting of an interleukin or interleukin receptor antagonist,
wherein the anti-inflammatory cytokine of the first fusion protein is interleukin-2 (IL-2) and the anti-inflammatory cytokine of the at least second fusion protein is interleukin-4 (IL-4), interleukin-10 (IL-10), interleukin-13 (IL-13), interleukin-16 (IL-16), interferon-beta (IFN-β) or transforming growth factor-beta (TGF-β) and the interleukin receptor antagonist is interleukin-1RA (IL-1RA).

2. The method of claim 1, wherein the autoimmune antigen is a myelin basic protein.

3. The method of claim 2, wherein the encephalitogenic determinant of the myelin basic protein comprises the amino acid sequence of SEQ ID NO:2.

4. The method of claim 1, wherein the anti-inflammatory cytokine of the at least second fusion protein is interleukin-4 (IL-4), or interleukin-16 (IL-16).

5. The method of claim 1, wherein the anti-inflammatory cytokine of the at least second fusion protein is interleukin-16 (IL-16).

6. The method of claim 1, wherein the anti-inflammatory cytokine of the at least second fusion protein is interferon-beta (IFN-β).

7. The method of claim 1, wherein the anti-inflammatory cytokine of the at least second fusion protein is transforming growth factor-beta (TGF-β).

8. The method of claim 1, wherein the autoimmune antigen is a proteolipid protein.

9. The method of claim 1, wherein the autoimmune antigen is a myelin oligodendrocyte glycoprotein.

10. A method of treating multiple sclerosis comprising administering to a subject an effective amount of a first and at least a second fusion protein, wherein the first and the at least second fusion protein each independently comprise:
  (a) an encephalitogenic determinant of an autoimmune antigen selected from the group consisting of myelin basic protein (MBP), proteolipid protein (PLP), myelin oligodendrocyte glycoprotein (MOG) and myelin-associated oligodendrocytic basic protein; and
  (b) an anti-inflammatory cytokine selected from the group consisting of an interleukin or interleukin receptor antagonist, wherein the interleukin of the first fusion protein is interleukin-16 (IL-16) and the interleukin of the at least second fusion protein is interleukin-2 (IL-2).

* * * * *

UNITED STATES PATENT AND TRADEMARK OFFICE
CERTIFICATE OF CORRECTION

PATENT NO. : 8,920,808 B2  
APPLICATION NO. : 12/447389  
DATED : December 30, 2014  
INVENTOR(S) : Mannie Page 1 of 2

It is certified that error appears in the above-identified patent and that said Letters Patent is hereby corrected as shown below:

Column 31, Line 29: "(referred to IFN 3.4)" should read -- (referred to IFNβ.4) --

Column 45, TABLE 3, Primer name (code):
   "5'   IL-1RA    (3B05)" should read -- 5'   IL-1RA    (3B05)* --

Columns 69 and 70, SEQUENCE LISTING: insert Sequence numbers 34, 35, and 36 as shown below immediately after Sequence 33:

<210> 34
    <211> 21
    <212> PRT
    <213> Apis andreniformis

<400> 34

Met Lys Phe Leu Val Asn Val Ala Leu Val Phe Met Val Val Tyr Ile
    1               5                   10                  15

Ser Tyr Ile Tyr Ala
    --          20

Signed and Sealed this  
Twenty-fourth Day of November, 2015

Michelle K. Lee  
*Director of the United States Patent and Trademark Office*

<210> 35
<211> 19
<212> PRT
<213> Artificial

<220>
<223> GP69-87 encephalitogenic peptide sequence

<400> 35

Tyr Gly Ser Leu Pro Gln Lys Ser Gln Arg Ser Gln Asp Glu Asn Pro
1               5                   10                  15

Val Val His

<210> 36
<211> 21
<212> PRT
<213> Artificial

<220>
<223> Modified honeybee mellitin signal sequence

<400> 36

Met Ala Phe Leu Val Asn Val Ala Leu Val Phe Met Val Val Tyr Ile
1               5                   10                  15

Ser Tyr Ile Tyr Ala
            20